United States Patent
Kosugi et al.

(10) Patent No.: US 7,667,036 B2
(45) Date of Patent: Feb. 23, 2010

(54) PYRAZOLO[1,5-A]PYRIMIDINE DERIVATIVES

(75) Inventors: Tomomi Kosugi, Tokyo (JP); Minoru Imai, Tokyo (JP); Hiroaki Makino, Tokyo (JP); Mika Takakuwa, Tokyo (JP); Gen Unoki, Tokyo (JP); Kenichiro Kataoka, Tokyo (JP); Dale Robert Mitchell, Essex (GB); Donald James Simpson, Essex (GB); Clifford John Harris, Essex (GB); Joelle Le, Essex (GB); Yuko Yamakoshi, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 266 days.

(21) Appl. No.: 11/202,035

(22) Filed: Aug. 12, 2005

(65) Prior Publication Data

US 2006/0135514 A1    Jun. 22, 2006

Related U.S. Application Data

(60) Provisional application No. 60/603,535, filed on Aug. 24, 2004.

(30) Foreign Application Priority Data

Aug. 13, 2004    (JP) ............... 2004-236035

(51) Int. Cl.
*C07D 487/04* (2006.01)
*A61K 31/519* (2006.01)
*A61P 35/04* (2006.01)
*A61P 25/28* (2006.01)

(52) U.S. Cl. .................. 544/281; 514/259.3
(58) Field of Classification Search .............. 544/282; 514/259.31, 259.3
See application file for complete search history.

(56) References Cited

U.S. PATENT DOCUMENTS 7,067,520 B2 * 6/2006 Kato et al. ............ 514/259.3

7,161,003 B1 * 1/2007 Guzi et al. ............ 544/281

FOREIGN PATENT DOCUMENTS

| JP | 11279178 A | 10/1999 |
| JP | 11279198 | * 12/1999 |
| WO | 0240485 A1 | 5/2002 |
| WO | 2004022561 A1 | 3/2004 |
| WO | 2004087707 A1 | 10/2004 |
| WO | WO 2004110454 | * 12/2004 |

OTHER PUBLICATIONS

Shiota et. al. (Chem. and Pharm. Bull., 1999, 47(7), 928-938).*
Machine Translation of JP 11-279178, downloaded Mar. 25, 2008.*
CAS online structure search downloaded Mar. 24, 2008.*
Miller et. al. (Advances in Cyclic Nucleotide and Proteins Phosphorylation Research, 1984, 16, 277-290).*
D. Williamson et al. "Structure-guided design in pyrazolo[1,5-a]pyrimidines as inhibitors of human cyclin-dependent kinase 2" Bioorganic & Medicinal Chemistry Letters, vol. 15, No. 4, pp. 863-867, 2005.
Paruch et al., "Pyrazolo[1,5-α]pyrimidines as orally available inhibitors of cyclin-dependent kinase 2", Biorganic & Medicinal Chemistry Letters, 17:6220-6223 (2007).

* cited by examiner

*Primary Examiner*—Brenda L Coleman
*Assistant Examiner*—Susanna Moore
(74) *Attorney, Agent, or Firm*—Sughrue Mion, PLLC

(57) ABSTRACT

The Pyrazolo[1,5-a]pyrimidine derivatives represented by formula I and their pharmaceutically acceptable salts exhibit excellent MAPKAP-K2 inhibiting activity. Drugs comprising the compounds as effective ingredients are therefore expected to be useful as therapeutic or prophylactic agents for MAPKAP-K2 mediated disorder, such as inflammatory disease, autoimmune disease, destructive bone disorder, cancer and/or tumour growth.

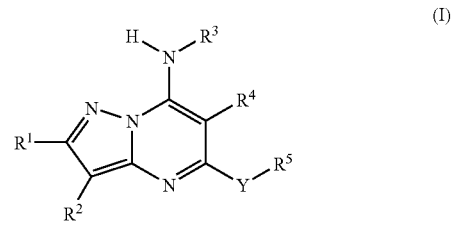

31 Claims, 8 Drawing Sheets

Ms : methanesulfonyl

HATU : O-(7-azabenzotriazol-1-yl) N,N,N',N'-tetramethyluronium hexafuluorophosphate
TMSI : iodo trimethylsilane

PYRAZOLO[1,5-A]PYRIMIDINE DERIVATIVES

This application claims priority to Japanese Patent Application No. 2004-236035, filed Aug. 13, 2004 and U.S. Provisional Application No. 60/603,535, filed Aug. 24, 2004; the entire disclosure of which are incorporated herein by reference.

FIELD OF THE INVENTION

The present invention relates to novel compounds, their use in the inhibition of MAPKAP-K2 (mitogen-activated protein kinase-activated protein kinase 2), their use in medicine and particularly in the prevention and/or treatment of a wide variety of diseases including inflamrnatory disorders, cancer, angiogenesis, diabetes and neurological disorders. The invention also provides processes for the manufacture of said compounds, compositions containing them and processes for manufacturing such compositions.

BACKGROUND ART

Protein kinases are a family of enzymes that catalyse the phosphorylation of hydroxyl groups in proteins. Approximately 2% of the genes encoded by the human genome are predicted to encode protein kinases. The phosphorylation of specific tyrosine, serine, or threonine residues on a target protein can dramatically alter its function in several ways including activating or inhibiting enzymatic activity, creating or blocking binding sites for other proteins, altering subcellular localisation or controlling protein stability. Consequently, protein kinases are pivotal in the regulation of a wide variety of cellular processes, including metabolism, proliferation, differentiation and survival (Hunter, T. Cell, 1995, 80, 224-236). Of the many different cellular functions known to require the actions of protein kinases, some represent targets for therapeutic intervention for certain disease (Cohen, P. Nature Rev. Drug Disc., 2002, 1, 309-315).

It is known that several diseases arise from, or involve, aberrant protein kinase activity. In humans, protein tyrosine kinases are known to have a significant role in the development of many diseases including diabetes, cancer and have also been linked to a wide variety of congenital syndromes (Robertson, S. C. Trends Genet. 2000, 16, 265-271). Serine/threonine kinases also represent a class of enzymes, inhibitors of which are likely to have relevance to the treatment of cancer, diabetes and a variety of inflammatory disorders (Adams, J. L. et al. Prog. Med. Chem. 2001, 38, 1-60).

One of the principal mechanisms by which cellular regulation is affected is trough the transduction of extracellular signals across the membrane that in turn modulate biochemical pathways within the cell. Protein phosphorylation represents one course by which intracellular signals are propagated from molecule to molecule resulting finally in cellular responses. These signal transduction cascades are regulated and often overlapping as evidenced by the existence of many protein kinases as well as phosphatases. It is currently believed that a number of disease and/or disorders are a result of either aberrant activation or inhibition in the molecular components of kinase cascades.

Three potential mechanisms for inhibition of protein kinases have been identified thus far. These include a pseudo-substrate mechanism, an adenine mimetic mechanism and the locking of the enzyme into an inactive conformation by using surfaces other than the active site (Taylor, S. S. Curr. Opin. Chem. Biol. 1997, 1, 219-226). The majority of inhibitors identified/designed to date act at the ATP-binding site. Such ATP-competitive inhibitors have demonstrated selectivity by virtue of their ability to target the more poorly conserved areas of the ATP-binding site (Wang, Z. et al. Structure 1998, 6, 1117-1128).

There exists a need for the provision of further compounds that are inhibitors of protein kinases.

MAPKAP-K2 (mitogen-activated protein kinase-activated protein kinase 2) is a serine/threonine kinase that operates immediately downstream of the p38 kinase in the stress-induced MAPK pathway (FIG. 1).

The p38 kinase pathway is involved in transducing the effects of a variety of stress-related extracellular stimuli such as heat shock, UV light, bacterial lipopolysaccharide, and pro-inflammatory cytokines. Activation of this pathway results in the phosphorylation of transcription and initiation factors, and affects cell division, apoptosis, invasiveness of cultured cells and the inflammatory response (Martin-Blanco, Bioessays 22, 637-645 (2000)).

p38 kinase itself activates a number of protein kinases other than the MAPKAP kinases such as Mnk1/2, PRAK and MSK1 (FIG. 1). The specific and/or overlapping functions of the majority of these targets have yet to be resolved. This pathway has been of particular interest for the discovery of new anti-inflammatory agents. Previous strategies to intervene this pathway have involved the development of selective inhibitors of p38 kinase. Such inhibitors are effective both for inhibiting pro-inflanunatory cytokine production in cell-based models and animal models of chronic inflammations (Lee et al., Immunopharmacology 47, 185-201 (2000)). p38 kinase knockout mouse is embryonic lethal. And cells derived from such embryos have demonstrated a number of abnormalities in findamental cell responses. These observations indicate that caution should be paid to the long-term therapy with p38 kinase inhibitors.

An alternative strategy for the development of anti-inflammatory agents could be the inhibition of this pathway at the level of MAPKAP-K2. Human MAPKAP-K2 has two proline-rich domains at its N-terminus followed by the kinase domain and the C-terminal regulatory domain. This kinase has low homology with other serine/threonine kinases except MAPKAP-K3 and -K4. The C-terminal regulatory domain contains a bipartite nuclear localisation signal and a nuclear export signal. The crystal structure of inactive MAPKAP-K2 has been resolved (Meng, W. et al. J. Biol. Chem. 277, 37401-37405 (2002)). Activation of MAPKAP-K2 by p38 kinase occurs via selective phosphorylation of threonine residues 222 and 334 (Stokoe et al., EMBO J. 11, 3985-3994 (1992)). MAPKAP-K2 has an amphiphilic α-helix motif located within its C-terminal region that is likely to block the binding of substrates. The dual phosphorylation by p38 kinase has been proposed to reposition this motif resulting in enhanced catalytic activity (You-Li et al., J. Biol. Chem. 270, 202-206 (1995)). MAPKAP-K2 is present in the nucleus of unstimulated cells, and translocates to the cytoplasm upon cell stimulation. This kinase is known to phosphorylate a number of nuclear transcription factors as well as cytosolic proteins such as heat shock proteins and 5-lipoxygenase (Stokoe et al., FEBS Let. 313, 307-313 (1992), Werz, et al., Proc. Natl. Acad. Sci. USA 97, 5261-5266 (2000), Heidenreich, et al., J. Biol. Chem. 274, 14434-14443 (1999), Tan, et al., EMBO J. 15, 4629-4642 (1996), Neufeld, J. Biol. Chem. 275, 20239-20242 (2000)). All such substrates contain a unique amino acid motif (XX-Hyd-XRXXSXX, where Hyd is a bulky hydrophobic residue) that is required for efficient phosphorylation by MAPKAP-K2 (Stokoe et al., Biochem. J. 296, 843-849 (1993)).

Currently MAPKAP-K2 is the only p38 kinase substrate for which a specific function has been identified. A specific role for MAPKAP-K2 in mediating the inflammatory response has been strongly indicated by the phenotype of the MAPKAP-K2-deficient mouse (MAPKAP-K2) (Kotlyarov, et al., Nature Cell Biol. 1, 94-97 (1999)). This mouse is viable and normal except for a significantly reduced inflammatory response. Recently it has also been shown that MAPKAP-K2 deficiency results in a marked neuroprotection from ischaemic brain injury (Wang et al., J. Biol Chem. 277, 43968-43972 (2002)). MAPKAP-K2 is believed to regulate the translation and/or stability of important pro-inflammatory cytokine mRNAs. It is thought to function via phosphorylation of proteins that bind to the AU-rich elements found within untranslated regions of these cytokines The identity of these proteins is currently under investigation.

MAPKAP-K2 therefore represents an intervention point in the stress-induced kinase cascade for perturbation of the inflammatory response.

DISCLOSURE OF THE INVENTION

As a result of much diligent research directed toward achieving the object stated above, the present inventors have completed the present invention upon discovering that the novel pyrazolo[1,5-a]pyrimidine derivatives represented by formula I below and their pharmaceutically acceptable salts exhibit excellent MAPKAP-K2 inhibiting activity.

In other words, the present invention provides as follows:
(1) A compound of formula (I) and pharmaceutically acceptable salts, and other pharmaceutically acceptable biohydrolyzable derivatives thereof, including esters, amides, carbamates, carbonates, ureides, solvates, hydrates, affinity reagents, or prodrugs:

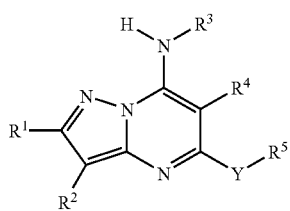

(I)

wherein
$R^1$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

$R^2$ is hydrogen, halogen, —CN, —NO$_2$, —CHO, -G-R$^7$ [G is a single bond, —C(=O)— or —O—C(=O)—; and R$^7$ is C1-C8 optionally substituted alkyl, C2-C8 optionally substituted alkenyl, C2-C8 optionally substituted allynyl, C3-C8 optionally substituted cycloalkyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^8$ (R$^8$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl), —NR$^9$R$^{10}$ (R$^9$ is as defined for R$^8$; R$^{10}$ is hydrogen, C1-C8 optionally substituted alkyl, C3-C8 optionally substituted cycloalkyl, C6-C14 optionally substituted aryl, optionally substituted heterocyclyl, optionally substituted arylalkyl, optionally substituted heterocyclylalkyl or —OCH$_3$), —R$^{11}$ (R$^{11}$ is an optionally substituted saturated heterocyclyl with 5 to 7 members containing one to four heteroatoms selected from N, O and S), C6-C14 optionally substituted aryl or optionally substituted heteroaryl; provided that when R$^7$ is C6-C14 optionally substituted aryl or optionally substituted heteroaryl, then G is not a single bond], —NR$^9$C(=O)R$^{12}$ (R$^9$ is as defined for R$^8$; R$^{12}$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl), —NR$^9$C(=X)OR$^{13}$ (R$^9$ and R$^{13}$, which may be the same or different, are as defined for R$^8$; X is O, S, N—CN or NH), —NR$^9$C(=X)NR$^{13}$R$^{14}$ (R$^9$, R$^{13}$ and R$^{14}$, which may be the same or different, are as defined for R$^8$; X is O, S, N—CN or NH), —NR$^9$SO$_2$R$^{13}$ (R$^9$ and R$^3$, which may be the same or different, are as defined for R$^8$) —SR$^9$ (R$^9$ is as defined for R$^8$), or —S(O)$_n$R$^9$(R$^9$ is as defined for R$^8$; n is 1 or 2);

$R^3$ is C1-C8 optionally substituted alkyl, C2-C8 optionally substituted alkenyl, C2-C8 optionally substituted alkynyl, C3-C8 optionally substituted cycloalkyl, C6-C14 unsubstituted aryl, C6-C14 substituted aryl [As substituents of C6-C14 aryl may be mentioned 1 or 2 or more selected from the group consisting of halogen, —CN, —NO$_2$, —CHO, -G-R$^{15}$ {G is a single bond, —C(=O)— or —O—C(=O)—; R$^{15}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{16}$ (R$^{16}$ is as defined for R$^8$) or —NR$^{17}$R$^{18}$ (R$^{17}$ and R$^{18}$, which may be the same or different, are as defined for R$^8$)}, —NR$^{17}$C(=O)R$^{19}$ (R$^{17}$ is as defined for R$^8$; R$^{19}$ is as defined for R$^{12}$), —NR$^{17}$C(=X)OR$^{18}$ (R$^{17}$ and R$^{18}$, which may be the same or different, are as defined for R$^8$; X is O, S, N—CN or NH), —N$^{17}$C(=X)NR$^{18}$R$^{20}$ (R$^{17}$, R$^{18}$ and R$^{20}$, which may be the same or different, are as defined for R$^8$; X is O, S, N—CN or NH), —NR$^{17}$SO$_2$R$^{18}$ (R$^{17}$ and R$^{18}$, which may be the same or different, are as defined for R$^8$), —S(O)$_m$R$^{17}$ (R$^{17}$ is as defined for R$^8$; m is 0, 1 or 2) and —SO$_2$NR$^{21}$R$^{22}$ (R$^{21}$ and R$^{22}$, which may be the same or different, are as defined for R$^8$; R$^{21}$ and R$^{22}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with 1 or 2 or more substituents)], unsubstituted heterocyclyl, substituted heterocyclyl [As substituents of heterocyclyl may be mentioned 1 or 2 or more selected from the group consisting of halogen, —CN, —NO$_2$, —CHO, -G-R$^{23}$ {G is a single bond, —C(=O)— or —O—C(=O)—; R$^{23}$ is as defined for R$^{15}$}, —NR$^{24}$C(=O)R$^{25}$ (R$^{24}$ is as defined for R$^8$; R$^{25}$ is as defined for R$^{12}$), —NR$^{24}$C(=X)OR$^{26}$ (R$^{24}$ and R$^{26}$, which may be the same or different, are as defined for R$^8$; X is O, S, N—CN or NH), NR$^{24}$C(=X)NR$^{26}$R$^{27}$ (R$^{24}$, R$^{26}$ and R$^{27}$, which may be the same or different, are as defined for R$^8$; X is O, S, N—CN or NH), —NR$^{24}$SO$_2$R$^{26}$ (wherein R$^{24}$ and R$^{26}$, which may be the same or different, are as defined for R$^8$), —S(O)$_m$R$^{24}$ (R$^{24}$ is as defined for R$^8$; m is 0, 1 or 2) and —SO$_2$NR$^{28}$R$^{29}$R$^{28}$ and R$^{29}$, which may be the same or different, are as defined for R$^8$; (R$^{28}$ and R$^{29}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with 1 or 2 or more substituents)], optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

R$^4$ is hydrogen, halogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{30}$ (R$^{30}$ is as defined for R$^8$), —SR$^{30}$ (R$^{30}$ is as defined for R$^8$), —NR$^{30}$R$^{31}$ and R$^{31}$, which may be the same or different, are as defined for R$^8$), —NR$^{30}$C(=O)R$^{32}$ (R$^{30}$ is as defined for R$^8$; and R$^{32}$ is as defined for R$^{12}$), —NR$^{30}$C(=X)OR$^{31}$ (R$^{30}$ and R$^{31}$, which may be the same or different, are as defined R$^8$; X is O, S, N—CN or NH), —NR$^{30}$C(=X)NR$^{31}$R$^{33}$ (R$^{30}$, R$^{31}$ and R$^{33}$, which may be the same or different, are as defined for R$^8$; X is O, S, N—CN or NH) or —NR$^{30}$SO$_2$R$^{31}$ (R$^{30}$ and R$^{31}$, which may be the same or different, are as defined for R$^8$);

R$^5$ is C1-C8 substituted alkyl, C2-C8 optionally substituted alkenyl, C2-C8 optionally substituted alkynyl, C3-C8 substituted cycloalkyl [As substituents of C3-C8 cycloalkyl may be mentioned 1 or 2 or more selected from the group consisting of halogen, —CN, —NO$_2$, —CHO, =O, -G-R$^{34}$ {G is a single bond, —C(=O)— or —O—C(=O)—; R$^{34}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{35}$ (R$^{35}$ is as defined for R$^8$) or —NR$^{36}$R$^{37}$ (R$^{36}$ and R$^{37}$, which may be the same or different, are as defined for R$^8$)}, —NR$^{38}$C(=O)R$^{39}$ (R$^{38}$ is as defined for R$^8$; R$^{39}$ is as defined for R$^{12}$), —NR$^{38}$C(=X)OR$^{40}$ (R$^{38}$ and R$^{40}$, which may be the same or different, are as defined for R$^8$; X is O, S, N—CN or NH), —NR$^{38}$C(=X)NR$^{40}$R$^{41}$ (R$^{38}$, R$^{40}$ and R$^{41}$, which may be the same or different, are as defined for R$^8$; X is O, S, N—CN or NH) and —NR$^{38}$SO$_2$R$^{40}$ (R$^{38}$ and R$^{40}$, which may be the same or different, are as defined for R$^8$)], unsubstituted heterocyclyl, substituted heterocyclyl [As substituents of heterocyclyl may be mentioned 1 or 2 or more selected from the group consisting of halogen, —CN, —NO$_2$, —CHO, =O, -G-R$^{42}$ {G is a single bond, —C(=O)— or —O—C(=O)—; R$^{42}$ is C1-8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{43}$ (R$^{43}$ is as defined for R$^8$) or —NR$^{44}$R$^{45}$ (R$^{46}$ and R$^{45}$, which may be the same or different, are as defined for R$^8$)}, —NR$^{46}$C(=O)R$^{47}$ (R$^{46}$ is as defined for R$^8$; R$^{47}$ is as defined for R$^{12}$), —NR$^{46}$C(=X)OR$^{48}$ (R$^{46}$ and R$^{48}$, which may be the same or different, are as defined for R$^8$; X is O, S, N—CN or NH), —NR$^{46}$C(=X)NR$^{48}$R$^{49}$ (R$^{46}$, R$^{48}$ and R$^{49}$, which may be the same or different, are as defined for R$^8$; X is O, S, N—CN or NH) and NR$^{46}$SO$_2$R$^{48}$ (R$^{46}$ and R$^{48}$, which may be the same or different, are as defined for R$^8$)], optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

Y is —O— or —S—;

provided that R$^5$ is not C1-C6 alkyl which is unsubstituted or substituted (with 1 or 2 or more phenyls or halogens).

(2) The compound as defined in (1) wherein R$^1$ is hydrogen or C1-8 optionally substituted alkyl.

(3) The compound as defined in (1) wherein R$^1$ is hydrogen.

(4) The compound as defined in any one of (1) to (3) wherein R$^2$ is hydrogen, halogen, C1-8 optionally substituted alkyl or C3-C8 optionally substituted cycloakyl, (5) The compound as defined in any one of (1) to (3) wherein R is C1-C8 optionally substituted alkyl or C3-C8 optionally substituted cycloalkyl.

(6) The compound as defined in any one of (1) to (3) wherein R$^2$ is hydrogen or halogen.

(7) The compound as defined in any one of (1) to (3) wherein R$^2$ is halogen.

(8) The compound as defined in any one of (1) to (3) wherein R$^2$ is hydrogen.

(9) The compound as defined in any one of (1) to (8) wherein R$^3$ is C6C14 substituted aryl {As substituents of C6-C14 aryl may be mentioned 1 or 2 or more selected from the group consisting of halogen, —CN, -G-R$^{15}$, —NR$^{17}$C(=O)R$^{19}$ and —S(O)$_m$R$^{17}$; wherein R$^{15}$, R$^{17}$, R$^{19}$ or G are as defined in (1); m is 0, 1 or 2.}unsubstituted heteroaryl or substituted heteroaryl.

(10) The compound as defined in any one of (1) to (8) wherein R$^3$ is C6-C14 substituted aryl [As substituents of C6-C14 aryl may be mentioned 1 or 2 or more selected from the group consisting of halogen, —CN, -G-R$^{15}$ {G is a single bond or —C(=O)—; R$^{15}$ is C1-C8 optionally substituted alkyl, C3-C8 optionally substituted cycloalkyl, C6-C14 optionally substituted aryl, optionally substituted heterocyclyl, optionally substituted arylalkyl, optionally substituted heterocyclylalkyl, —OR$^{16}$ or —NR$^{17}$R$^{18}$},NR$^{17}$C(=O)R$^{19}$, NR$^{17}$SO$_2$R$^{18}$ and —SO$_2$NR$^{21}$R$^{22}$; wherein R$^{16}$, R$^{17}$, R$^{18}$, R$^{19}$, R$^{21}$ or R$^{22}$ are as defined in (1).].

(11) The compound as defined in any one of (1) to (8) wherein R$^3$ is C6-C14 substituted aryl [As substituents of C6-C14 aryl may be mentioned 1 or 2 or more selected from the group consisting of halogen, —CN, -G-R$^{15}$ {G is a single bond; R$^{15}$ is C6-C14 optionally substituted aryl, optionally substituted heterocyclyl, optionally substituted arylalkyl, optionally substituted heterocyclylalkyl, —OR$^{16}$ or —NR$^{17}$R$^{18}$}, —NR$^{17}$C(=O)R$^{19}$, —NR$^{17}$SO$_2$R$^8$ and —SO$_2$NR$^{21}$R$^{22}$; wherein R$^{16}$, R$^{17}$, R$^{18}$, R$^{19}$, R$^{21}$ or R$^{22}$ are as defined in (1).].

(12) The compound as defined in any one of (1) to (8) wherein R$^3$ is C6-C14 substituted aryl [As substituents of C6-C14 aryl may be mentioned 1 or 2 or more selected from the group consisting of halogen, —CN, and -G-R$^{15}$ {G is —C(=O)—; R$^{15}$ is C1-C8 optionally substituted alkyl, C6-C14 optionally substituted aryl, C3-C8 optionally substituted cycloalkyl, —OR$^{16}$ or —NR$^{17}$R$^{18}$}, wherein R$^{16}$, R$^{17}$ or R$^{18}$ are as defined in (1).].

(13) The compound as defined in any one of (1) to (8) wherein R$^3$ is substituted bicyclic heteroaryl [As substituents of heterocyclyl may be mentioned 1 or 2 or more selected from the group consisting of halogen, —CN, -G-R$^{23}$, —NR$^{24}$C(=O)R$^{25}$ and —SO$_2$NR$^{28}$R$^{29}$; wherein R$^{23}$, R$^{24}$, R$^{25}$R$^{28}$, R$^{29}$ or G are as defined in (1).].

(14) The compound as defined in any one of (1) to (8) wherein R$^3$ is unsubstituted bicyclic heteroaryl.

(15) The compound as defined in any one of (1) to (14) wherein R$^4$ is hydrogen, halogen, C1-C8 optionally substituted alkyl, C2-C8 optionally substituted alkenyl or C3-C8 optionally substituted cycloalkyl.

(16) The compound as defined in any one of (1) to (14) wherein R$^4$ is C1-C8 optionally substituted allkyl.

(17) The compound as defined in any one of (1) to (14) wherein R$^4$ is methyl.

(18) The compound as defined in any one of(1) to (14) wherein R$^4$ is hydrogen.

(19) The compound as defined in any one of (1) to (18) wherein R$^5$ is C1-C8 substituted alkyl, C3-C8 substituted cycloalkyl, unsubstituted heterocyclyl or substituted heterocyclyl.

(20) The compound as defined in any one of (1) to (18) wherein R$^5$ is C3-C8 substituted cycloalkyl [As substituents of C3-C8 cycloalkyl may be mentioned 1 or 2 or more selected from the group consisting of halogen, —CN, =O, C1-C8 optionally substituted alkyl, C2-C8 optionally substituted alkenyl, C3-C8 optionally substituted cycloalkyl, —OR$^{35}$ and —NR$^{36}$R$^{37}$; wherein R$^{35}$, R$^{36}$ or R$^{37}$ is as defined in (1)].

(21) The compound as defined in any one of (1) to (18) wherein R$^5$ is substituted cyclohexyl [As substituents of cyclohexyl may be mentioned 1 or 2 or more selected from the group consisting of halogen, —CN, =O, C1-C8 optionally substituted alkyl, C2-C8 optionally substituted alkenyl, C3-C8 optionally substituted cycloalkyl, —OR$^{35}$ and —NR$^{36}$R$^{37}$; wherein R$^{35}$, R$^{36}$ or R$^{37}$ is as defined in (1)].

(22) The compound as defined in any one of (1) to (18) wherein R$^5$ is 4-amino-cyclohexyl.

(23) The compound as defined in any one of (1) to (18) wherein R$^5$ is unsubstituted heterocyclyl or substituted heterocyclyl [As substituents of heterocyclyl may be mentioned 1 or 2 or more selected from the group consisting of halogen, —CN, =O, C1-C8 optionally substituted alkyl, C2-C8 optionally substituted alkenyl, C3-C8 optionally substituted cycloalkyl, —OR$^{35}$ and —NR$^{44}$R$^{45}$; wherein R$^{35}$, R$^{44}$ or R$^{45}$ is as defined in (1)]

(24) The compound as defined in any one of (1) to (18) wherein R$^5$ is unsubstituted piperidin-3-yl, unsubstituted piperidin-4-yl or unsubstituted pyrrolidin-3-yl.

(25) The compound as defined in any one of (1) to (18) wherein R$^5$ is substituted piperidin-3-yl, substituted piperidin-4-yl or substituted pyrrolidin-3-yl.

(26) The compound as defined in any one of (1) to (18) wherein R$^5$ is substituted piperidin-3-yl, substituted piperidin-4-yl or substituted pyrrolidin-3-yl [As their substituents may be mentioned 1 or 2 or more selected from the group consisting of halogen, —CN, C1-C8 optionally substituted alkyl, C2-C8 optionally substituted alkenyl and C3-C8 optionally substituted cycloalkyl]

(27) The compound as defined in any one of (1) to (26) wherein Y is —O—.

(28) The compound as defined in any one of (1) to (26) wherein Y is —S—.

(29) The compound as defined in any one of (1) to (28) wherein R$^1$, R$^2$ and R$^4$ are not all hydrogen.

(30) The compound as defined in any one of (1) to (28) wherein R$^1$, R$^2$ and R$^4$ are all hydrogen.

(31) A compound of the formula II-20:

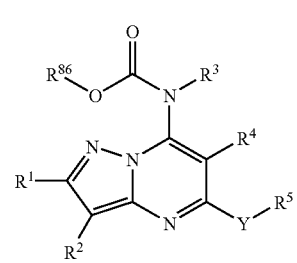

(II-20)

wherein R$^1$-R$^5$ and Y are as defined in (1); R$^{86}$ is C1-C8 optionally substituted alkyl or optionally substituted arylalkyl;

(32) The compound as defined in (31) wherein R$^1$ is hydrogen.

(33) The compound as defined in (31) wherein R$^2$ is hydrogen, halogen, —CN, C1-C8 optionally substituted alkyl, C3-C8 optionally substituted cycloallyl, —OR$^8$ (R$^8$ is hydrogen or C1-C8 optionally substituted alkyl), —NR$^9$R$^{10}$ (R$^9$ and R$^{10}$, which may be the same or different, hydrogen or C1-C8 optionally substituted alkyl), —C(=O)NR$^9$R$^{10}$ (R$^9$ and R$^{10}$, which may be the same or different, are hydrogen, C1-C8 optionally substituted alkyl, C3-C8 optionally substituted cycloalkyl, C6-C14 optionally substituted aryl or optionally substituted heterocyclyl), —NR$^9$C(=O)R$^{12}$ (R$^9$ is hydrogen or C1-C8 optionally substituted alkyl; R$^{12}$ is C1-C8 optionally substituted alkyl, C3-C8 optionally substituted cycloalkyl, C6-C14 optionally substituted aryl or optionally substituted heterocyclyl), —NR$^9$C(=O)OR$^{13}$ (R$^9$ is hydrogen or C1-C8 optionally substituted alkyl; R$^{13}$ is C1-C8 optionally substituted alkyl, C3-C8 optionally substituted cycloalkyl, C6-C14 optionally substituted aryl or optionally substituted heterocyclyl), —NR$^9$C(=)NR$^{13}$R$^{14}$ (R$^9$ and R$^{13}$, which may be the same or different, are hydrogen or C1-C8 optionally substituted alkyl; R$^{14}$ is C1-C8 optionally substituted alkyl, C3-C8 optionally substituted cycloalkyl, C6-C14 optionally substituted aryl or optionally substituted heterocyclyl), —NR$^9$SO$_2$R$^{13}$ (R$^9$ is hydrogen or C1-C8 optionally substituted alkyl; R$^{13}$ is C1-C8 optionally substituted alkyl, C3-C8 optionally substituted cycloalkyl, C6-C14 optionally substituted aryl or optionally substituted heterocyclyl), or —SR$^9$ (R$^9$ is hydrogen, C1-C8 optionally substituted alkyl, C3-C8 optionally substituted cycloalkyl, C6-C14 optionally substituted aryl or optionally substituted heterocyclyl).

(34) The compound as defined in (31) wherein $R^1$ and $R^2$ are hydrogen,

(35) The compound as defined in any one of (31) to (34) wherein $R^3$ is substituted phenyl [As substituents of phenyl may be mentioned 1 or 2 or more selected from the group consisting of halogen, —CN, —NO$_2$, C1-C8 optionally substituted alkyl, C3-C8 optionally substituted cylcoalkyl, C6-C14 optionally substituted aryl, optionally substituted heterocyclyl, —OR$^{16}$ ($R^{16}$ is hydrogen, C1-C8 optionally substituted alkyl, optionally substituted arylalkyl or optionally substituted heterocyclylalkyl), —NR$^{17}$R$^{18}$ ($R^{17}$ and $R^{18}$, which may be the same or different, are hydrogen or C1-C8 optionally substituted alkyl) and —C(=O)NR$^{17}$R$^{18}$ ($R^{17}$ and $R^{18}$, which may be the same or different, are hydrogen, C1-C8 optionally substituted aill, C3-C8 optionally substituted cycloalwkyl, C6-C14 optionally substituted aryl or optionally substituted heterocyclyl)], unsubstituted bicyclic heteroaryl, substituted bicyclic heteroaryl [As substituents of bicyclic heteroaryl may be mentioned 1 or 2 or more selected from the group consisting of halogen, —CN, —NO$_2$, C1-C8 optionally substituted alkyl, C6-C14 optionally substituted aryl, optionally substituted heterocyclyl, OR$^{16}$ ($R^{16}$ is hydrogen, C1-C8 optionally substituted alkyl, optionally substituted arylalkyl or optionally substituted heterocyclylalkyl), —NR$^{17}$R$^{18}$ ($R^{17}$ and $R^{18}$, which may be the same or different, are hydrogen or C1-C8 optionally substituted alkyl), —NHC(=O)R$^{19}$ ($R^{19}$ is C1-C8 optionally substituted alkyt, C3-C8 optionally substituted cycloalkyl, C6-C14 optionally substituted aryl or optionally substituted heterocyclyl) and —SR$^{17}$ ($R^{17}$ is C1-C8 optionally substituted aly)].

(36) The compound as defined in any one of (31) to (35) wherein $R^4$ is hydrogen, methyl or ethyl.

(37) The compound as defined in any one of (31) to (36) wherein $R^5$ is substituted cyclohexyl [As substituents of cyclohexyl may be mentioned 1 or 2 or more selected from the group consisting of halogen, C1-C8 optionally substituted alkyl —OH and —NH$_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, —OH and —NH$_2$].

(38) The compound as defined in any one of (31) to (37) wherein Y is —O—.

(39) The compound as defined in any one of (31) to (37) wherein Y is —S—.

(40) The compound as defined in any one of (31) to (39) wherein $R^{86}$ is tert-butyl or benzyl.

(41) The compound as defined in (31) wherein $R^1$ is hydrogen; $R^2$ is hydrogen; $R^3$ is substituted phenyl (As substituents of phenyl may be mentioned 1 or 2 or more selected from the group consisting of halogen, —CN, —OH, —OCH$_3$, —OEt, —COOH); $R^4$ is hydrogen or —CH$_3$; $R^5$ is 4-amino-cyclohexyl or piperidin-3-yl; Y is —O— or —S—; $R^{86}$ is tert-butyl;

(42) A composition comprising a compound as defined in any one of (1) to (30) in combination with a pharmaceutically acceptable carrier, diluent or excipient.

(43) A MAPKAP-K2 inhibitory agent containing a compound described in any one of Embodiments (1) to (30).

(44) A preventive drug or a therapeutic drug for a MAP-KAP-K2-mediated disease containing a compound described in any one of Embodiments (1) to (30).

(45) A preventive drug or a therapeutic drug according to Embodiment (44), wherein the disease is neurodegenerative/neurological disorders (including dementia), inflammatory disease, sepsis, autoimmune disease, destructive bone disorder, diabetes, cancer, ischemia reperfusion injury, angiogenic disorder, cachexia, obesity, angiogenesis, asthma and/or chronic obstructive pulmonary disease (COPD).

(46) A preventive drug or a therapeutic drug according to Embodiment (44), wherein the disease is inflammatory disease and/or autoimmune disease.

(47) A preventive drug or a therapeutic drug according to Embodiment (44), wherein the disease is autoimmune disease.

(51) A preventive drug or a therapeutic drug according to Embodiment (47), wherein the autoimmune disease is rheumatoid arthritis, psoriasis, ankylosing spondylitis, juvenile rheumatoid arthritis, psoriatic arthritis, graft-versus-host disease, diabetes or Crohn's disease.

BEST MODE FOR CARRYING OUT THE INVENTION

Figure 1:
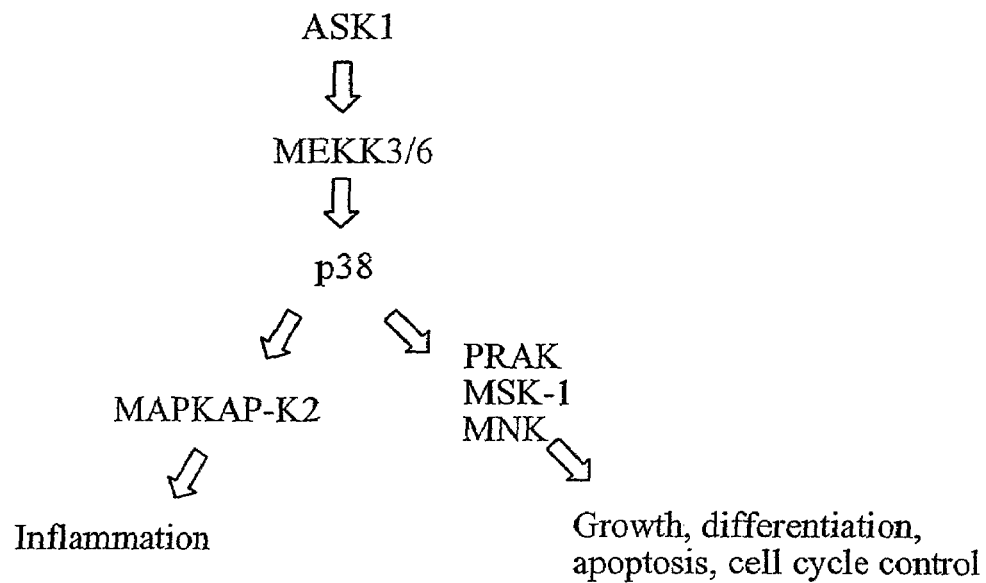
FIG. 1 shows a p38MAPK cascade.

In a first aspect the invention provides a compound of formula (I) and pharmaceutically acceptable salts, and other pharmaceutically acceptable biohydrolyzable derivatives thereof, including esters, amides, carbamates, carbonates, ureides, solvates, hydrates, affiity reagents or prodrugs:

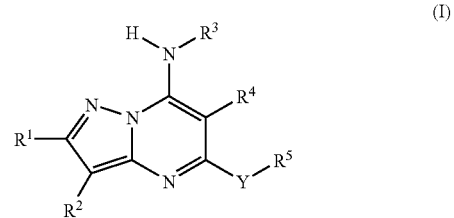

(I)

wherein
$R^1$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylailyl;

$R^2$ is hydrogen, halogen, —CN, —NO$_2$, —CHO, -G-R$^7$ [G is a single bond, —C(=O)— or —O—C(=O)—; and $R^7$ is C1-C8 optionally substituted alkyl, C2-C8 optionally substituted alkenyl, C2-C8 optionally substituted alkynyl, C3-C8 optionally substituted cycloalkyl, optionally substituted arylalkyl, optionally substituted heterocyclylaliyl, optionally substituted arylalkenyl, optionally substituted heterocyclylalkenyl, optionally substituted arylalkynyl, optionally substituted heterocyclylalkynyl, —OR$^8$ ($R^8$ is hydrogen, C1-C8 optionally substituted alkyl, C3-C8 optionally substituted cycloalkyl, C6-C14 optionally substituted aryl, optionally substituted hete ocyclyl, optionally substituted arylalkyl or optionally substituted heterocyclylalkyl), —NR$^9$R$^{10}$ ($R^9$ is as defined for $R^8$; $R^{10}$ is hydrogen, C1-8 optionally substituted alkyl, C3-C8 optionally substituted cycloalkyl, C6-C14 optionally substituted aryl, optionally substituted heterocyclyl, optionally substituted aylalkyl, optionally substituted heterocyclylalkyl or —OCH$_3$), —R$^{11}$ (R$^{11}$ is an optionally substituted saturated heterocyclyl with 5 to 7 members containing one to four heteroatoms selected from N, O and S), C6-C14 optionally substituted aryl or optionally substituted heteroaryl; provided that when R$^7$ is C6-C14 optionally substituted aryl or optionally substituted heteroaryl, then G is not a bond], —NR$^9$C(=O)R$^{12}$ (R$^9$ is as defined for R$^8$; R$^{12}$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl), —NR$^9$C(=X)OR$^{13}$ (R$^9$ and R$^{13}$, which may be the same or different, are as defined for R$^8$; X is O, S, N—CN or NH), —NR$^9$C(=X)NR$^{13}$R$^{14}$ (R$^9$, R$^{13}$ and R$^{14}$ which may be the same or different, are as defined for R$^8$; X is O, S, N—CN or NH), —NR$^9$SO$_2$R$^{13}$ (R$^9$ and R$^{13}$, which may be the same or different, are as defined for R$^8$) or —SR$^9$ (le is as defined for R$^8$);

R$^3$ is C1-C8 optionally substituted alkl, C2-C8 optionally substituted alkenyl, C2-C8 optionally substituted alkynyl, C3-C8 optionally substituted cycloalkyl, C6-C14 unsubstituted aryl, C6-C14 substituted aryl (As substituents of C6-C14 aryl may be mentioned 1 or 2 or more selected from the group consisting of halogen, —CN, —NO$_2$, —CHO, G—R$^{15}$ {G is a single bond, —C(=O)— or —O—C(=O)—; R$^{15}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{16}$ (R$^{16}$ is as defined for R$^8$) or —NR$^{17}$R$^{18}$ (R$^{17}$ and R$^{18}$, which may be the same or different, are as defined for R$^8$)}, —NR$^{17}$C(=O)R$^{19}$ (R$^{17}$ is as defined for R$^8$; R$^{19}$ is as defined for R$^{12}$), —NR$^{17}$C(=X)OR$^{18}$ (R$^{17}$ and R$^{18}$, which may be the same or different, are as defined for R$^8$; X is O, S, N—CN or NH), —NR$^{17}$C(=X)NR$^{18}$R$^{20}$ (R$^{17}$, R$^{18}$ and R$^{20}$, which may be the same or different, are as defined for R$^8$; X is O, S, N—CN or NH), —NR$^{17}$SO$_2$R$^{18}$ (R$^{17}$ and R$^{18}$, which may be the same or different, are as defined for R$^8$), —S(O)$_m$R$^{17}$ (R$^{17}$ is as defined for R$^8$; m is 0, 1 or 2) and —SO$_2$NR$^{21}$R$^{22}$ (R$^{21}$ and R$^{22}$, which may be the same or different, are as defined for R$^8$; R$^{21}$ and R$^{22}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with 1 or 2 or more substituents)], unsubstituted heterocyclyl, substituted heterocyclyl [As substituents of heterocyclyl may be mentioned 1 or 2 or more selected from the group consisting of halogen, —CN, —NO$_2$, —CHO, -G-R$^{23}$ {G is a single bond, —C(=O)— or —O—C(=O)—; R$^{23}$ is as defined for R$^{15}$}, —NR$^{24}$C(=O)R$^{25}$ (R$^{24}$ is as defined for R$^8$(; R$^{25}$ is as defined for R$^{12}$), —NR$^{24}$C(=X)OR$^{26}$ (R$^{24}$ and R$^{26}$, which may be the same or different, are as defined for R$^8$; X is O, S, N—CN or NH), —NR$^{24}$C(=X)NR$^{26}$R$^{27}$ (R$^{24}$, R$^{26}$ and R$^{27}$, which may be the same or different, are as defined for R$^8$; X is O, S, N—CN or NH), —NR$^{24}$SO$_2$R$^{26}$ (wherein R$^{24}$ and R$^{26}$, which may be the same or different, are as defined for R$^8$), —S(O)$_m$R$^{24}$ (R$^{24}$ is as defined for R$^8$; m is 0, 1 or 2) and —SO$_2$NR$^{28}$R$^{29}$ (R$^{28}$ and R$^{29}$, which may be the same or different, are as defined for R$^8$; R$^{28}$ and R$^{29}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with 1 or 2 or more substituents)], optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

R$^4$ is hydrogen, halogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{30}$ (R$^{30}$ is as defined for R$^8$), —SR$^{30}$ (R$^{30}$ is as defined for R$^8$), —NR$^{30}$R$^{31}$ (R$^{30}$ and R$^{31}$, which may be the same or different, are as defined for R$^8$), —NR$^{30}$C(=O)R$^{32}$ (R$^{30}$ is as defined for R$^8$; and R$^{32}$ is as defined for R$^{12}$), —NR$^{30}$C(=X)OR$^{31}$ (R$^{30}$ and R$^{31}$, which may be the same or different, are as defined R$^8$; X is O, S, N—CN or NH), —NR$^{30}$C(=X)NR$^{31}$R$^{33}$ (R$^{30}$, R$^{31}$ and R$^{33}$, which may be the same or different, are as defined for R$^8$; X is O, S, N—CN or NH) or —NR$^{30}$SO$_2$R$^{31}$ (R$^{30}$ and R$^{31}$, which may be the same or different, are as defined for R$^8$);

R$^5$ is C1-C8 substituted alkyl, C2-C8 optionally substituted alkenyl, C2-C8 optionally substituted alkynyl, C3-C8 substituted cycloalkyl [As substituents of C3-C8 cycloalkyl may be mentioned 1 or 2 or more selected from the group consisting of halogen, —CN, —NO$_2$, —CHO, =O, -G-R$^{34}$ {G is a single bond, —C(=O)— or —O—C(=O)—; R$^{34}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{35}$ (R$^{35}$ is as defined for R$^8$) or —NR$^{36}$R$^{37}$ (R$^{36}$ and R$^{37}$, which may be the same or different, are as defined for R$^8$)}, —NR$^{38}$C(=C)R$^{39}$ (R$^{38}$ is as defined for R$^8$; R$^{39}$ is as defined for R$^{12}$), —NR$^{38}$C(=X)OR$^{40}$ (R$^{38}$ and R$^{40}$, which may be the same or different, are as defined for R$^8$; X is O, S, N—CN or NH), —NR$^{38}$C(=X)NR$^{40}$R$^{41}$ (R$^{38}$, R$^{40}$ and R$^{41}$, which may be the same or different, are as defined for R$^8$; X is O, S, N—CN or NH) and —NR$^{38}$SO$_2$R$^{40}$ (R$^{38}$ and R$^{40}$, which may be the same or different, are as defined for R$^8$)], unsubstituted heterocyclyl, substituted heterocyclyl [As substituents of heterocyclyl may be mentioned 1 or 2 or more selected from the group consisting of halogen, —CN, —NO$_2$, —CHO, =O, -G-R$^{42}$ {G is a single bond, —C(=O)— or —O—C(=O)—; R$^{42}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkyny, —OR$^{43}$ (R$^{43}$ is as defined for R$^8$) or —NR$^{44}$R$^{45}$ (R$^{44}$ and R$^{45}$, which may be the same or different, are as defined for R⁸)}, —NR⁴⁶C(=O)R⁴⁷ (R⁴⁶ is as defined for R⁸; R⁴⁷ is as defined for R¹²), —N⁴⁶C(=X)OR⁴⁸ (R⁴⁶ and R⁴⁸, which may be the same or different, are as defined for R⁸; X is O, S, N—CN or NH), —NR⁴⁶C(=X)NR⁴⁸R⁴⁹ (R⁴⁶, R⁴⁸ and R⁴⁹, which may be the same or different, are as defined for R⁸; X is O, S, N—CN or NH) and —N⁴⁶SO₂R⁴⁸ (R⁴⁶ and R⁴⁸, which may be the same or different, are as defined for R⁸)], optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

Y is —O— or —S—;

provided that $R^5$ is not C1-C6 alkyl which is unsubstituted or substituted (with 1 or 2 or more phenyls or halogens).

For the purposes of this invention, "alkyl" relates to both straight chain or branched alkyl radicals of 1 to 8 carbon atoms including, but not limited to, methyl, ethyl, n-propyl, isopropyl, n-butyl, sec-butyl, isobutyl, tert-butyl, n-pentyl, isopentyl, neopentyl, tert-pentyl, 2-methylpentyl, 4-methylpentyl, 1-ethylbutyl, n-hexyl, n-heptyl, 2-methylhexyl, 5-methylhexyl, 1,1-dimethylpentyl, 6-methylheptyl and n-octyl, The term "cycloalkyl" means a cycloalkyl radical of 3 to 8 carbon atoms including, but is not limited to, cyclopropyl, cyclobutyl, cyclopentyl, cyclohexyl, cycloheptyl and cyclooctyl.

The term "alkenyl" means a straight chain, branched or ring structured alkenyl radical of 2 to 8 carbon atoms and containing 1 or 2 or more carbon-carbon double bonds and includes, but is not limited to, vinyl, allyl, isopropenyl, 1-propenyl, 2-butenyl, 1-butenyl, 2-methyl-1-propenyl, 2-methyl-3-pentenyl, 1-pentenyl, 2-pentenyl, 4-methyl-1-pentenyl, 1-hexenyl, 2-hexenyl, 2-cyclopentenyl, 2-cyclohexenyl, 2-heptenyl, 2-octenyl, 3-cyclopentenyl, 1,3-butadienyl and 1,5-hexadienyl. When they have cis and trans geometrical isomers, both isomers are included.

The term "alkynyl" means a straight chain or branched alkynyl radical of 2 to 8 carbon atoms and containing 1 or 2 or more carbon-carbon triple bonds and includes, but is not limited to, ethynyl, 2-propynyl, 1-propynyl, 1-butynyl, 2-butynyl, 3-hexynyl, 3-methyl-1-butynyl, 3,3-dimethyl-1-butynyl, 3-pentynyl, 2-pentynyl, 2-hexynyl, 3-hexynyl, 4-hexynyl, 1-methyl-3-pentynyl, 1-methyl-3-hexynyl, 2-heptynyl and 2-octynyl.

"Aryl" means an aromatic 6 to 10 membered hydrocarbon containing one ring or being fused to 1 or 2 or more saturated or unsaturated rings including, but not limited to, phenyl, naphthyl, anthracenyl, 5-indanyl and 5,6,7,8-tetrahydro-2-naphthyl.

The term "heteroaryl" refers to an aromatic 5-to 10-membered heterocyclic ring which contains 1 to 4 heteroatoms selected from N, O or S, or an aromatic 5- to 10-membered heterocyclic ring fused with 1 or 2 or more saturated or unsaturated rings. Examples of the heteroaryl include, but not limited to, furan, thiophene, pyrrole, oxazole, isoxazole, thiazole, isothiazole, imidazole, pyrazole, triazole, thiadiazole, oxadiazole, tetrazole, pyridine, pyrazine, pyrimidine, pyridazine, benzofuran, dibenzofuran, benzothiophene, indole, indazole, berminidazole, benzothiazole, benzoxazole, quinoline, isoquinoline, quinazoline, quinoxaline, purine, pteridine and phenoxazine.

The term "bicyclic heteroaryl" refers to an aromatic heterocycle in which a 5- to 10-membered aromatic heterocycle containing 1 to 4 heteroatoms selected from N, O or S is fused with a 5-to 10-membered saturated or unsaturated ring. Examples of bicyclic heteroaryl include, but not limited to, benzofuran, dibenzofuran, benzothiophene, indole, indazole, benzimidazole, benzothiazole, benzoxazole, quinoline, isoquinoline, quinazoline, quinoxaline, purine, pteridine and phenoxazine.

"Saturated heterocyclyl" means a 3 to 10-membered saturated ring containing 1 to 4 heteroatoms selected from N, O or S and containing one ring or being fused to 1 or 2 or more saturated rings; the saturated heterocyclyl is fully saturated. Examples of saturated heterocyclyl include, but are not limited to, monovalent group including piperidine, piperazine, morpholine, pyrrolidine, imidazolidine, pyrazolidine and quinuclidine.

"Heterocyclyl" means a 3 to 10-membered ring system containing 1 to 4 heteroatoms selected from N, O or S. The heterocyclyl system can contain one ring or may be fused to 1 or 2 or more saturated or unsaturated rings; the heterocyclyl can be fully saturated, partially saturated or unsaturated and includes, but is not limited to, heteroaryl and saturated heterocyclyl; the heterocyclyl can contain one or two —(C=O)— or —(C=S)— groups. Examples of heterocyclyl include, but are not limited to, monovalent group including furan, thiophene, pyrrole, pyrroline, pyrrolidine, oxazole, oxazolidine, isoxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, benzimidazole, benzothiazole, benzoxazole, chromane, isochromane, quinoline, decahydroquinoline, isoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine, quinuclidine, acridine, carbazole, cinnoline, dioxane, dioxolane, dithiane, dithiazine, dithiazole, dithiolane, indolizine, indazole, isoindole, isoxazole, napthyridine, oxathiazole, oxathiazolidine, oxazine, oxadiazine, phthalazine, quinolizine, tetrahydrofuran, tetrazine, thiadiazine, thiatriazole, thiazine, thianaphthalene, triazine, 1,3-dioxane, 2,5-dihydrofiran, oxazoline, trithiane, piperidin-2-one, 3H-isobenzofiran-1-one, epsilon-caprolactam, 2-furanone, 2-pyrrolidone, tetrahydro-3H-pyrazol-3-one, piperazin-2-one, coumarin, tetrahydro-2-pyrimidinone, glutarimide and morpholine-3,5-dione.

"Arylalkyl" used herein is a group comprising a combination of the aryl and the alkyl. Examples thereof include, but are not limited to, benzyl, phenethyl, (2-naphthyl)-methyl, 3-phenylpropyl, 4-phenylbutyl and 5-(1-naphthyl) pentyl.

"Heterocyclylalkyl" used herein is a group comprising a combination of the heterocyclyl and the alkyl. Examples thereof include, but are not limited to, 2-pyridylmethyl, 3-pyridylmethyl, 4-pyridylmethyl, 3-furilmethyl, 3-thienylmethyl, 2-(3-indolyl)ethyl, 2-morpholinoethyl, 2-piperidinoethyl, 2-(4-pyridyl)-ethyl, 3-(1-piperadinyl)-propyl, 3-(2-thienyl)-propyl, and 2-(1-imidazole)ethyl.

"Arylalkenyl" used herein is a group comprising a combination of the aryl and the alkenyl. Examples thereof include, but are not limited to, styryl, cinnamyl and 4-phenyl-2-butenyl. When they have cis and trans geometrical isomers, both isomers are included.

"Heterocyclylalkenyl" used herein is a group comprising a combination of the heterocyclyl and the alkenyl. Examples thereof include, but are not limited to, (3-pyridyl)vinyl, 3-(3-thienyl)propene-2-yl, 3-(4-morpholinyl)-1-propenyl and 4-(1-piperidyl)-2-butenyl. When they have cis and trans geometrical isomers, both isomers are included.

"Arylalkynyl" used herein is a group comprising a combination of the aryl and the alkynyl. Examples thereof include, but are not limited to, phenylethynyl and 4-phenyl-2-butynyl.

"Heterocyclylalkynyl" used herein is a group comprising a combination of the heterocyclyl and the alkynyl. Examples thereof include, but are not limited to, 4-(4-pyridyl)-2-butynyl and 5-(1-piperazinyl)-2-pentynyl.

Halogen means F, Cl, Br or I.

In the compounds according to the present invention, suitable substituents include, unless otherwise specified, F, Cl, Br, I, —CN, —NO$_2$, —CHO, =O, -G-R$^{50}$ {G is a bond, —C(=O)—, or O—C(—O)—; R$^{50}$ is optionally substituted C1-C8 alkyl, optionally substituted C2-C8 alkenyl, optionally substituted C2-C8 alkynyl, optionally substituted C3-C8 cycloalkyl, optionally substituted C6-C14 aryl, optionally substituted heterocyclyl, —OR$^{51}$ or —NR$^{52}$R$^{53}$}, —NR$^{54}$C(=O))R$^{55}$, —NR$^{54}$C(=X)OR$^{55}$ (X is O, S, N—CN, or NH), —NR$^{54}$C(=X)N$^{55}$R$^{56}$(X is O, S, N—CN, or NH), —NR$^{54}$SO$_2$R$^{55}$, —S(O)$_m$R$^{54}$, —SR$^{54}$ or —SO$_2$NR$^{54}$R$^{55}$; wherein optionally substituted C1-8 aLkyl means C1-8 alkyl which may be optionally substituted with 1 or 2 or more substituents selected from the group consisting of F, Cl, Br, I, —CN, —NO$_2$, —CHO, heterocyclyl, —OR$^{56}$, —NR$^{57}$R$^{57}$R$^{58}$, —NR$^{59}$C(=O)R$^{60}$, —COOR$^{59}$, —CONR$^{59}$R$^{60}$ and —S(O)$_m$R$^{59}$;

wherein optionally substituted C2-C8 alkenyl means C2-C8 alkenyl which may be optionally substituted with 1 or 2 or more substituents selected from the group consisting of F, Cl, Br, I, —CN, —NO$_2$, —CHO, heterocyclyl, —OR$^{61}$, —NR$^{62}$R$^{63}$, —NR$^{6r0}$C(=O)R$^{65}$, —COOR$^{64}$, —CONR$^{64}$R$^{65}$ and —S(O)R$^{64}$;

wherein optionally substituted C2-C8 alkynyl means C2-C8 alkynyl which may be optionally substituted with 1 or 2 or more substituents selected from the group consisting of F, Cl, Br, I, —CN, —NO$_2$, —CHO, heterocyclyl, —OR$^{66}$, —NR$^{67}$R$^{68}$, —NR$^{69}$C(=O)R$^{70}$, —COOR$^{69}$. —CONR$^{69}$R$^{70}$ and —S(O)$_m$R$^{69}$;

wherein optionally substituted C3-C8 cycloalkyl means C3-C8 cycloalkyl which may be optionally substituted with 1 or 2 or more substituents selected from the group consisting of F, Cl, Br, I, —CN, —NO$_2$, —CHO, heterocyclyl, —OR$^{71}$, —NR$^{72}$R$^{73}$ —NR$^{74}$C(=O)R$^{75}$, —COOR$^{74}$, —CONR$^{74}$R$^{75}$ and —S(O)$_m$R$^{74}$;

wherein optionally substituted C6-C14 aryl means C6-C14 aryl which may be optionally substituted with 1 or 2 or more substituents selected from the group consisting of F, Cl, Br, I, —CN, —NO$_2$, —CHO, heterocyclyl, OR$^{76}$, —NR$^{77}$R$^{78}$, —NR$^{79}$C(=O)R$^{80}$, —COOR$^{79}$, —CONR$^{79}$R$^{80}$ and —S(O)$_m$ R$^{79}$;

wherein optionally substituted heterocyclyl means heterocyclyl which may be optionally substituted with 1 or 2 or more substituents selected from the group consisting of F, Cl, Br, I, —CN, —NO$_2$, —CHO, heterocyclyl, —OR$^{81}$, —NR$^{82}$R$^{83}$, —NR$^{84}$C(=O)R$^{85}$, —COOR$^{84}$, —CONR$^{84}$R$^{85}$ and —S(O)$_m$ R$^{84}$;

R$^{51}$ to R$^{85}$, which may be the same or different, are hydrogen, C1-8 alkyl, C3-C8 cycloalkyl, C6-C14 aryl, heterocyclyl, arylalkyl or heterocyclylalkyl; m=0, 1 or 2.

R$^1$ is preferably hydrogen or C1-C8 optionally substituted alkyl, and more preferably C1-C6 optionally substituted alkyl. More preferably R$^1$ is hydrogen.

R$^2$ is preferably selected from hydrogen, halogen, —CN, C1-C8 optionally substituted alkyl, C3-C8 optionally substituted cycloalkyl, —OR$^8$ (R$^8$ is hydrogen or C1-8 optionally substituted alkyl), —NR?R$^{10}$ (R$^9$ and R$^{10}$, which may be the same or different, hydrogen or C1-8 optionally substituted alkyl), —C(=O)NR$^9$R$^{10}$ (R$^9$ and R$^{10}$, which may be the same or different, are hydrogen, C1-C8 optionally substituted alkyl, C3-C8 optionally substituted cycloalkyl, C6-C14 optionally substituted aryl or optionally substituted heterocyclyl), —NR$^9$C(=O)R$^{12}$ (R$^9$ is hydrogen or C1-C8 optionally substituted alkyl; R$^{12}$ is C1-C8 optionally substituted alkyl, C3-C8 optionally substituted cycloalkyl, C6-C14 optionally substituted aryl or optionally substituted heterocyclyl), —NR$^9$C(=O)OR$^{13}$ (R$^9$ is hydrogen or C1-C8 optionally substituted alkyl;

R$^{13}$ is C1-C8 optionally substituted alkyl, C3-C8 optionally substituted cycloalkyl, C6-C14 optionally substituted aryl or optionally substituted heterocyclyl), —NR$^9$C(=O)NR$^{13}$R$^{14}$ (R$^9$ and R$^{13}$, which may be the same or different, are hydrogen or C1-C8 optionally substituted alkyl; R$^{14}$ is C1-C8 optionally substituted alkyl, C3-C8 optionally substituted cycloalkyl, C6-C14 optionally substituted aryl or optionally substituted heterocyclyl), —NR$^9$SO$_2$R$^{13}$ (R$^9$ is hydrogen or C1-C8 optionally substituted alkyl; R$^{13}$ is C1-C8 optionally substituted alkyl, C3-C8 optionally substituted cycloalkyl, C6-C14 optionally substituted aryl or optionally substituted heterocyclyl) or —SR$^9$ (R$^9$ is hydrogen, C1-C8 optionally substituted alkyl, C3-C8 optionally substituted cycloalkyl, C6-C14 optionally substituted aryl or optionally substituted heterocyclyl).

More preferably R$^2$ is hydrogen, halogen, —CN, —SCH$_3$, C1-C8 optionally substituted alkyl, C3-C8 optionally substituted cycloalkyl. Further more is hydrogen, halogen, C1-C8 optionally substituted alkyl, C3-C8 optionally substituted cycloalkyl is preferable as R$^2$. Still more preferably R$^2$ is hydrogen;

R$^3$ is preferably selectedifrom substituted C6-C14 aryl [as substituents of C6-C14 aryl may be mentioned 1 or 2 or more substituents selected from the group consisting of halogen, —CN, —NO$_2$, -G-R$^{15}$ {G is a single bond or —C(=O)—; R$^{15}$ is optionally substituted C1-C8 alkyl, optionally substituted C2-C8 alkenyl, optionally substituted C2-C8 alkynyl, optionally substituted C3-C8 cycloalkyl, optionally substituted C6-C14 aryl, optionally substituted heterocyclyl, —OR$^{16}$ (R$^{16}$ is hydrogen, optionally substituted C1-C8 alkyl, optionally substituted arylalkyl or optionally substituted heterocyclylalkyl) or —NR$^{17}$R$^{18}$ (R$^{17}$ and R$^{18}$ may be the same or different and represent hydrogen, optionally substituted C1-C8 alkyl, optionally substituted C3-C8 cycloalkyl, optionally substituted C6-C14 aryl or optionally substituted heterocyclyi)}, —NR$^{17}$C(=O)R$^{19}$ (R$^{17}$ is hydrogen or optionally substituted C1-C8 alkyl; R$^{19}$ is optionally substituted C1-C8 alkyl, optionally substituted C3-C8 cycloalkyl, optionally substituted C6-C14 aryl or optionally substituted heterocyclyl) and —S(O)$_m$R$^{17}$ (R$^{17}$ is optionally substituted C1-C8 alkyl or optionally substituted C3-C8 cycloalkyl; m is 0 or 2)], unsubstituted heterocyclyl, substituted heterocyclyl [as substituents of heterocyclyl may be mentioned 1 or 2 or more substituents selected from the group consisting of halogen, —CN, —NO$_2$, -G-R$^{23}$ {G is a single bond or —C(=O)—; R$^{23}$ is optionally substituted C1-C8 alkyl, optionally substituted C3-C8 cycloalkyl, optionally substituted C6-C14 aryl, optionally substituted heterocyclyl, —OR$^{16}$ (R$^{16}$ is hydrogen, optionally substituted C1-C8 alkyl, optionally substituted C3-C8 cycloalkyl, optionally substituted C6-C14 aryl or optionally substituted heterocyclyl) or —NR$^{17}$R$^{18}$ (R$^{17}$ and R$^{18}$ may be the same or different and represent hydrogen, optionally substituted C1-C8 alkyl, optionally substituted C3-C8 cycloalkyl, optionally substituted C6-C14 aryl or optionally substituted heterocyclyl)}, —NR$^{24}$C(=O)R$^{25}$ (R$^{24}$ is hydrogen or optionally substituted C1-C8 alkyl; R$^{25}$ is optionally substituted C1-C8 adkyl, optionally substituted C3-C8 cycloalkyl, optionally substituted C6-C14 aryl or optionally substituted heterocyclyl), —S(O)$_m$R$^{24}$ (R$^{24}$ is optionally substituted C1-C8 alkyl or optionally substituted C3-C8 cycloalkyl; m is 0 or 2) and —SO$_2$NR$^{28}$NR$^{29}$ (R$^{28}$ and R$^{29}$ are as defined in Embodiment (1)].

More preferably R$^3$ is substituted C6-C14 aryl [as substituents of C6-C14 aryl may be mentioned 1 or 2 or more substituents selected from the group consisting of halogen, —CN, -G-R$^{15}$ {G is as defined in Embodiment (1); R$^{15}$ is as defined in Embodiment (1)}], unsubstituted heterocyclyl and substituted heterocyclyl [as substituents of heterocyclyl may be mentioned 1 or 2 or more substituents selected from the group consisting of halogen, —CN, -G-R$^{23}$ {G is as defined in Embodiment (1); R$^{23}$ is as defined in Embodiment (1)}, —NR$^{24}$C(=O)R$^{25}$ (R$^{24}$ and R$^{25}$ are as defined in Embodiment (1)), —S(O)$_m$R$^{24}$ (R$^{24}$ is as defined in Embodiment (1); m is as defined in Embodiment (1)) and —SO$_2$NR$^{28}$R$^{29}$ (R$^{28}$ and R$^{29}$ are as defined in Embodiment (1)].

Still more preferably, R13 is substituted C6-C14 aryl [as substituents of C6-C14 aryl, 1 or 2 or more substituents are selected from the group consisting of halogen, —CN, -G-R$^{15}$ {G is as defined in Embodiment (1); R$^{15}$ is as defined in Embodiment (1)}], unsubstituted heteroaryl and substituted heteroaryl [as substituents of substituted heteroaryl may be mentioned 1 or 2 or more substituents selected from the group consisting of halogen, —CN, -G-R$^{23}$ {G is as defined in Embodiment (1); (R$^{23}$ is as defined in Embodiment (1)}, —NR$^{24}$C(=O)R$^{25}$(R$^{24}$ and R$^{25}$ are as defined in Embodiment (1)), —S(O)$_m$R$^{24}$ (R$^{24}$ is as defined in Embodiment (1); m is as defined in Embodiment (1)) and —SO$_2$NR$^{28}$R$^{29}$ (R$^{28}$ and R$^{29}$ are as defined in Embodiment (1))].

Of the above substituents, in the case where R$^3$ is substituted C6-C14 aryl, as substituents of C6-C14 aryl, 1 or 2 or more substituents are preferably selected from the group consisting of halogen, —CN, -G-R$^{23}$ {G is a single bond or —C(=O)—; R$^{15}$ is optionally substituted C1-C8 alkyl, optionally substituted C3-C8 cycloalkyl, optionally substituted C6-C14 aryl, optionally substituted heterocyclyl, optionally substituted arylalkyl, optionally substituted heterocyclylalkyl, OR$^{16}$ or —NR$^{17}$R$^{18}$}, —NR$^{17}$C(=O)R$^{19}$, —NR$^{17}$SO$_2$R$^{18}$ and —SO$_2$NR$^{21}$R$^{22}$ (R$^{16}$, R$^{17}$, R$^{18}$, R$^{19}$, R$^{21}$ and R$^{22}$ are as defined in Embodiment (1)).

Still irther preferably, R$^3$ is substituted C6-C 14 aryl [as substituents of C6-C 14 aryl, 1 or 2 or more substituents are selected from the group consisting of halogen, —CN, -G-R$^{15}$ {G is a single bond; R$^{15}$ is optionally substituted C6-C14 aryl, optionally substituted heterocyclyl, optionally substituted arylalkyl, optionally substituted heterocyclylalkyl, —OR$^{16}$ or —NR$^{17}$R$^{18}$}, —NR$^{17}$C(=O)R$^{19}$, —NR$^{17}$SO$_2$R$^{18}$ and —SO$_2$NR$^{21}$R$^{22}$ (R$^{16}$, R$^{17}$, R$^{18}$, R$^{19}$, R$^{21}$ and R$^{22}$ are as defined in Embodiment (1)] or R$^3$ is substituted aryl [as substituents of C6-C14 aryl may be mentioned 1 or 2 or more substituents selected from the group consisting of halogen, —CN, -G-R$^{15}$ {G is —C(=O)—; R$^{15}$ is optionally substituted C1-C8 aqlyl, optionally substituted C3-C8 cycloalkyl, —OR$^{16}$ or—NR$^{17}$R$^{18}$}, (R$^{16}$, R$^{17}$ and R$^{18}$ are as defined in Embodiment (1)].

More preferably, substituted C6-C14 aryls in this case include substituted phenyl {as substituents of phenyl, 1 or 2 or more substituents are selected from the group consisting of R$^{15}$ (R$^{15}$ is optionally substituted C6-C14 aryl), R$^{16}$ (R$^{16}$ is as defined in Embodiment (1)), —NR$^{17}$C(=O)R$^{19}$ (R$^{17}$ and R$^{19}$ are as defined in Embodiment (1)) and —C(=O)NR$^{17}$R$^{18}$ (R$^{17}$ and R$^{18}$ are as defined in Embodiment (1)}, specifically including 4-ethoxyphenyl, 4-(2-methoxyethoxy)phenyl, 4-(2-isopropoxyethoxy)phenyl, 4-(2-cyclohexylethoxy)phenyl, 4-benzyloxyphenyl, 4-(2-benzyloxyethoxy)phenyl, 4-(2-morpholinoethyl)phenyl, 4-(2-pyridylmethoxy)phenyl, 4-{2-(2-pyridyl)ethoxy}phenyl, 3-carbamoylphenyl, 3-(N-methylcarbamoyl)phenyl, 4-(N-methylcarbamoyl)phenyl, 4-{N-(2,2,2-trifluoroethyl)carbamoyl}phenyl, 3-{N-(2-methylthio)ethylcarbamoyl}phenyl, 4-{N-(2-methylthio)ethylcarbamoyl}phenyl, 4-{N-(2,2-dimethylpropyl)carbamoyl}phenyl, 4-N-cyclopropylcarbamoyl)phenyl, 4-(N-cyclopentylcarbamoyl)phenyl, 4-(N-cyclohexylmethylcarbamoyl)phenyl, 4-(N-tetrahydrofurfurycarbamoyl)phenyl, 4-{N-(3-pyridylmethyl)carbamoyl}phenyl, 4-{N-(4-pyridylmethyl)carbamoyl}phenyl, 4-{N-(4-methoxyphenyl)carbamoyl}phenyl, 4-{N-(4-fluorophenyl)carbamoyl}phenyl, 4-{N-(2-dimethylaminoethyl)carbamoyl}phenyl, 4-{N-(2-morpholinoethyl)carbamoyl}phenyl, 4-[N-{2-(1-pyrrolidinyl)ethyl}carbamoyl]phenyl, 4-{N-(carbamoylmethyl)carbamoyl}phenyl, 4-{N-(4-indolyl)carbamoyl}phenyl, 4-{N-(5-indolyl)carbamoyl}phenyl, 4-{N-(6-indolyl)carbamoyl}phenyl, 4-acetamidophenyl, 4-methoxyacetamidophenyl, 4-(3-methylthiopropionyl)aminophenyl, 4-(4-methoxybenzoylamino)phenyl, 4-(4-cyanobenzoylamino)phenyl, 4-(3-pyridinecarbonylamino)phenyl, 4-(4-pyridinecarbonylamino)phenyl and the like. Still more preferably, the substituted C6-C14 aryl includes 4-ethoxyphenyl, 4-(2-methoxyethoxy)phenyl and the like.

In addition, in the case where R$^3$ is unsubstituted heteroaryl or substituted heteroaryl, preferably heteroaryl is unsubstituted bicyclic heteroaryl or substituted bicyclic heteroaryl [substituents of bicyclic heteroaryl are 1 or 2 or more substituents selected from halogen, —CN, -G-R$^{23}$ {G is as defined in Embodiment (1); R$^{23}$ is as defined in Embodiment (1)}, —NR$^{24}$C(=)R$^{25}$ (R$^{24}$ and R$^{25}$ are as defined in Embodiment (1)), —S(O)$_2$R$^{24}$ (R$^{28}$ is as defined in Embodiment (1)) and —SO$_2$R$^{28}$R$^{29}$ (R$^{28}$ and R$^{29}$ are as defmed in Embodiment (1)].

Still more preferably, R$^3$ is unsubstituted bicyclic heteroaryl or substituted bicyclic heteroaryl {substituents of bicyclic heteroaryl are R$^{23}$ (R$^{23}$ is as defined in Embodiment (1)) and —SR$^{24}$ (R$^{24}$ is as defined in Embodiment (1))}.

In this case, bicyclic heteroaryls include preferably benzoxazolyl, benzoitiazolyl, benzimidazolyl, indole, 1H-indazolyl and indolinyl, and specifically include benzoxazol-6-yl, 2-methylbenzoxazol-5-yl, 2-methylbenzoxazol-6-yl, 2-methylbenzothiazol-5-yl 2-methylbenzothiazol-6-yl, 2-methylthiobenzothiazol-6-yl, 2-isopropylthiobenzothiazol-6-yl, 2-(2-methoxyethyl)benzothiazol-6-yl, 1-methylbenzimidazol-5-yl, 1-methylindol-5-yl, 1-(2-methoxyethyl)indol-5-yl, 1H-indazol-6-yl, 1-methyl-1H-indazol-5-yl, 1-(2-methoxyethyl) 1H-indazol-5-yl, 1-(2-methylthioethyl)-1H-indazol-5-yl, 1-(2-morpholinoethyl)-1H-indazol-5-yl, 2-oxo-5-indolinyl and the like. More preferably, the bicyclic heteroaryl includes 2-methylbenzoxazol-6-yl, 2-methylbenzothiazol-6-yl, 2-methylthiobenzothiazol-6-yl and the like.

R$^4$ is preferably selected from hydrogen, halogen, C1-C8 optionally substituted alkyl, C2-C8 optionally substituted alkenyl and C3-C8 optionally substituted cycloalkyl. More preferably R$^4$ is hydrogen or C1-C8 optionally substituted alkyl, fer preferably R$^4$ is hydrogen, methyl or ethyl.

R$^5$ is preferably optionally substituted C1-C8 alkyl, substituted C3-C8 cycloalkyl [as substituents of C3-C8 cycloalkyl may be mentioned those described in Embodiment (1)], unsubstituted heterocyclyl, substituted heterocyclyl [as substituents of heterocyclyl may be mentioned those described in Embodiment (1)].

More preferably, R$^5$ is substituted C3-C8 cycloalkyl [as substituents of C3-C8 cycloalkyl may be mentioned 1 or 2 or more substituents selected from the group consisting of halogen, —CN, =O, -G-R$^{34}$ {G is a single bond; R$^{34}$ is optionally substituted C1-8 alkyl, optionally substituted C2-C8 alkenyl, and optionally substituted C3-C8 cycloalkyl or —NR$^{36}$R$^{37}$ are as defined in Embodiment (1))}], unsubstituted heterocyclyl, substituted heterocyclyl {as substituents of heterocyclyl may be mentioned 1 or 2 or more substituents selected from the group consisting of halogen, —CN, =O, optionally substituted C1-C8 alkyl, optionally substituted C2-C8 alkenyl, optionally substituted C3-C8 cycloalkyl and —NR$^{44}$R$^{45}$ (R$^{44}$ and R$^{45}$ are as defined in Embodiment (1))}.

Still more preferably, R$^5$ is substituted cyclohexyl [as substituents of cyclohexyl may be mentioned 1 or 2 or more substituents selected from the group consisting of halogen, —CN, =O, -G-R$^{34}$ {G is a single bond; R$^{34}$ is optionally substituted C1-C8 alkyl, optionally substituted C2-C8 alkenyl, and optionally substituted C3-C8 cycloalkyl or —N$^{36}$R$^{37}$ (R$^{36}$ and R$^{37}$ are as defined in Embodiment (1))}], unsubstituted piperidyl, substituted piperidyl (as substituents of piperidyl may be mentioned 1 or 2 or more substituents selected from the group consisting of halogen, —CN, optionally substituted C1-C8 alkyl, optionally substituted C2-C8 alkenyl and optionally substituted C3-C8 cycloalkyl), unsubstituted pyrrolidinyl and substituted pyrrolidinyl (as substituents of pyrrolidinyl may be mentioned 1 or 2 or more substituents selected from the group consisting of halogen, —CN, optionally substituted C1-C8 alkyl, optionally substituted C2-C8 alkenyl and optionally substituted C3-C8 cycloalkyl).

Further more preferably, R$^5$ is 4-arnino-cyclohexyl, piperidin-3-yl, piperidin-4-yl and pyrrolidin-3-yl.

Y is preferably O.

As preferred combinations of the groups mentioned as preferred examples of R$^1$—R$^5$ and Y in formula I according to the invention, there may be mentioned the following combinations 1) to 10).

1) In formula I, wherein R$^1$ is hydrogen, R$^2$ is hydrogen, R$^3$ is C6-C14 aryl group substituted by C6-C14 optionally substituted aryl or optionally substituted heterocyclyl [wherein C6-C14 aryl group as R$^3$ may be substituted by 1 or 2 or more substituents selected from the group consisting of halogen, —CN, C1-8 optionally substituted alkyl, —OR$^{16}$ (R$^{16}$ is hydrogen, C1-C8 optionally substituted alkyl), —NR$^{17}$R$^{18}$ (R$^{17}$ and R$^{18}$, which may be the same or different, are hydrogen or C1-C8 optionally substituted alkyl)], R$^4$ is C1-C8 optionally substituted alkyl, R$^5$ is cyclohexyl [As substituents of cyclohexyl may be mentioned 1 or 2 or more selected from the group consisting of halogen, C1-C8 optionally substituted alkyl, —OH, and —NH$_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, —OH, and —NH$_2$] and Y is —O—

2) In formula I, wherein R$^1$ is hydrogen, R$^2$ is hydrogen, R$^3$ is C6-C14 aryl group substituted by —OR$^{87}$ (R$^{87}$ is C1-C8 optionally substituted alkyl, optionally substituted arylalkyl or optionally substituted heterocyclylalkyl) [wherein C6-C14 aryl group as R$^3$ may be substituted by 1 or 2 or more substituents selected from the group consisting of halogen, —CN, C1-C8 optionally substituted alkyl, —OR$^{16}$ (R$^{16}$ is hydrogen, C1-C8 optionally substituted alkyl), —NR$^{17}$R$^{18}$ (R$^{17}$ and R$^{18}$, which may be the same or different, are hydrogen or C1-C8 optionally substituted alkyl)], R$^4$ is C1-C8 optionally substituted alkyl, R$^5$ is cyclohexyl [As substituents of cyclohexyl may be mentioned 1 or 2 or more selected from the group consisting of halogen, C1-C8 optionally substituted akyl, —OH, and —NH$_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, —OH, and —NH$_2$] and Y is —O—.

3) In formula I, wherein R$^1$ is hydrogen, R$^2$ is hydrogen, R$^3$ is C6-C14 aryl group substituted by -G-R$^{15}$ {G is —(CO)—; R$^{15}$ is C1-C8 optionally substituted alkyt C3-C8 optionally substituted cycloalkyl, C6-C14 optionally substituted aryl, optionally substituted heterocyclyl, —OR$^{87}$ (R$^{87}$ is hydrogen, C1-C8 optionally substituted alkyl, optionally substituted arylalkyl or optionally substituted heterocyclylalkyl) or —NR$^{88}$R$^{89}$ (R$^{88}$ and R$^{89}$, which may be the same or different, are hydrogen, C1-C8 optionally substituted alky, C3-C8 optionally substituted cycloalkyl, C6-C14 optionally substituted aryl or optionally substituted heterocyclyl)}[wherein C6-C14 aryl group as R$^3$ may be substituted by 1 or 2 or more substituents selected from the group consisting of halogen, —CN, C1-C8 optionally substituted alkyl, —OR$^{16}$ (R$^{16}$ is hydrogen, C1-C8 optionally substituted alkyl), —NR$^{17}$R$^{18}$ (R$^{17}$ and R$^{18}$, which may be the same or different, are hydrogen or C1-C8 optionally substituted alkyl)], R$^4$ is C1-C8 optionally substituted alkyl, R$^5$ is cyclohexyl [As substituents of cyclohexyl may be mentioned 1 or 2 or more selected from the group consisting of halogen, C1-C8 optionally substituted alkyl, —OH, and —NH$_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, —OH, and —NH$_2$] and Y is —O—.

4) In formula I, wherein R$^1$ is hydrogen, R$^2$ is hydrogen, R$^3$ is unsubstituted bicyclic heteroaryl or substituted bicyclic heteroaryl [As substituents of bicyclic heteroaryl may be mentioned 1 or 2 or more from the group consisting of halogen, —CN, C1-C8 optionally substituted alkyl, C6-C14 optionally substituted aryl, optionally substituted heterocyclyl, —OR$^{16}$ (R$^{16}$ is hydrogen, C1-C8 optionally substituted alkyl, optionally substituted arylalkyl or optionally substituted beterocyclylalkyl), —NR$^{17}$R$^{18}$ (R$^{17}$ and R$^{18}$, which may be the same or different, are hydrogen or C1-C8 optionally substituted alkyl), NH(CO)R$^{19}$ (R$^{19}$ is C1-C8 optionally substituted alkyl, C3-C8 optionally substituted cycloalkyl, C6-C14 optionally substituted aryl or optionally substituted heterocyclyl) and —SR$^{17}$ (R$^{17}$ is C1-C8 optionally substituted alkyd, R$^4$ is C1-C8 optionally substituted alkyl, R$^5$ is cyclohexyl [As substituents of cyclohexyl may be mentioned 1 or 2 or more selected from the group consisting of halogen, C1-C8 optionally substituted alkyl, —OH, and —NH$_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, —OH, and —NH$_2$] and Y is —O—.

5) In formula I, wherein R$^1$ is hydrogen, R$^2$ is halogen, R$^3$ is C6-C14 aryl group substituted by C6-C14 optionally substituted aryl or optionally substituted heterocyclyl [wherein C6-C14 aryl group as R$^3$ may be substituted by 1 or 2 or more substituents selected from the group consisting of halogen, —CN, C1-C8 optionally substituted alkyl, —OR$^{16}$ (R$^{16}$ is hydrogen, C1-C8 optionally substituted alkyl), and —NR$^{17}$R$^{18}$ (R$^{17}$ and R$^{18}$, which may be the same or different, are hydrogen or C1-C8 optionally substituted alkyl)], R$^4$ is hydrogen, R$^5$ is cyclohexyl [As substituents of cyclohexyl may be mentioned 1 or 2 or more selected from the group consisting of halogen, C1-C8 optionally substituted alkyd —OH, and —NH$_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, —OH, and —NH$_2$] and Y is —O—.

6) In formula I, wherein R$^1$ is hydrogen, R$^2$ is halogen, R$^3$ is C6-C14 aryl group substituted by —OR$^{87}$ (R$^{17}$ is C1-C8 optionally substituted alkyl, optionally substituted arylalkyl or optionally substituted heterocyclylalkyl) [wherein C6-C14 aryl group as $R^3$ may be substituted by 1 or 2 or more substituents selected from the group consisting of halogen, —CN, C1-C8 optionally substituted alkyl, —$OR^{16}$ ($R^{16}$ is hydrogen, C1-C8 optionally substituted alkyl), and —$NR^{17}R^{18}$ ($R^{17}$ and $R^{18}$, which may be the same or different, are hydrogen or C1-C8 optionally substituted alkyl)], $R^4$ is hydrogen, $R^5$ is cyclohexyl [As substituents of cyclohexyl may be mentioned 1 or 2 or more selected from the group consisting of halogen, C1-C8 optionally substituted alkyl, —OH, and —$NH_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, —OH, and —$NH_2$] and Y is —O—.

7) In formula I, wherein $R^1$ is hydrogen, $R^2$ is F, $R^3$ is C6-C14 aryl group substituted by -G-$R^{15}$ {G is —(CO)—; $R^{15}$ is C1-C8 optionally substituted alkyl, C3-C8 optionally substituted cycloalkyl, C6-C14 optionally substituted aryl, optionally substituted heterocydlyl, —$OR^{87}$ ($R^{87}$ is hydrogen, C1-C8 optionally substituted alkyl, optionally substituted arylalkyl or optionally substituted heterocyclylalkyl) or —$NR^{88}R^{89}$ ($R^{88}$ and $R^{89}$, which may be the same or different, are hydrogen, C1-C8 optionally substituted alkyl, C3-C8 optionally substituted cycloalkyl, C6-C14 optionally substituted aryl or optionally substituted heterocyclyl)}[wherein C6-C14 aryl group as $R^3$ may be substituted by 1 or 2 or more substituents selected from the group consisting of halogen, —CN, C1-C8 optionally substituted alkyl, —$OR^{16}$ ($R^{16}$ is hydrogen, C1-C8 optionally substituted alkyl), and —$NR^{17}R^{18}$ ($R^{17}$ and $R^{18}$, which may be the same or different, are hydrogen or C1-C8 optionally substituted alkyl)], $R^4$ is hydrogen, $R^5$ is cyclohexyl [As substituents of cyclohexyl may be mentioned 1 or 2 or more selected from the group consisting of halogen, C1-C8 optionally substituted alkyl, —OH, and —$NH_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, —OH, and —$NH_2$] and Y is —O—.

8) In formula I, wherein $R^1$ is hydrogen, $R^2$ is halogen, $R^3$ is unsubstituted bicyclic heteroaryl or substituted bicyclic heteroaryl (As substituents of bicyclic heteroaryl may be mentioned 1 or 2 or more selected from the group consisting of halogen, —CN, C1-C8 optionally substituted alkyl, C6-C14 optionally substituted aryl, optionally substituted heterocyclyl, —$OR^{16}$ ($R^{16}$ is hydrogen, C1-C8 optionally substituted alkyl, optionally substituted arylalkyl or optionally substituted heterocyclylalkyl), —$NR^{17}R^{18}$ ($R^{17}$ and $R^{18}$, which may be the same or different, are hydrogen or C1-C8 optionally substituted alkyl), —NH(CO)$R^{19}$ ($R^{19}$ is C1-C8 optionally substituted alkyl, C3-C8 optionally substituted cycloalkyl, C6-C14 optionally substituted aryl or optionally substituted heterocyclyl) and —$SR^{17}$ ($R^{17}$ is C1-C8 optionally substituted alkyl)], $R^4$ is hydrogen, $R^5$ is cyclohexyl [As substituents of cyclohexyl may be mentioned 1 or 2 or more selected from the group consisting of halogen, C1-C8 optionally substituted alkyl, —OH, and—$NH_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, —OH, and —$NH_2$] and Y is —O—.

9) In formula I, wherein $R^1$ is hydrogen, $R^2$ is hydrogen, $R^3$ is C6-C14 optionally substituted aryl, $R^4$ is hydrogen or C1-C8 optionally substituted alkyl, $R^5$ is cyclohexyl [As substituents of cyclohexyl may be mentioned 1 or 2 or more selected from the group consisting of halogen, C1-C8 optionally substituted alkyl, —OH, and —$NH_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, and —$NH_2$] and Y is —O—.

10) In formula I, wherein $R^1$ is hydrogen, $R^2$ is halogen, $R^3$ is C6-C14 optionally substituted aryl, $R^4$ is hydrogen or C1-C8 optionally substituted alkyl, $R^5$ is cyclohexyl [As substituents of cyclohexyl may be mentioned 1 or 2 or more selected from the group consisting of halogen, C1-C8 optionally substituted alkyl, and —$NH_2$], unsubstituted saturated heterocyclyl or substituted saturated heterocyclyl [As substituents of heterocyclyl may be mentioned 1 or 2 or more selected from the group consisting of halogen, C1-C8 optionally substituted alkyl, —OH, and —$NH_2$] and Y is —O—.

The compounds of the first aspect may be provided as a salt, preferably as a pharmaceutically acceptable salt of the compounds of formula I. Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid, trifluoroacetic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are non-toxic and strong enough to form salts. Such organic bases are already well known in the art and may include amino acids such as arginine and lysine; mono-, di-, or trihydroxyalkylamines such as mono-, di-, and triethanolamine; choline; mono-, di-, and trialkylamines, such as methylamine, dimethylamine, and trimethylamine; guanidine; N-methylglucosamine; N-methylpiperazine; morpholine; ethylenediamine; N-benzylphenethylamine; tris(hydroxymethyl) aminomethane; and the like.

Salts may be prepared in a conventional manner using methods well known in the art. Acid addition salts of said basic compounds may be prepared by dissolving the free base compounds of the invention in aqueous or aqueous alcohol solution or other suitable solvents containing the required acid. Where a compound of the invention contains an acidic finction, a base salt of said compound may be prepared by reacting said compound with a suitable base. The acid or base salt may separate directly or can be obtained by concentrating the solution e.g. by evaporation. The compounds of this invention may also exist in solvated or hydrated forms.

The invention also extends to a prodrug of the aforementioned compounds such as an ester or amide thereof. A prodrug is any compound that may be converted under physiological conditions or by solvolysis to any of the compounds of the invention or to a pharmaceutically acceptable salt of the compounds of the invention. A prodrug may be inactive when administered to a subject but is converted in vivo to an active compound of the invention.

The compounds of the invention may contain 1 or 2 or more asymmetric carbon atoms and may exist in racemic and optically active forms. The compounds of the invention may exist in trans or cis form, The first aspect of the invention covers all of these compounds.

As specific examples of compounds of the formula I above there may be mentioned compounds listed in Table A below.

TABLE A
| Compound No. | R¹ | R² | R³ | R⁴ | R⁵ | Y |
|---|---|---|---|---|---|---|
| 1 | H | H | 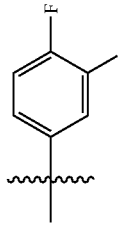 | H | CH₃ | O |
| 2 | H | H | 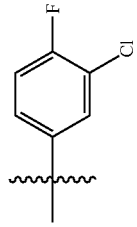 | H | 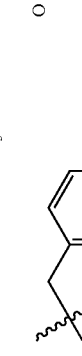 | O |
| 3 | H | H | 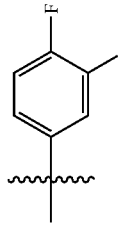 | H | 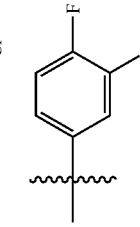 | O |
| 4 | H | H | 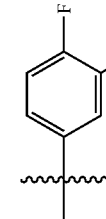 | H | H | O |
| 5 | H | H | 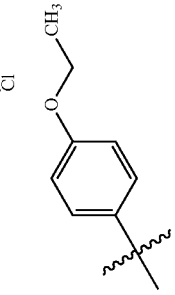 | CH₃ | 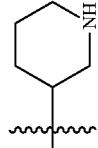 | O |
| 6 | H | H | 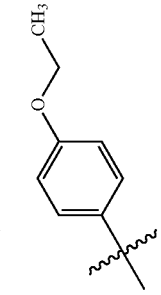 | CH₃ | 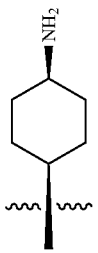 | O |

TABLE A-continued

| Compound No. | R¹ | R² | R³ | R⁴ | R⁵ | Y |
|---|---|---|---|---|---|---|
| 7 | H | H | 4-(2-methoxyethoxy)phenyl | CH₃ | 3-(2-propylpiperidin-3-yl) | O |
| 8 | H | H | 4-(2-methoxyethoxy)phenyl | CH₃ | 5-(2-propylpiperidin-2-yl) | O |
| 9 | H | H | 2-fluorophenyl | neopentyl | trans-4-aminocyclohexyl | O |
| 10 | H | H | 3-chloro-4-fluorophenyl | neopentyl | trans-4-aminocyclohexyl | O |
| 11 | H | H | 3-chloro-4-fluorophenyl | isobutyl (sec-butyl) | trans-4-aminocyclohexyl | O |
| 12 | H | H | 3-chloro-4-fluorophenyl | 2-methylallyl | trans-4-aminocyclohexyl | O |

TABLE A-continued

| Compound No. | R¹ | R² | R³ | R⁴ | R⁵ | Y |
|---|---|---|---|---|---|---|
| 13 | H | H | prenyl-type group (CH₃)₂C=CH-CH₂-CH₂-C(CH₃)=CH-CH₂- | H | 4-aminocyclohexyl (trans) with NH₂ | O |
| 14 | H | H | 4-(methoxymethoxy)phenyl | CH₃ | 3-methylpiperidin-3-yl (CHIRAL), NH | O |
| 15 | H | H | 4-(methoxymethoxy)phenyl | CH₃ | 4-ethyl-3-methylpiperidin-3-yl, HN | O |
| 16 | H | H | 4-(methoxymethoxy)phenyl | CH₃ | 4-ethyl-3-methylpiperidin-3-yl, HN | O |
| 17 | H | H | 4-(methoxymethoxy)phenyl | CH₃ | 2,5-dimethylpiperidin-5-yl, NH | O |
| 18 | H | H | 4-(methoxymethoxy)phenyl | CH₃ | 2,5-dimethylpiperidin-5-yl, NH | O |

TABLE A-continued
| Compound No. | R¹ | R² | R³ | R⁴ | R⁵ | Y |
|---|---|---|---|---|---|---|
| 19 | H | I | 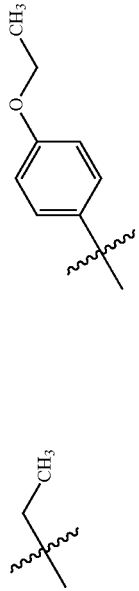 | H |  | O |
| 20 | H | 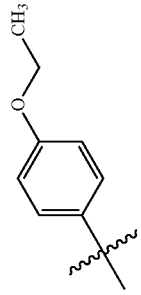 | 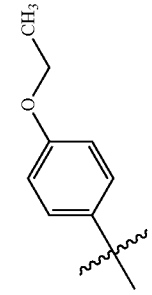 | CH₃ | 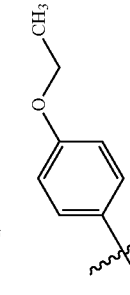 | O |
| 21 | H | 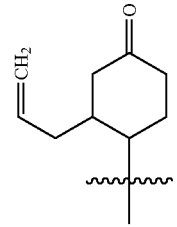 | 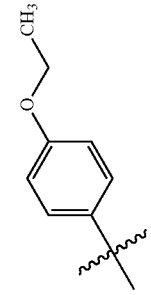 | CH₃ | 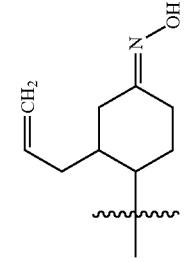 | O |
| 22 | H | 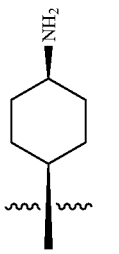 | 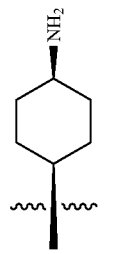 | CH₃ | | O |
| 23 | H | H | | CH₃ | | O |
| 24 | H | H | | CH₃ | | O |

TABLE A-continued
| Compound No. | R¹ | R² | R³ | R⁴ | R⁵ | Y |
|---|---|---|---|---|---|---|
| 25 | H | H | 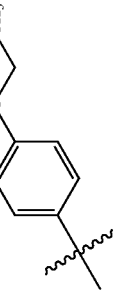 | CH₃ | 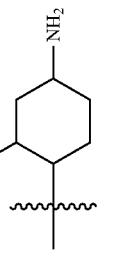 | O |
| 26 | H | H | 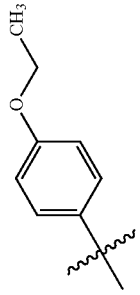 | CH₃ | 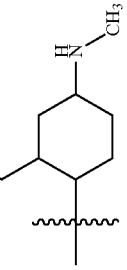 | O |
| 27 | H | H | 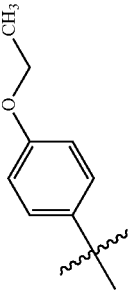 | CH₃ | 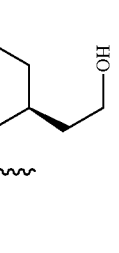 | O |
| 28 | H | H | 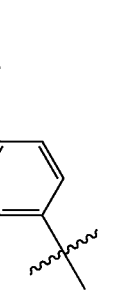 | CH₃ |  | O |
| 29 | H | H | 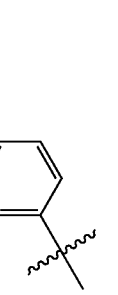 | CH₃ |  | O |
| 30 | H | H | 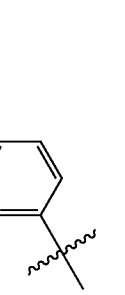 | CH₃ |  | O |

TABLE A-continued
| Compound No. | R¹ | R² | R³ | R⁴ | R⁵ | Y |
|---|---|---|---|---|---|---|
| 31 | H | H | 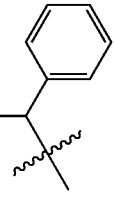 | CH₃ | 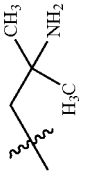 | O |
| 32 | H | H |  | CH₃ | 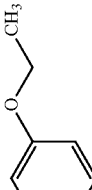 CHIRAL | O |
| 33 | H | H |  | CH₃ |  | O |
| 34 | H | H |  | CH₃ |  | O |
| 35 | H | H | 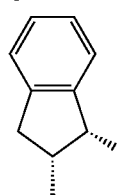 | CH₃ | 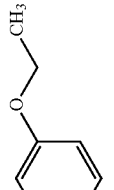 | O |
| 36 | H | H |  | CH₃ |  | O |

TABLE A-continued
| Compound No. | R¹ | R² | R³ | R⁴ | R⁵ | Y |
|---|---|---|---|---|---|---|
| 37 | H | H |  | CH₃ | 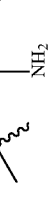 | O |
| 38 | H | H |  | CH₃ |  | O |
| 39 | H | H |  | CH₃ | 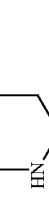 | O |
| 40 | H | H | 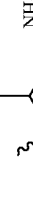 | CH₃ |  | O |
| 41 | H | H |  | CH₃ |  | O |
| 42 | H | H | | CH₃ | | O |

TABLE A-continued

| Compound No. | R¹ | R² | R³ | R⁴ | R⁵ | Y |
|---|---|---|---|---|---|---|
| 43 | H | H | 4-(2-methoxyethoxy)phenyl | CH₃ | 2-amino-2-(hydroxymethyl)-3-hydroxypropyl | O |
| 44 | H | H | 4-(2-methoxyethoxy)phenyl | CH₃ | 1-(aminomethyl)-3,3,5-trimethylcyclohexyl | O |
| 45 | H | H | 2-(methylthio)benzothiazol-6-yl | CH₃ | piperidin-3-yl | O |
| 46 | H | H | 2-(methylthio)benzothiazol-6-yl | CH₃ | trans-4-aminocyclohexyl | O |
| 47 | H | H | 4-(methoxycarbonyl)phenyl | CH₃ | piperidin-3-yl | O |
| 48 | H | H | 3-(methanesulfonamido)phenyl | CH₃ | piperidin-3-yl | O |
| 49 | H | H | 2-cyano-4-fluoro-5-(piperidin-3-yloxy)phenyl | CH₃ | piperidin-3-yl | O |

TABLE A-continued

| Compound No. | R¹ | R² | R³ | R⁴ | R⁵ | Y |
|---|---|---|---|---|---|---|
| 50 | H | H | 3,5-dimethoxyphenyl | CH₃ | 3-piperidinyl | O |
| 51 | H | H | 4-benzoylphenyl | CH₃ | 3-piperidinyl | O |
| 52 | H | H | 4-benzylphenyl | CH₃ | 3-piperidinyl | O |
| 53 | H | H | 4-cyano-3-trifluoromethylphenyl | CH₃ | 3-piperidinyl | O |
| 54 | H | H | 4-(trifluoromethylthio)phenyl | CH₃ | 3-piperidinyl | O |
| 55 | H | H | 4-chloro-2-methoxyphenyl | CH₃ | 3-piperidinyl | O |

TABLE A-continued
| Compound No. | R¹ | R² | R³ | R⁴ | R⁵ | Y |
|---|---|---|---|---|---|---|
| 56 | H | H | 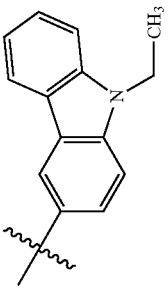 | CH₃ | 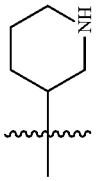 | O |
| 57 | H | H | 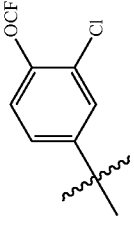 | CH₃ | 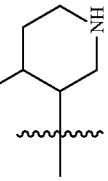 | O |
| 58 | H | H | 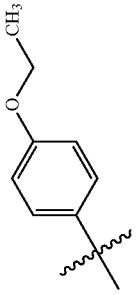 | CH₃ | 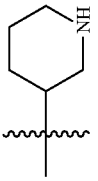 | O |
| 59 | H | H | 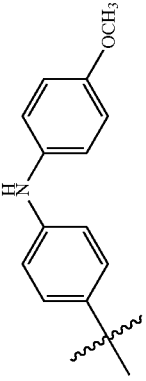 | CH₃ | 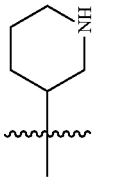 | O |
| 60 | H | H | 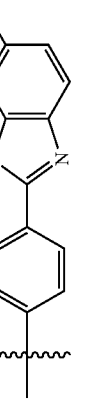 | CH₃ | 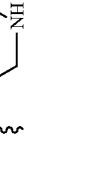 | O |
| 61 | H | H | 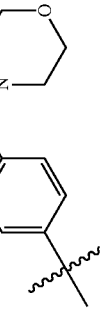 | CH₃ |  | O |

TABLE A-continued
| Compound No. | R¹ | R² | R³ | R⁴ | R⁵ | Y |
|---|---|---|---|---|---|---|
| 62 | H | H | 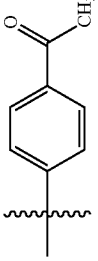 | CH₃ | 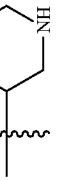 | O |
| 63 | H | H | 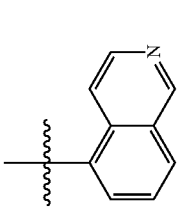 | CH₃ | 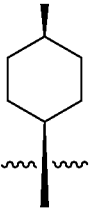 | O |
| 64 | H | H | 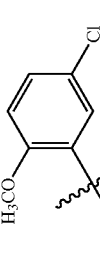 | CH₃ | 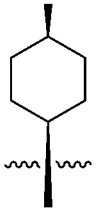 | O |
| 65 | H | H | 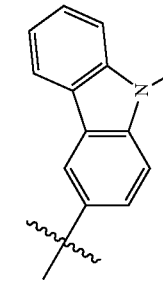 | CH₃ | 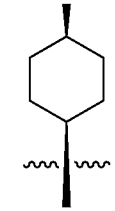 | O |
| 66 | H | H | 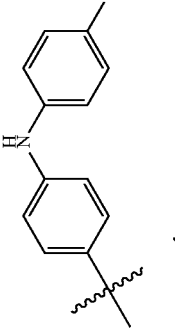 | CH₃ | 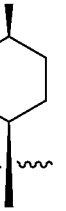 | O |
| 67 | H | H | 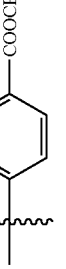 | CH₃ |  | O |

TABLE A-continued
| Compound No. | R¹ | R² | R³ | R⁴ | R⁵ | Y |
|---|---|---|---|---|---|---|
| 68 | H | H | 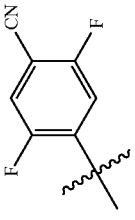 | CH₃ | 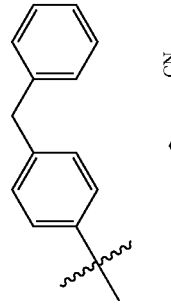 | O |
| 69 | H | H |  | CH₃ | 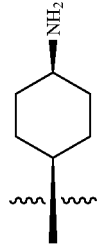 | O |
| 70 | H | H | 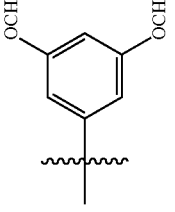 | CH₃ | 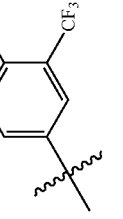 | O |
| 71 | H | H | 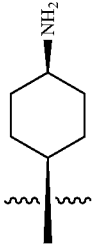 | CH₃ | 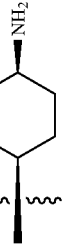 | O |
| 72 | H | H | 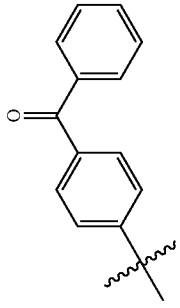 | CH₃ | 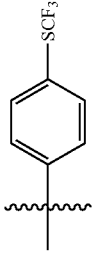 | O |
| 73 | H | H | 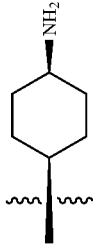 | CH₃ | 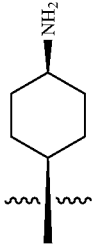 | O |

TABLE A-continued
| Compound No. | R¹ | R² | R³ | R⁴ | R⁵ | Y |
|---|---|---|---|---|---|---|
| 74 | H | H | 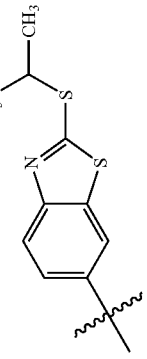 | CH₃ | 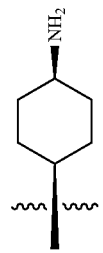 | O |
| 75 | H | H | 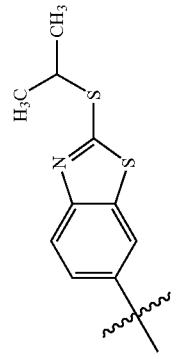 | CH₃ | 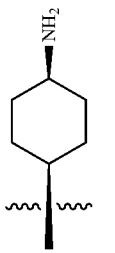 | O |
| 76 | H | H | 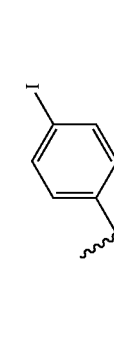 | CH₃ | 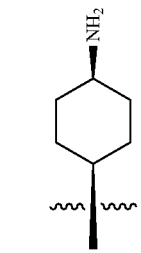 | O |
| 77 | H | H |  | CH₃ |  | O |
| 78 | H | H |  | CH₃ |  | O |
| 79 | H | H |  | H |  CH₃ | S |

TABLE A-continued

| Compound No. | R¹ | R² | R³ | R⁴ | R⁵ | Y |
|---|---|---|---|---|---|---|
| 80 | H | H | 4-(2-methoxyethoxy)phenyl | CH₃ | 3-methylpiperidin-3-yl | S |
| 81 | H | H | 4-(2-methoxyethoxy)phenyl | CH₃ | 3-aminopropyl (branched) | S |
| 82 | H | H | 4-(2-methoxyethoxy)phenyl | CH₃ | 3-methyl-4-(carbamoylmethyl)piperidin-4-yl | O |
| 83 | H | H | 4-(2-methoxyethoxy)phenyl | CH₃ | 3-methyl-4-(N-methylcarbamoylmethyl)piperidin-4-yl | O |
| 84 | H | H | 4-(2-methoxyethoxy)phenyl | CH₃ | 3-methyl-4-(N,N-dimethylcarbamoylmethyl)piperidin-4-yl | O |

TABLE A-continued
| Compound No. | R¹ | R² | R³ | R⁴ | R⁵ | Y |
|---|---|---|---|---|---|---|
| 85 | H | H | 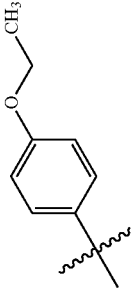 | CH₃ | 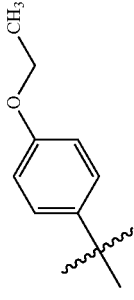 | O |
| 86 | H | H | 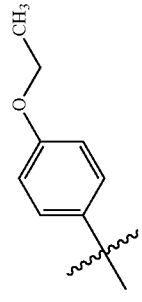 | CH₃ | 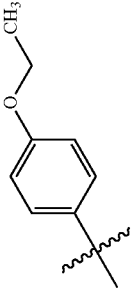 | O |
| 87 | H | H | 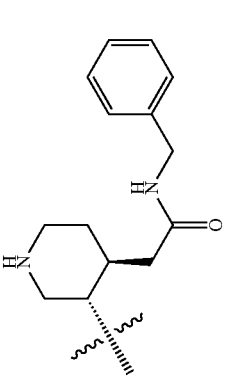 | CH₃ | 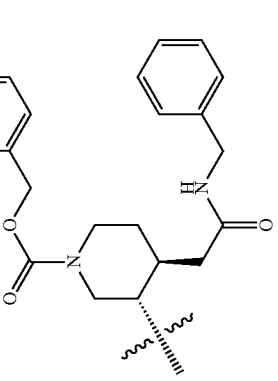 | O |
| 88 | H | H | 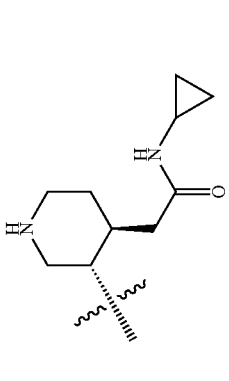 | 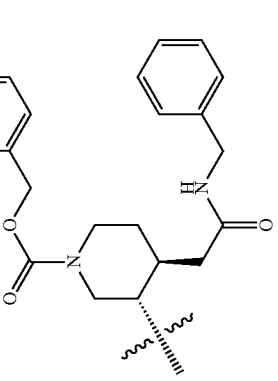 | 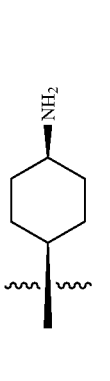 | O |

TABLE A-continued

| Compound No. | R¹ | R² | R³ | R⁴ | R⁵ | Y |
|---|---|---|---|---|---|---|
| 89 | H | H | 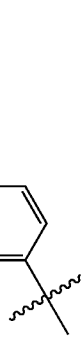 4-(2-methoxyethoxy)phenyl | CH₃ | trans-4-aminocyclohexyl | O |
| 90 | H | H | 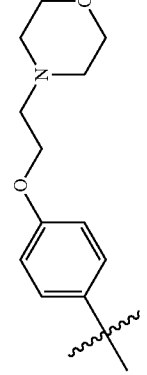 4-(2-morpholinoethoxy)phenyl | CH₃ | trans-4-aminocyclohexyl | O |
| 91 | H | H | 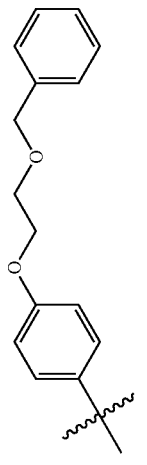 4-(2-benzyloxyethoxy)phenyl | CH₃ | trans-4-aminocyclohexyl | O |
| 92 | H | H | 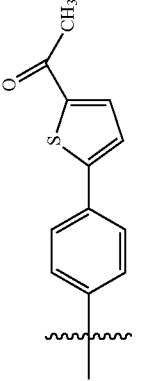 4-(5-acetylthiophen-2-yl)phenyl | CH₃ | trans-4-aminocyclohexyl | O |
| 93 | H | H | 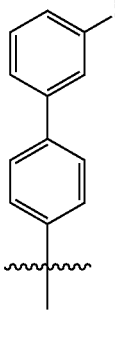 3'-aminobiphenyl-4-yl | CH₃ | trans-4-aminocyclohexyl | O |
| 94 | H | H | 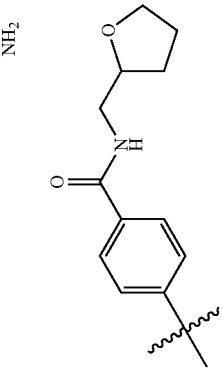 4-[(tetrahydrofuran-2-ylmethyl)carbamoyl]phenyl | CH₃ | CH₃ | O |

TABLE A-continued
| Compound No. | R¹ | R² | R³ | R⁴ | R⁵ | Y |
|---|---|---|---|---|---|---|
| 95 | H | H | 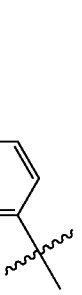 | CH₃ | CH₃ | O |
| 96 | H | H | 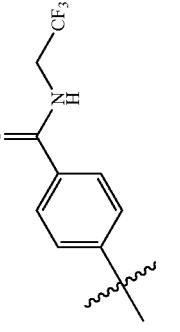 | CH₃ | CH₃ | O |
| 97 | H | H | 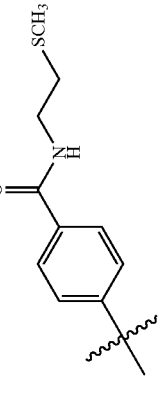 | CH₃ | CH₃ | O |
| 98 | H | H | 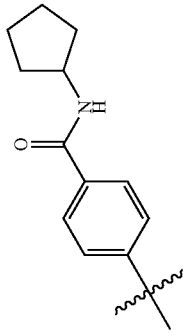 | CH₃ | CH₃ | O |
| 99 | H | H | 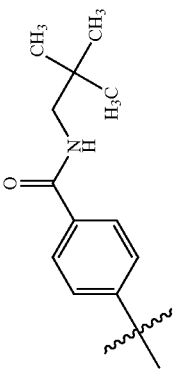 | CH₃ | CH₃ | O |

TABLE A-continued

| Compound No. | R¹ | R² | R³ | R⁴ | R⁵ | Y |
|---|---|---|---|---|---|---|
| 100 | H | H | 4-(pyridin-3-ylmethylcarbamoyl)phenylmethyl | CH₃ | CH₃ | O |
| 101 | H | H | 4-(pyridin-4-ylmethylcarbamoyl)phenylmethyl | CH₃ | CH₃ | O |
| 102 | H | H | 4-iodophenylmethyl | neopentyl (C(CH₃)₂CH₃) | trans-4-aminocyclohexyl | O |
| 103 | H | H | 4-(methoxycarbonyl)phenylmethyl | neopentyl (C(CH₃)₂CH₃) | trans-4-aminocyclohexyl | O |
| 104 | H | -C(CH₃)₂-C(=O)-O-CH₂CH₃ | 4-(methoxymethoxy)phenylmethyl | neopentyl (C(CH₃)₂CH₃) | trans-4-aminocyclohexyl | O |
| 105 | H | H | 4-(2-(pyridin-2-yl)ethoxy)phenylmethyl | CH₃ | trans-4-aminocyclohexyl | O |

TABLE A-continued
| Compound No. | R¹ | R² | R³ | R⁴ | R⁵ | Y |
|---|---|---|---|---|---|---|
| 106 | H | H | 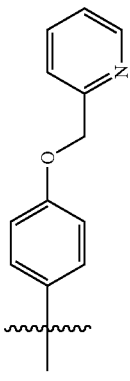 | CH₃ |  | O |
| 107 | H | H | 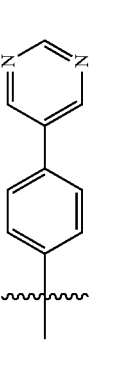 | CH₃ | CH₃ | O |
| 108 | H | H | 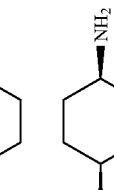 | CH₃ | CH₃ | O |
| 109 | H | H | 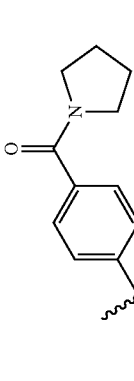 | CH₃ | 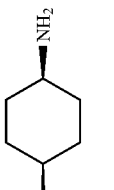 | O |
| 110 | H | H | 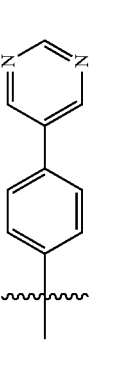 | CH₃ | 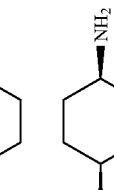 | O |
| 111 | H | H | 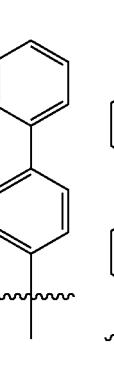 | CH₃ | 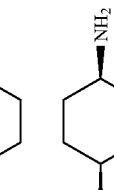 | O |
| 112 | H | H | 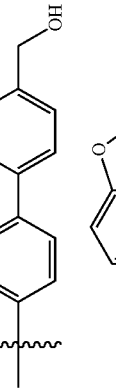 | CH₃ |  | O |

TABLE A-continued
| Compound No. | R¹ | R² | R³ | R⁴ | R⁵ | Y |
|---|---|---|---|---|---|---|
| 113 | H | H | 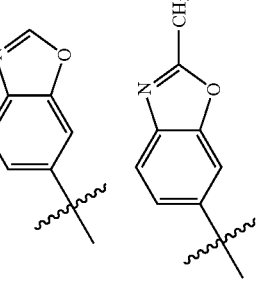 | CH₃ | 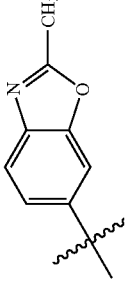 | O |
| 114 | H | H | 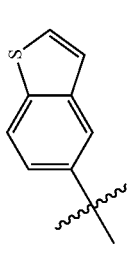 | CH₃ | 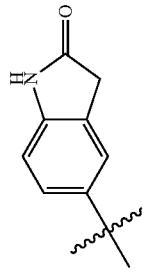 | O |
| 115 | H | H | 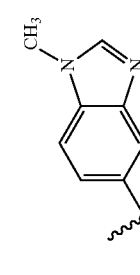 | CH₃ | 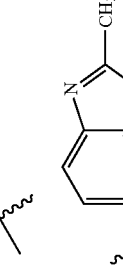 | O |
| 116 | H | H | 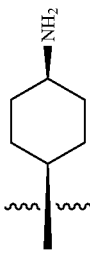 | CH₃ | 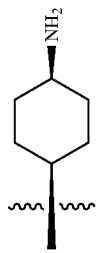 | O |
| 117 | H | H | | CH₃ | | O |
| 118 | H | H | | CH₃ | | O |

TABLE A-continued

| Compound No. | R¹ | R² | R³ | R⁴ | R⁵ | Y |
|---|---|---|---|---|---|---|
| 119 | H | H | 1-methyl-indazol-5-yl | CH₃ | trans-4-aminocyclohexyl | O |
| 120 | H | H | 1-(2-methoxyethyl)-indazol-5-yl | CH₃ | trans-4-aminocyclohexyl | O |
| 121 | H | H | 1-(2-methylthioethyl)-indazol-5-yl | CH₃ | trans-4-aminocyclohexyl | O |
| 122 | H | H | 1-(2-morpholinoethyl)-indazol-5-yl | CH₃ | trans-4-aminocyclohexyl | O |
| 123 | H | H | 1H-indazol-5-yl | CH₃ | trans-4-aminocyclohexyl | O |
| 124 | H | H | 2-methyl-benzothiazol-5-yl | CH₃ | trans-4-aminocyclohexyl | O |

TABLE A-continued
| Compound No. | R¹ | R² | R³ | R⁴ | R⁵ | Y |
|---|---|---|---|---|---|---|
| 125 | H | H | 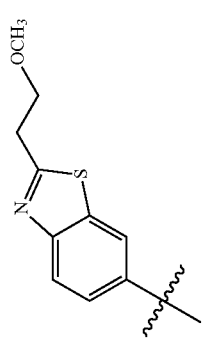 | $CH_3$ | 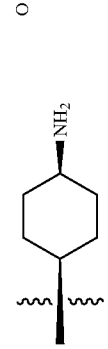 | O |
| 126 | H | H | 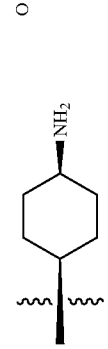 | $CH_3$ | 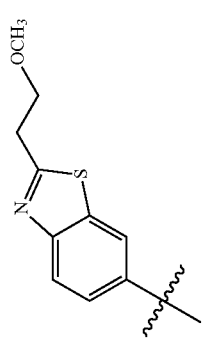 | O |
| 127 | H | H | 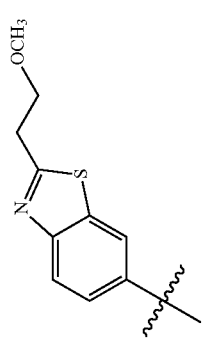 | $CH_3$ | 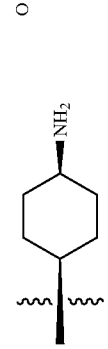 | O |
| 128 | H | H | 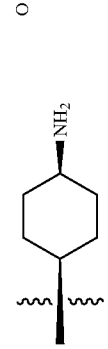 | $CH_3$ | 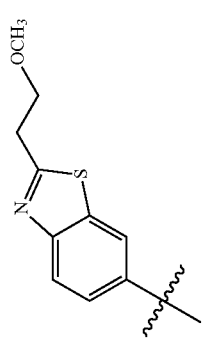 | O |
| 129 | H | H | 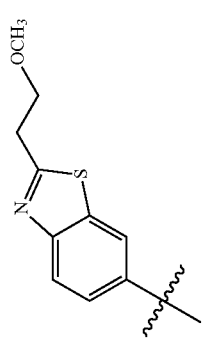 | $CH_3$ | 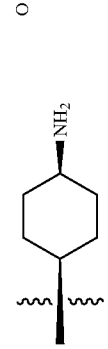 | O |
| 130 | H | H | 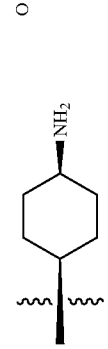 | $CH_3$ | 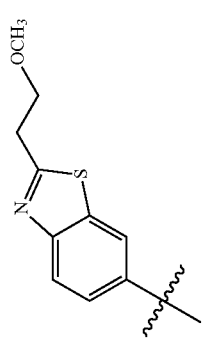 | O |
| 131 | H | H | 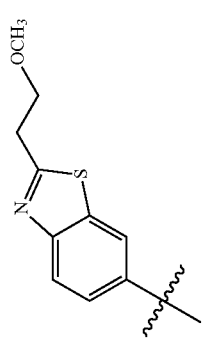 | $CH_3$ | 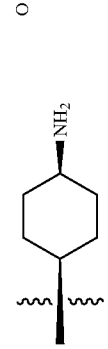 | S |

TABLE A-continued
| Compound No. | R¹ | R² | R³ | R⁴ | R⁵ | Y |
|---|---|---|---|---|---|---|
| 132 | H | H | 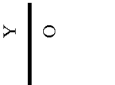 | CH₃ |  | O |
| 133 | H | H |  | CH₃ |  | O |
| 134 | H | H |  | CH₃ |  | O |
| 135 | H | H |  | CH₃ |  | S |
| 136 | H | H |  | CH₃ |  | O |

TABLE A-continued

| Compound No. | R¹ | R² | R³ | R⁴ | R⁵ | Y |
|---|---|---|---|---|---|---|
| 137 | H | H | 4-fluorophenyl benzamide | CH₃ | trans-4-aminocyclohexyl | O |
| 138 | H | H | 1H-indol-5-yl benzamide | CH₃ | trans-4-aminocyclohexyl | O |
| 139 | H | H | 1H-indol-6-yl benzamide | CH₃ | trans-4-aminocyclohexyl | S |
| 140 | H | H | 1H-indol-4-yl benzamide | CH₃ | trans-4-aminocyclohexyl | O |
| 141 | H | H | 2-(dimethylamino)ethyl benzamide | CH₃ | trans-4-aminocyclohexyl | O |

TABLE A-continued
| Compound No. | R¹ | R² | R³ | R⁴ | R⁵ | Y |
|---|---|---|---|---|---|---|
| 142 | H | H | 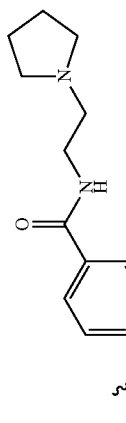 | CH₃ | 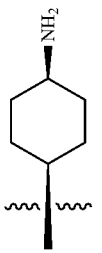 | S |
| 143 | H | H | 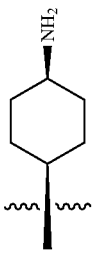 | CH₃ | 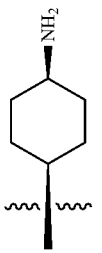 | S |
| 144 | H | H | 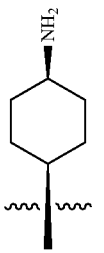 | CH₃ | 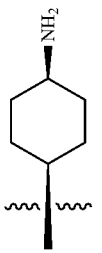 | O |
| 145 | H | H | 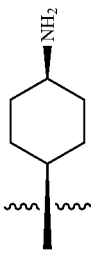 | CH₃ | 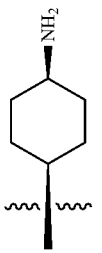 | O |
| 146 | H | H |  | CH₃ | 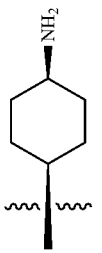 | O |

TABLE A-continued

| Compound No. | R¹ | R² | R³ | R⁴ | R⁵ | Y |
|---|---|---|---|---|---|---|
| 147 | H | H | 3-(pyridin-3-yl)phenyl | CH₃ | trans-4-aminocyclohexyl | O |
| 148 | H | H | 3-(5-acetylthiophen-2-yl)phenyl | CH₃ | trans-4-aminocyclohexyl | O |
| 149 | H | H | 4-(N-acetylamino)phenyl | CH₃ | trans-4-aminocyclohexyl | S |
| 150 | H | H | 4-(methoxyacetylamino)phenyl | CH₃ | trans-4-aminocyclohexyl | S |
| 151 | H | H | 4-(3-(methylthio)propanoylamino)phenyl | CH₃ | trans-4-aminocyclohexyl | O |

TABLE A-continued

| Compound No. | R¹ | R² | R³ | R⁴ | R⁵ | Y |
|---|---|---|---|---|---|---|
| 152 | H | H | 4-methoxybenzamido-phenyl | CH₃ | trans-4-aminocyclohexyl | O |
| 153 | H | H | 4-cyanobenzamido-phenyl | CH₃ | trans-4-aminocyclohexyl | O |
| 154 | H | H | 4-(isonicotinamido)phenyl | CH₃ | trans-4-aminocyclohexyl | O |
| 155 | H | H | 4-(nicotinamido)phenyl | CH₃ | trans-4-aminocyclohexyl | O |
| 156 | H | H | 4-(benzyloxy)phenyl | CH₃ | trans-4-aminocyclohexyl | S |

TABLE A-continued
| Compound No. | R¹ | R² | R³ | R⁴ | R⁵ | Y |
|---|---|---|---|---|---|---|
| 157 | H | H |  | CH₃ | 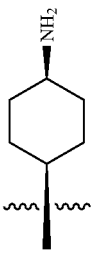 | O |
| 158 | H | H | 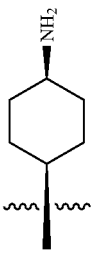 | CH₃ | 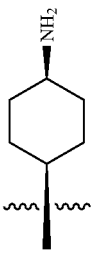 | S |
| 159 | H | H | 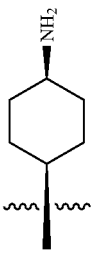 | CH₃ | 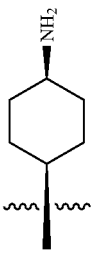 | O |
| 160 | H | H | 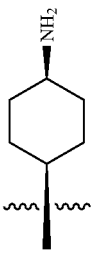 | CH₃ | 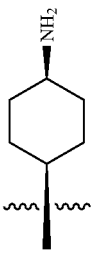 | O |
| 161 | H | H | 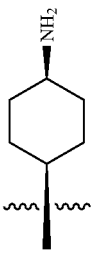 | CH₃ | 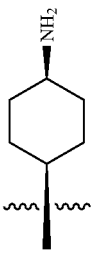 | O |
| 162 | H | H | 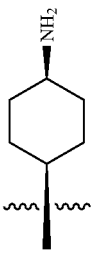 | CH₃ | 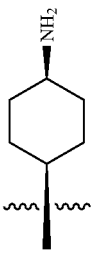 | S |
| 163 | H | H | 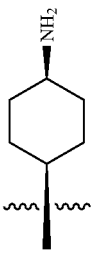 | CH₃ | 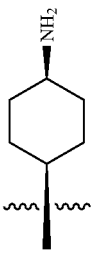 | S |

TABLE A-continued
| Compound No. | R¹ | R² | R³ | R⁴ | R⁵ | Y |
|---|---|---|---|---|---|---|
| 164 | H | H | 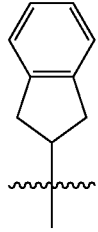 | CH₃ | 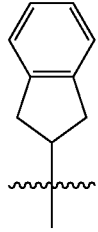 cyclohexyl-NH₂ | O |
| 165 | H | H | 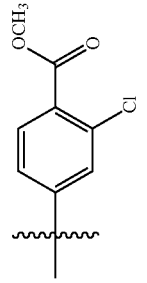 | CH₃ | cyclohexyl-NH₂ | O |
| 166 | H | H | 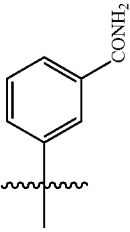 | CH₃ | cyclohexyl-NH₂ | O |
| 167 | H | H | 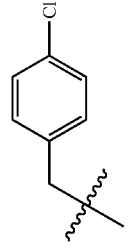 | CH₃ | cyclohexyl-NH₂ | O |
| 168 | H | H | 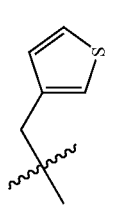 | CH₃ | cyclohexyl-NH₂ | O |
| 169 | H | H | 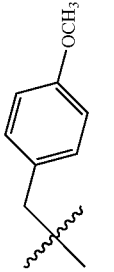 | CH₃ | cyclohexyl-NH₂ | S |
| 170 | H | H | 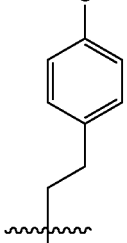 | CH₃ | cyclohexyl-NH₂ | O |

TABLE A-continued

| Compound No. | R¹ | R² | R³ | R⁴ | R⁵ | Y |
|---|---|---|---|---|---|---|
| 171 | H | H | 4-(3-hydroxyprop-1-ynyl)phenyl | CH₃ | 4-aminocyclohexyl | O |
| 172 | H | H | 4-(3,3-dimethylbut-1-ynyl)phenyl | CH₃ | 4-aminocyclohexyl | S |
| 173 | H | H | cyclopropylmethyl (gem-dimethyl) | CH₃ | 4-aminocyclohexyl | O |
| 174 | H | H | 4-methylpentyl (gem-dimethyl) | CH₃ | 4-aminocyclohexyl | O |
| 175 | H | H | 3-methoxypropyl (gem-dimethyl) | CH₃ | 4-aminocyclohexyl | O |
| 176 | H | H | 4-(2-methoxyethoxy)phenyl | isobutyl | 4-aminocyclohexyl | O |
| 177 | H | H | 4-(2-methoxyethoxy)phenyl | isobutyl | 4-aminocyclohexyl | S |

TABLE A-continued
| Compound No. | R¹ | R² | R³ | R⁴ | R⁵ | Y |
|---|---|---|---|---|---|---|
| 178 | H | H | 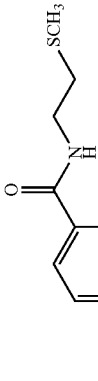 |  |  | O |
| 179 | H | H | 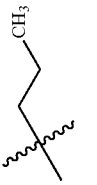 |  |  | O |
| 180 | H | H |  |  |  | O |
| 181 | H | H | 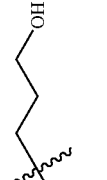 |  |  | O |
| 182 | H | H | 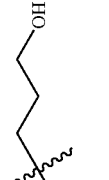 |  | 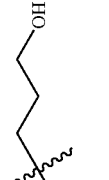 | S |
| 183 | H | H |  |  |  | O |

TABLE A-continued
| Compound No. | R¹ | R² | R³ | R⁴ | R⁵ | Y |
|---|---|---|---|---|---|---|
| 184 | H | H | 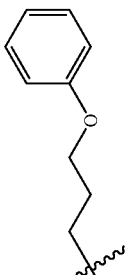 | 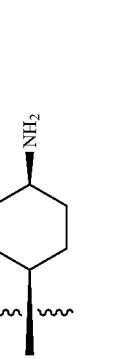 | 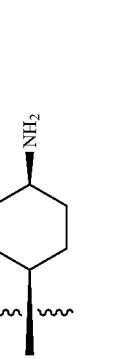 | O |
| 185 | H | H |  |  | 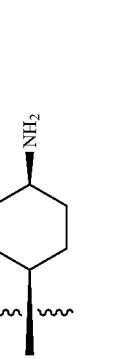 | S |
| 186 | H | H | 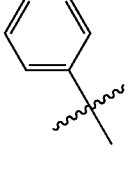 | CH₃ | 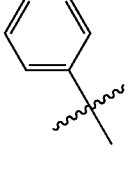 | O |
| 187 | H | H | 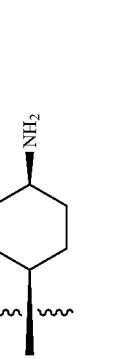 | CH₃ |  | O |
| 188 | H | H | 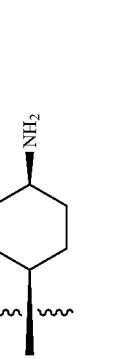 | CH₃ | 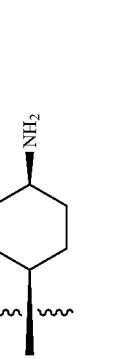 | S |
| 189 | H | H |  | CH₃ |  | O |

TABLE A-continued

| Compound No. | R¹ | R² | R³ | R⁴ | R⁵ | Y |
|---|---|---|---|---|---|---|
| 190 | H | H | 5-acetyl-2-(4-phenyl)thiophene | CH₃ | 3-piperidinyl | O |
| 191 | H | H | 4-biphenyl | CH₃ | 4-piperidinyl | O |
| 192 | H | H | 2-methyl-benzothiazol-6-yl | CH₃ | 3-piperidinyl | O |
| 193 | H | H | 1-methyl-benzimidazol-5-yl | CH₃ | 4-piperidinyl | S |
| 194 | H | H | 1-(2-methylthioethyl)-indazol-5-yl | CH₃ | 3-piperidinyl | O |
| 195 | H | H | 4-morpholinophenyl | CH₃ | 4-piperidinyl | O |
| 196 | H | H | 4-(3-hydroxyprop-1-ynyl)phenyl | CH₃ | 3-piperidinyl | O |

TABLE A-continued

| Compound No. | R¹ | R² | R³ | R⁴ | R⁵ | Y |
|---|---|---|---|---|---|---|
| 197 | H | H | 2-chloro-4-(methoxycarbonyl)phenyl | CH₃ | piperidin-4-yl | O |
| 198 | H | H | thiophen-3-ylmethyl | CH₃ | piperidin-3-yl | O |
| 199 | H | H | 4-(2-methoxyethoxy)phenyl | CH₃ | 1-aminopropan-2-yl (NH₂-CH₂-CH(CH₃)-) | S |
| 200 | H | H | 4-(2-morpholinoethoxy)phenyl | CH₃ | 1-aminobutan-2-yl | S |
| 201 | H | H | 4-(pyridin-2-ylmethoxy)phenyl | CH₃ | 2-amino-2-methylpropyl | O |
| 202 | H | H | 4-((tetrahydrofuran-2-yl)methylcarbamoyl)phenyl | CH₃ | (1R,2S)-2-aminocyclohexyl | O |

TABLE A-continued
| Compound No. | R¹ | R² | R³ | R⁴ | R⁵ | Y |
|---|---|---|---|---|---|---|
| 203 | H | H | 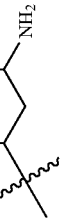 | CH₃ | 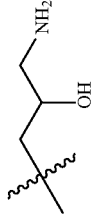 | O |
| 204 | H | H | 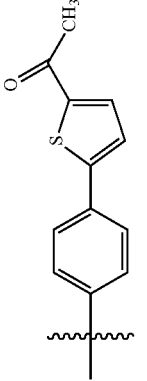 | CH₃ | 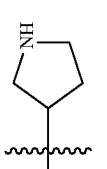 | O |
| 205 | H | H | 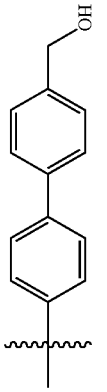 | CH₃ | 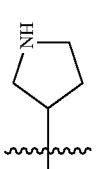 | S |
| 206 | H | H | 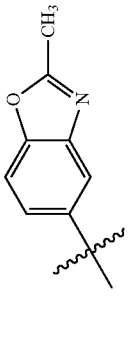 | CH₃ | 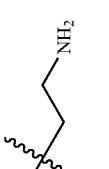 | S |
| 207 | H | H | 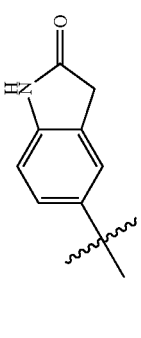 | 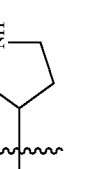 | 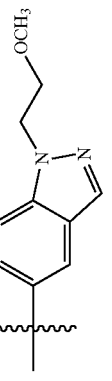 | O |
| 208 | H | H |  | CH₃ (ethyl) | (pyrrolidinyl) | O |

TABLE A-continued
| Compound No. | R¹ | R² | R³ | R⁴ | R⁵ | Y |
|---|---|---|---|---|---|---|
| 209 | H | H | 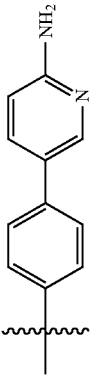 | 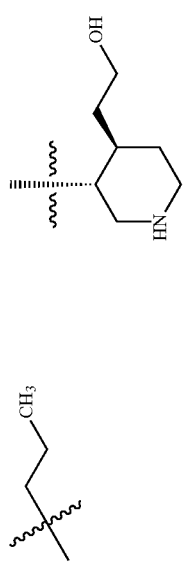 | 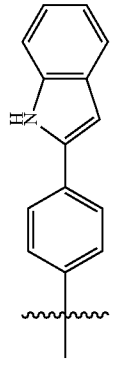 | O |
| 210 | H | H | 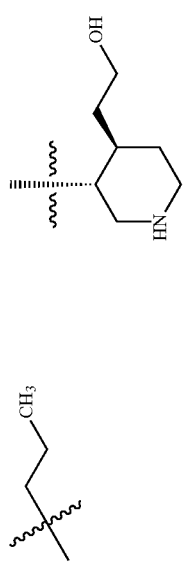 | 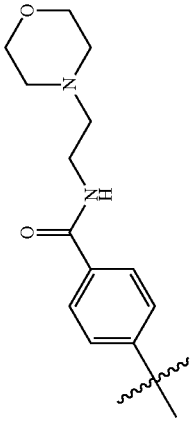 | 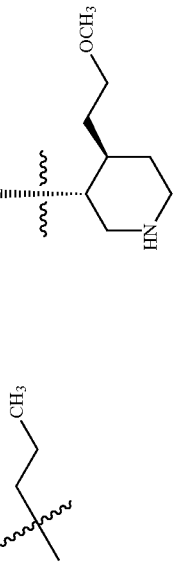 | O |
| 211 | H | H | 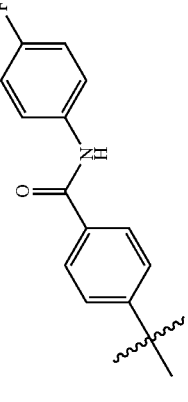 | CH₃-group | piperidine-CH₂CH₂OCH₃ | O |
| 212 | H | H | 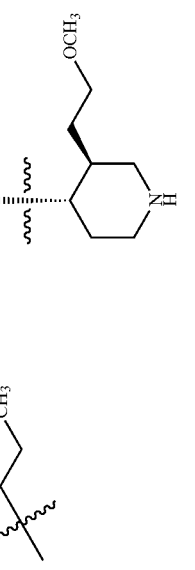 | CH₃-group | piperidine-CH₂CH₂OCH₃ | O |
| 213 | H | H | 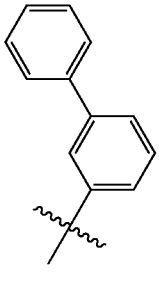 | CH₃ | piperidine-CH₂CH₃ | O |

TABLE A-continued
| Compound No. | R¹ | R² | R³ | R⁴ | R⁵ | Y |
|---|---|---|---|---|---|---|
| 214 | H | H | 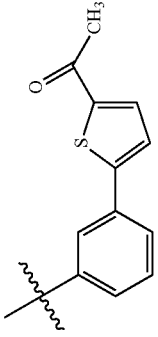 | CH₃ | 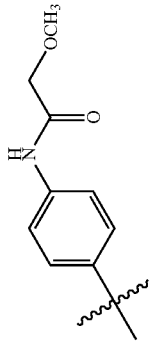 | O |
| 215 | H | H | 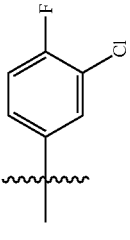 | CH₃ | 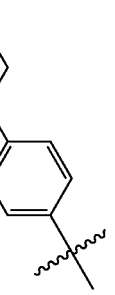 | O |
| 216 | H | H | 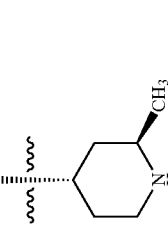 | CH₃ | 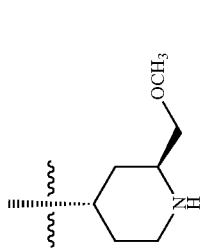 | O |
| 217 | H | F | 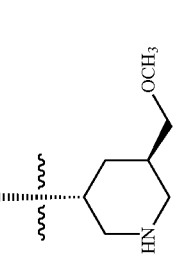 | H | 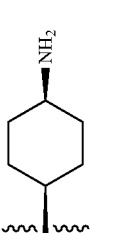 | O |
| 218 | H | F | 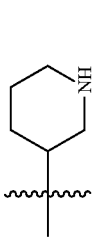 | H | (piperidine NH) | O |

TABLE A-continued
| Compound No. | R¹ | R² | R³ | R⁴ | R⁵ | Y |
|---|---|---|---|---|---|---|
| 219 | H | F | 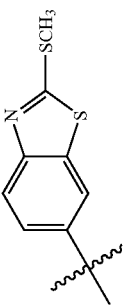 | H | 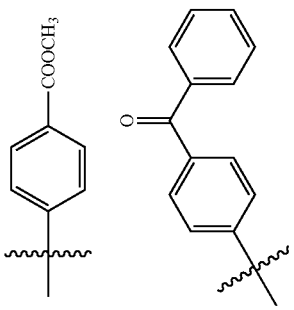 | O |
| 220 | H | Br | 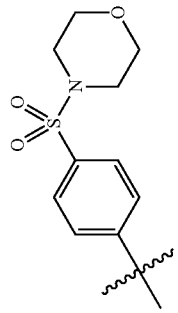 | H | 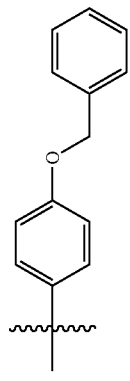 | O |
| 221 | H | Br | 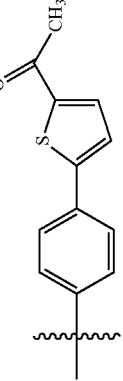 | H | 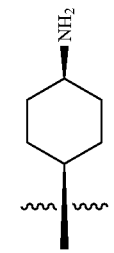 | O |
| 222 | H | Br | 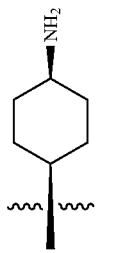 | H | 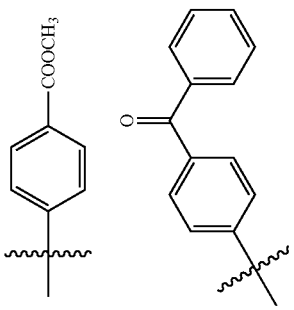 | O |
| 223 | H | Br | 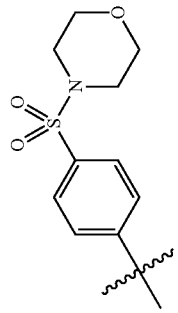 | H | 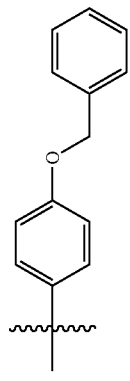 | S |
| 224 | H | Cl | 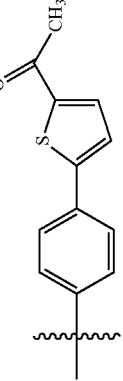 | H | 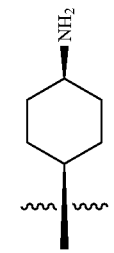 | S |

TABLE A-continued
| Compound No. | R¹ | R² | R³ | R⁴ | R⁵ | Y |
|---|---|---|---|---|---|---|
| 225 | H | Cl | 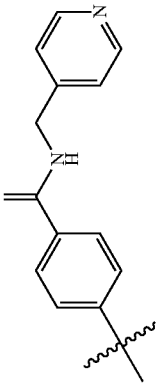 | H | 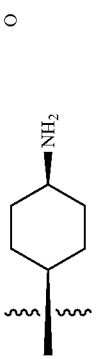 | O |
| 226 | H | Cl | 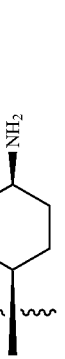 | H | 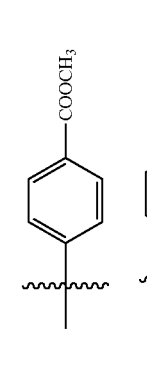 | O |
| 227 | H | Cl | 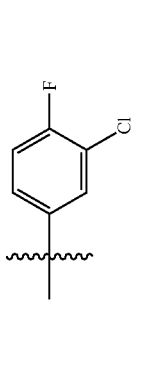 | H | 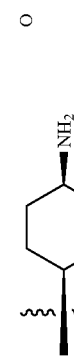 | O |
| 228 | H | Cl | 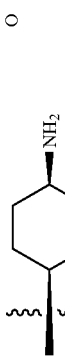 | H | 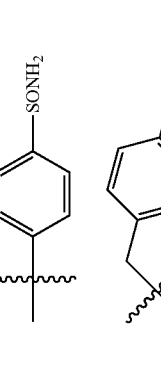 | O |
| 229 | H | Cl | 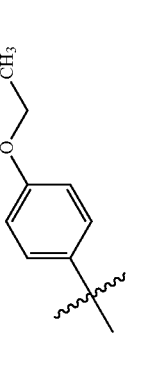 | H | 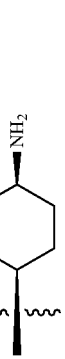 | O |
| 230 | H | Cl | 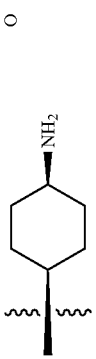 | H | 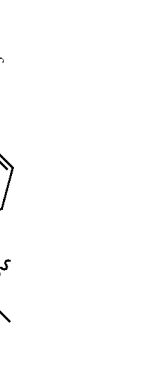 | O |
| 231 | H | Cl | 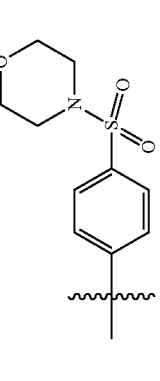 | H | 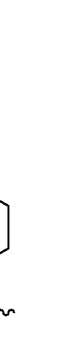 | O |

TABLE A-continued
| Compound No. | R¹ | R² | R³ | R⁴ | R⁵ | Y |
|---|---|---|---|---|---|---|
| 232 | H | Cl | 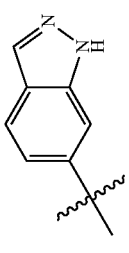 | H | 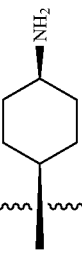 | O |
| 233 | H | 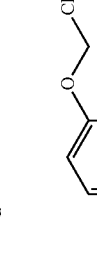 |  | H | 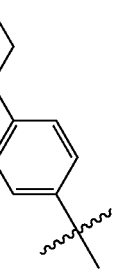 | O |
| 234 | H | 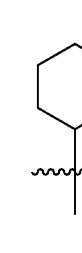 | 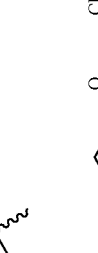 | H | 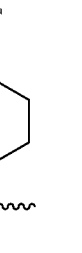 | O |
| 235 | H | 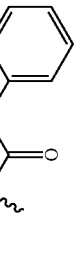 |  | H |  | O |
| 236 | H |  |  | H |  | S |
| 237 | H |  |  | H |  | S |

TABLE A-continued
| Compound No. | R¹ | R² | R³ | R⁴ | R⁵ | Y |
|---|---|---|---|---|---|---|
| 238 | H | 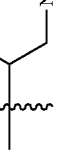 | 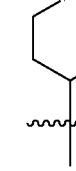 | H | 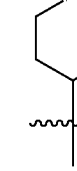 | O |
| 239 | H | H | 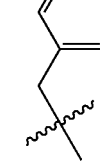 | CH₃ |  | O |
| 240 | H | H |  | CH₃ |  | O |
| 241 | H | H | 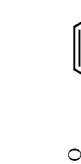 | CH₃ |  | O |
| 242 | H | H |  | CH₃ |  | O |

TABLE A-continued

| Compound No. | R¹ | R² | R³ | R⁴ | R⁵ | Y |
|---|---|---|---|---|---|---|
| 243 | H | H | 4-(2-methoxyethoxy)phenyl | CH₃ | but-3-enyl (branched) | O |
| 244 | H | H | 4-(2-methoxyethoxy)phenyl | CH₃ | (piperidin-3-yl)methyl | O |
| 245 | H | H | 4-(2-methoxyethoxy)phenyl | CH₃ | (piperidin-2-yl)methyl | O |
| 246 | H | H | 4-(2-methoxyethoxy)phenyl | CH₃ | methoxycarbonylmethyl (branched) | O |
| 247 | H | H | 4-(2-methoxyethoxy)phenyl | CH₃ | 2-methoxyethyl (branched) | O |

TABLE A-continued

| Compound No. | R¹ | R² | R³ | R⁴ | R⁵ | Y |
|---|---|---|---|---|---|---|
| 248 | H | H | 4-(2-methoxyethoxy)phenyl | CH₃ | 2-(2-oxopyrrolidin-1-yl)ethyl | O |
| 249 | H | H | 4-(2-methoxyethoxy)phenyl | CH₃ | (pyridin-2-yl)methyl | O |
| 250 | H | H | 4-(2-methoxyethoxy)phenyl | CH₃ | cyclopentylmethyl | O |
| 251 | H | H | 4-(2-methoxyethoxy)phenyl | CH₃ | tetrahydro-2H-pyran-4-yl | O |
| 252 | H | H | 4-(2-methoxyethoxy)phenyl | CH₃ | (tetrahydrofuran-3-yl)methyl | O |
| 253 | H | H | 4-(2-methoxyethoxy)phenyl | CH₃ | 1-methylpiperidin-4-yl | O |

TABLE A-continued
| Compound No. | R¹ | R² | R³ | R⁴ | R⁵ | Y |
|---|---|---|---|---|---|---|
| 254 | H | H | 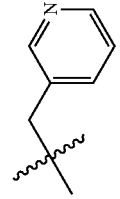 | CH₃ | 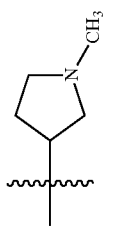 | O |
| 255 | H | H | 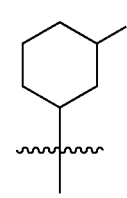 | CH₃ | 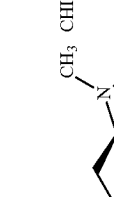 | O |
| 256 | H | H | 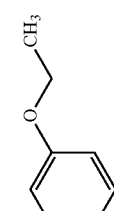 | CH₃ | 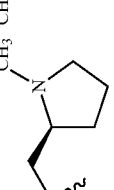 | O |
| 257 | H | H | 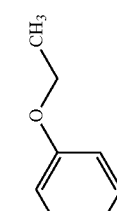 | CH₃ | 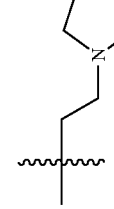 CHIRAL | O |
| 258 | H | H | 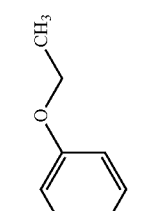 | CH₃ | 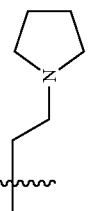 | O |

TABLE A-continued
| Compound No. | R¹ | R² | R³ | R⁴ | R⁵ | Y |
|---|---|---|---|---|---|---|
| 259 | H | H | 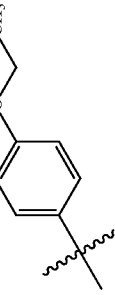 | CH₃ | 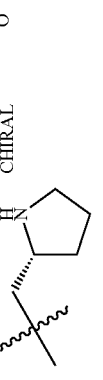 | O |
| 260 | H | H | 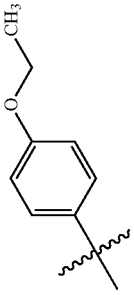 | CH₃ |  | O |
| 261 | H | H | 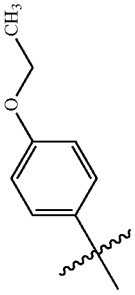 | CH₃ | 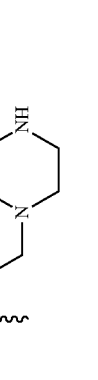 | O |
| 262 | H | H | 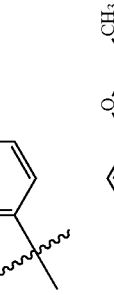 | CH₃ | 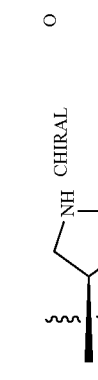 | O |
| 263 | H | H | 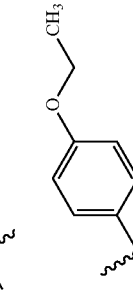 | CH₃ |  | O |
| 264 | H | H |  | CH₃ |  | O |

TABLE A-continued
| Compound No. | R¹ | R² | R³ | R⁴ | R⁵ | Y |
|---|---|---|---|---|---|---|
| 265 | H | H | 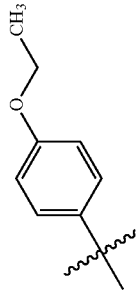 | CH₃ | 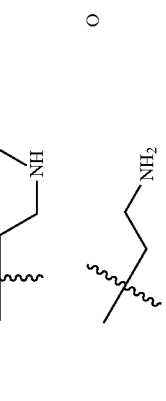 | O |
| 266 | H | H | 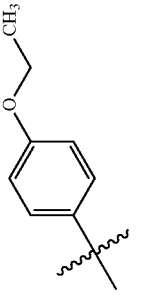 | CH₃ | 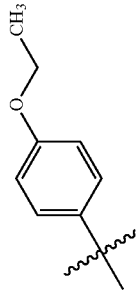 CHIRAL | O |
| 267 | H | H | 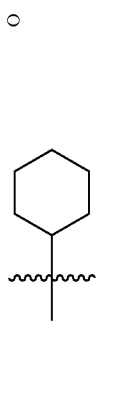 | CH₃ | 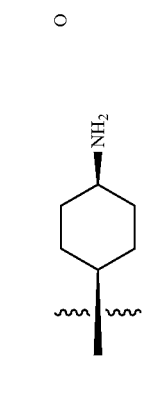 CHIRAL | O |
| 268 | H | H | 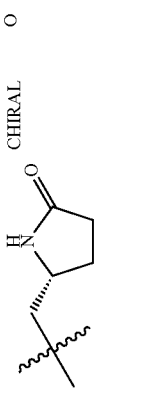 | CH₃ | 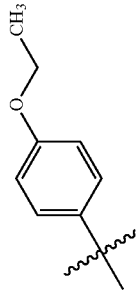 | O |
| 269 | H | H | 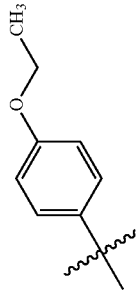 | CH₃ |  | O |
| 270 | H | H | 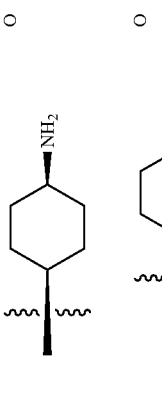 | CH₃ | 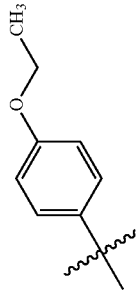 | O |
| 271 | H | H | 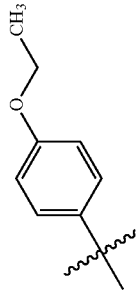 | CH₃ |  | O |

TABLE A-continued
| Compound No. | R¹ | R² | R³ | R⁴ | R⁵ | Y |
|---|---|---|---|---|---|---|
| 272 | H | H | 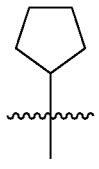 | CH₃ | 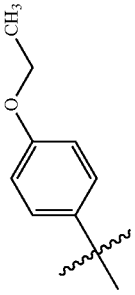 | O |
| 273 | H | H | 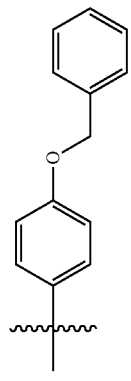 | Ph | 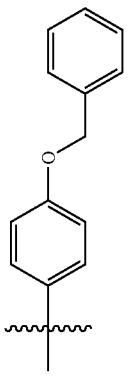 | O |
| 274 | H | H | 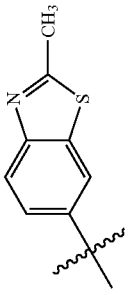 | Ph | (trans-4-aminocyclohexyl) | O |
| 275 | H | H | (4-benzyloxyphenyl) | Ph | (piperidin-3-yl) | O |
| 276 | H | H | (2-methylbenzothiazol-6-yl) | CH₃ | (piperidin-3-yl) | S |

In a second aspect, the present invention provides a compound of formula II-20 which is useful as synthetic intermediate for a compound of formula I:

1) A compound of the formula II-20

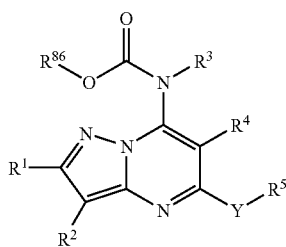
(II-20)

wherein $R^1$-$R^5$ and Y are as defined in claim 1; $R^{86}$ is C1-C8 optionally substituted alkyl or optionally substituted arylalkyl;
$R^{86}$ is preferably tert-butyl or benzyl.

The pyrazolo[1,5-α]pyrimidine derivatives represented by formula I above exist as tautomers represented by the following formula XI:

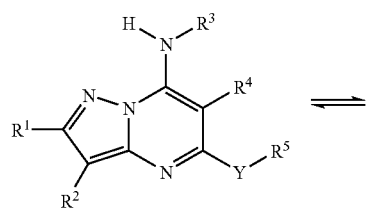 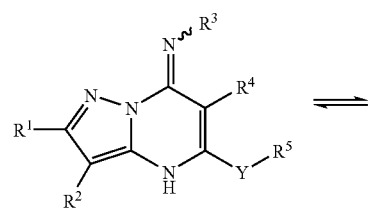 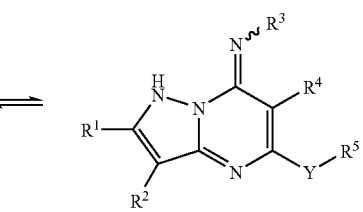
(XI)

wherein $R^1$-$R^5$ and Y are as defined for formula I above;

These tautomers are also encompassed within the scope of the present invention.

In a third aspect, the present invention provides a process for the manufacture of a compound of the invention by reaction of a compound of formula II, II-02, I-01, III, IV, V, VI, VII, II-05, II-07, II-09, II-18, V-01, V-02, II-11, II-13, II-15, II-03, V-03, IV-03, I-04 or V-06 as follows, wherein $R^1$-$R^5$, $R^7$, $R^{18}$, $R^{36}$, $R^{37}$, $R^{44}$, $R^{45}$ and Y are as defined above, $R^6$ is substituents of heterocyclyl as defined in above (1) as "substituted heterocyclyl", "Cbz", "Boc" and "Ac" mean "benzyloxycarbonyl", "tert-butoxycarbonyl" and "acetyl" respectively:

1) reacting a compound of the formula II

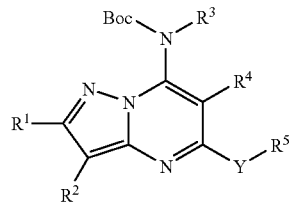
(II)

with acid egg. trifluoroacetic acid or hydrochloric acid for removal of tert-butoxycarbonyl groups of a compound (for example as described in Protective Groups in Organic Synthesis, 3rd Ed, John Wiley & Sons Inc); Y represents O or S.

2) reacting a compound of the formula II-02

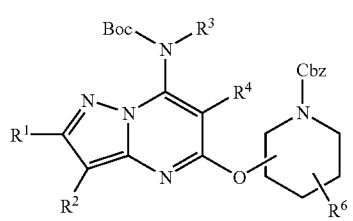
(II-02)

with iodo trimethylsilane for removal of carbonate groups of a compound (for example as described in Protective Groups in Organic Synthesis, 3rd Ed, John Wiley & Sons Inc)

3) reacting a compound the formula I-01

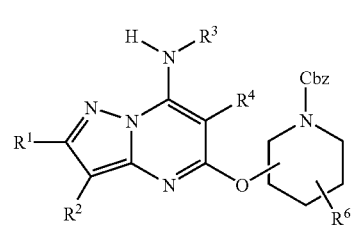
(I-01)

with hydrogen in the presence of palladium on carbon for removal of benzyloxy carbonyl group of a compound (for example as described in Protective Groups in Organic Synthesis, 3rd Ed, John Wiley & Sons Inc)

4) reacting a compound of the formula III

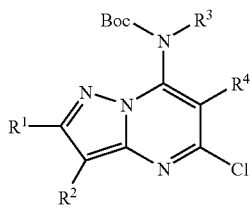
(III)

with an alkoxide or tiolate (alcohol or thiol with sodium hydride)

5) reacting a compound of the formula III

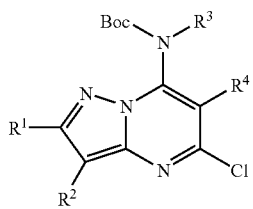
(III)

with xanthate followed by hydrolysis 6) reacting a compound of the formula IV

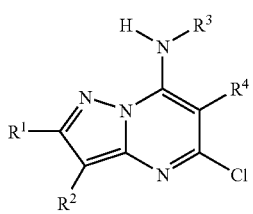
(IV)

with di tert-butyl dicarbonate (for example as described in Protective Groups in Organic Synthesis, 3rd Ed, John Wiley & Sons Inc)

7) reacting a compound of the formula V

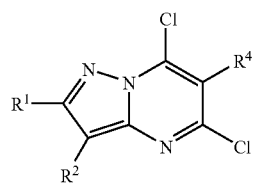
(V)

with a compound of the formula $R^3NH_2$ or $R^3NHAc$ in the presence of base e.g. triethylamine and sodium hydride 8) reacting a compound of the formula VI

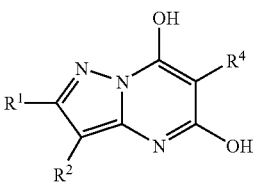
(VI)

with a halogenating agent e.g. phosphorus oxychoride or phenyl phosphonic dichlioride (for example as described in U.S. Pat. No. 3,907,799 (CA 1975, 84, 4998p), J. Med. Chem. 1977, 20, 296, Monatsh Chem. 1986, 117, 1305.)

9) reacting a compound of the formula VII

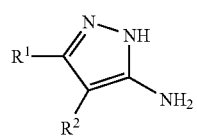
(VII)

with a compound of the formula $R^4CH(CO_2CH_3)_2$ or $R^4CH(CO_2CH_2CH_3)_2$ (for example as described in J. Med. Chem. 1976, 19, 296 and J. Med. Chem. 1977, 20, 296.)

10) reacting a compound of the formula II-05

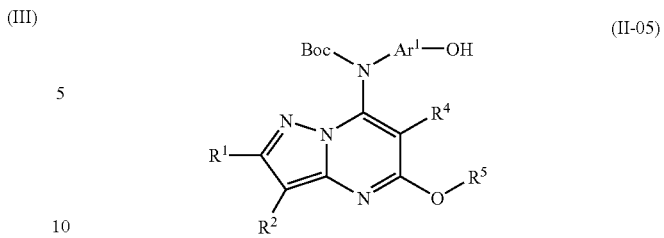
(II-05)

with an alcohol derivative in the presence of condensing agents e.g. combination of diisopropyl azodicarboxylate and polymer supported triphenylphosphine under e.g Mitsunobu reaction conditions (for example as described in Synthesis 1981, 1.); $Ar^1$ represents C6-C14 optionally substituted awyl or optionally substituted heteroaryl 11) reacting a compound of the formula II-07

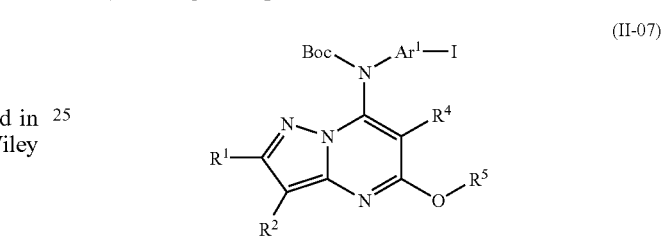
(II-07)

with boronic acid derivative in the presence of transition metal catalyst under e.g. Suzuki coupling conditions (for example as described in Chem. Rev. 1995, 95, 2457.); $Ar^1$ represents C6-C14 optionally substituted aryl or optionally substituted heteroaryl 12) reacting a compound of the formula II-09

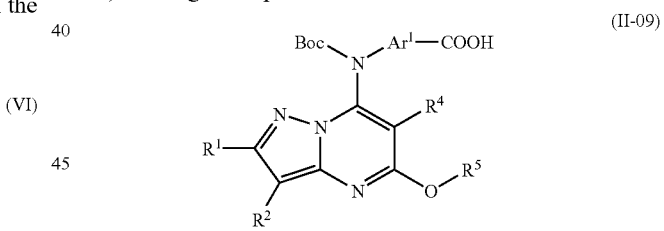
(II-09)

with a compound of the formula $R^{17}R^{18}NH$ in the presence of peptide coupling agent; $Ar^1$ represents C6-C14 optionally substituted aryl or optionally substituted heteroaryl 13) reacting a compound of the formula II-18

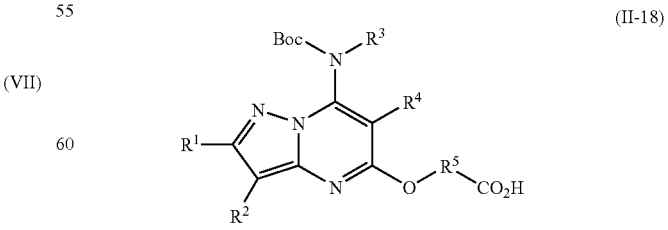
(II-18)

with a compound of the formula $R^{36}R^{37}NH$ in the presence of peptide coupling agent 14) reacting a compound of the formula V-01

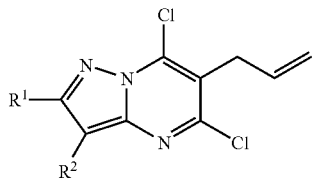
(V-01)

with boran followed by hydrogen peroxide 15) reacting a compound of the formula V-02

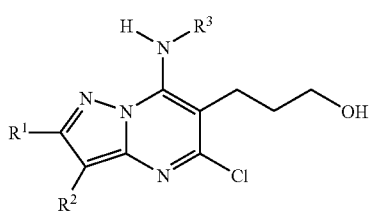
(V-02)

with silylating agents e.g. chioro tert-butyl dimethyl silane (for example as described in Protective Groups in Organic Synthesis, 3rd Ed, John Wiley & Sons Inc)

16) reacting a compound of the formula II-11

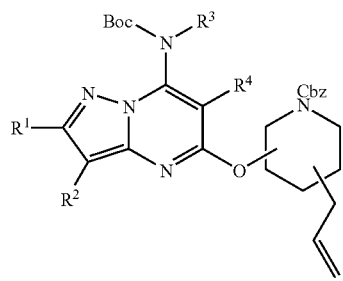
(II-11)

with sodium periodate in the presence of osmium tetroxide (J. Org. Chem., 1956, 21, 478)

17) reacting a compound of the formula II-13

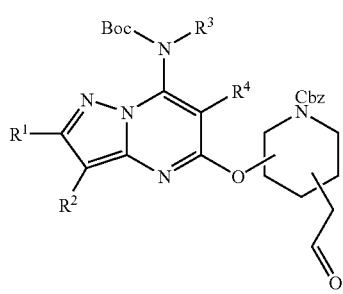
(II-13)

with reducing agents for the aldehyde e.g. sodium borohydride 18) reacting a compound of the formula II-13

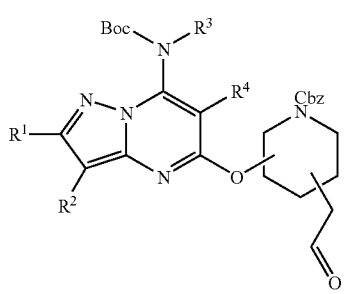
(II-13)

with oxidizing agents e.g sodium chlorite under Kraus oxidation conditions 19) reacting a compound of the formula II-15

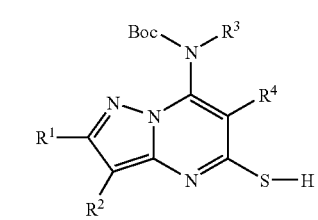
(II-15)

with a compound of formula $R^{44}R^{45}NH$ in the presence of peptide coupling agent e.g. O-(7-azabenzotriazol-1-yl) N,N,N,N',N'-tetrametliylurorium hexafiluorophosphate 20) reacting a compound of the formula II-03

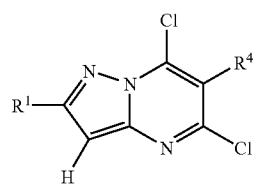
(II-03)

with a formula $R^5$—$OSO_2CH_3$ in the presence of base 21) reacting a compound of the formula V-03

(V-03)

with a halogenating agent e.g. N-chlorosuccinimide, N-bromosuccinimide (for example as described in J. Med. Chem. 1976, 19, 517.) or iodine monochioride 22) reacting a compound of the formula V-03

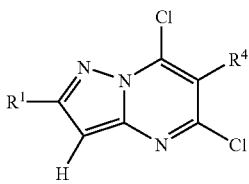

with a thiocyanating agent e.g, combination of potassium thiocyanate and bromine 23) reacting a compound of the formula V-03

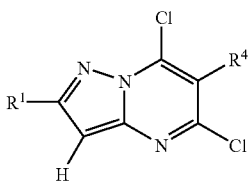

with an acylating agent e.,g. dimethyl formamide/phosphorus oxychloride or acetyl chloride/aluminium trichloride 24) reacting a compound of the formula IV-03

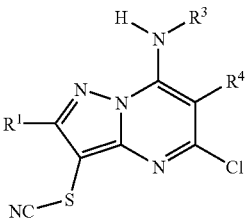

with a Grignard reagent e.g methyl magnesium chloride 25) reacting a compound of the formula I-04

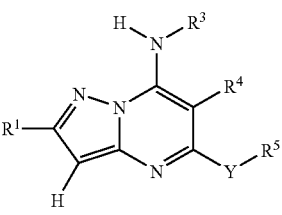

with halogenating agent e.g. iodine monochloride 26) reacting a compound of the formula V-06

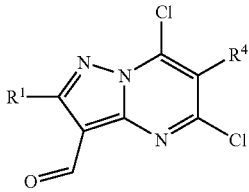

with reducing agent e.g. sodium borohydride or wit diol derivative e.g propane 1,3-diol and ethane 1,2-diol for formation of acetal.

A compound of formula I may undergo 1 or 2 or more further reactions to provide a different compound of formula I. For example, a compound may undergo a reduction, oxidation, elimination, substitution and/or addition reaction.

Figure 2:
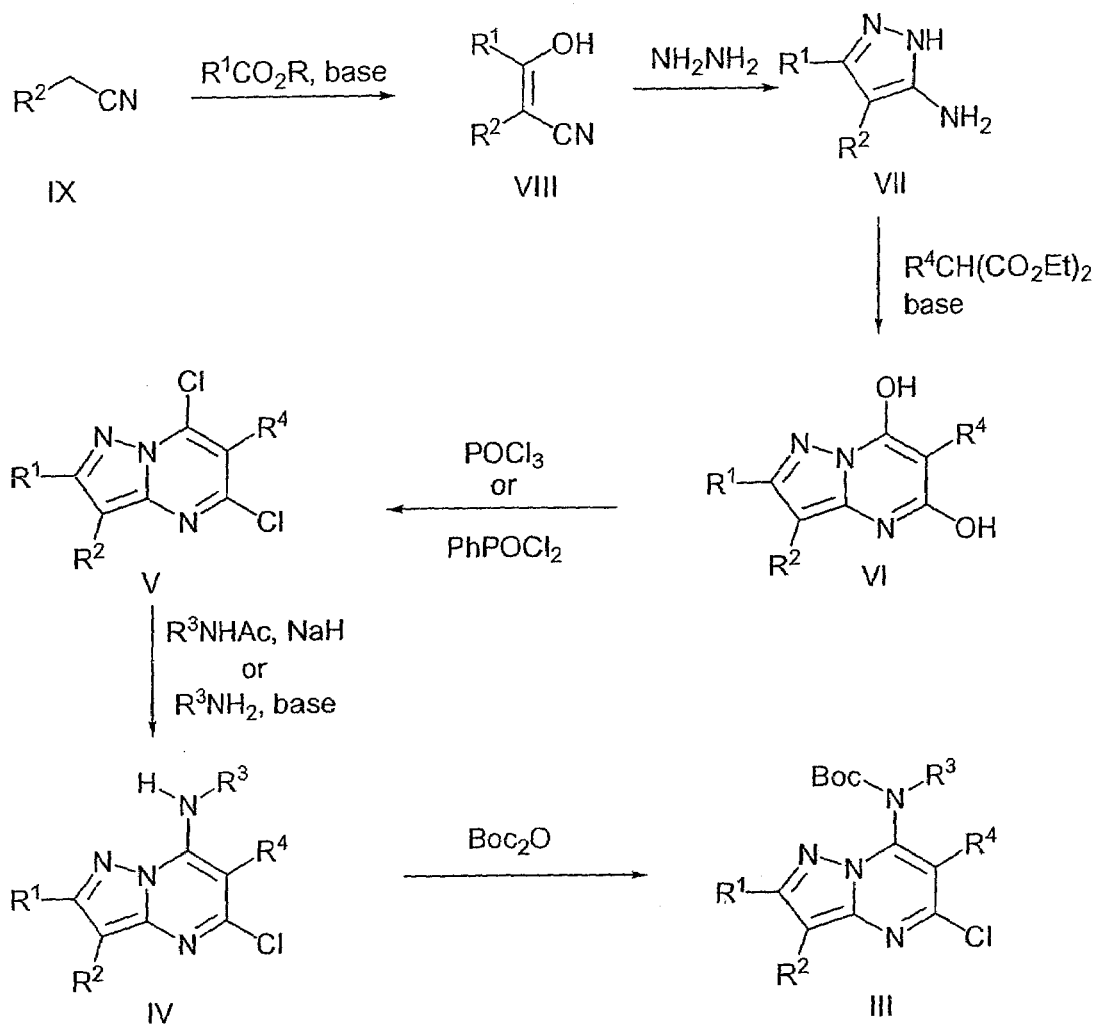
FIGS. 2 to 8 show a general process for synthesizing a compound represented by Formula (I).
Figure 3:
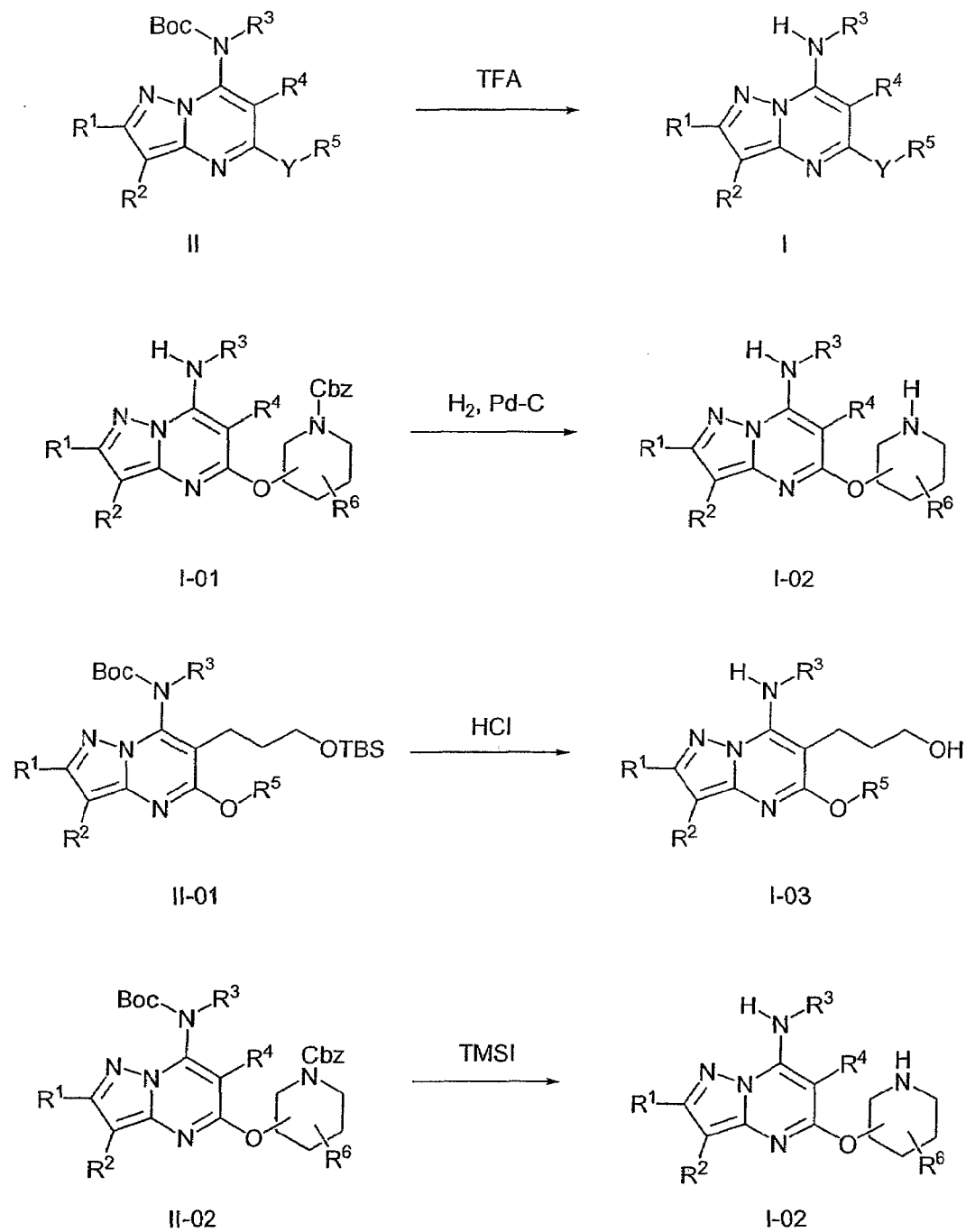
Figure 4:
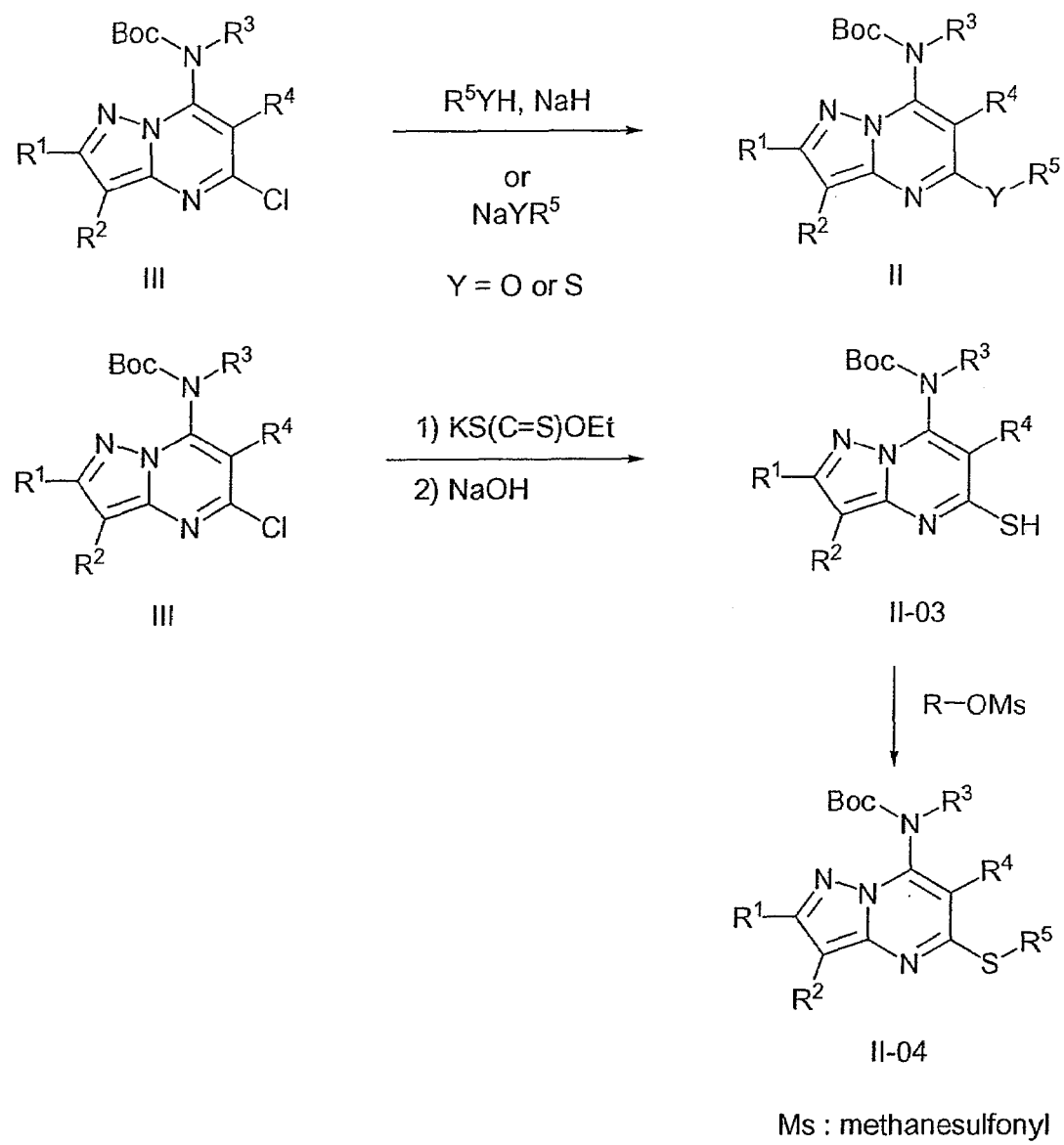
Figure 5:
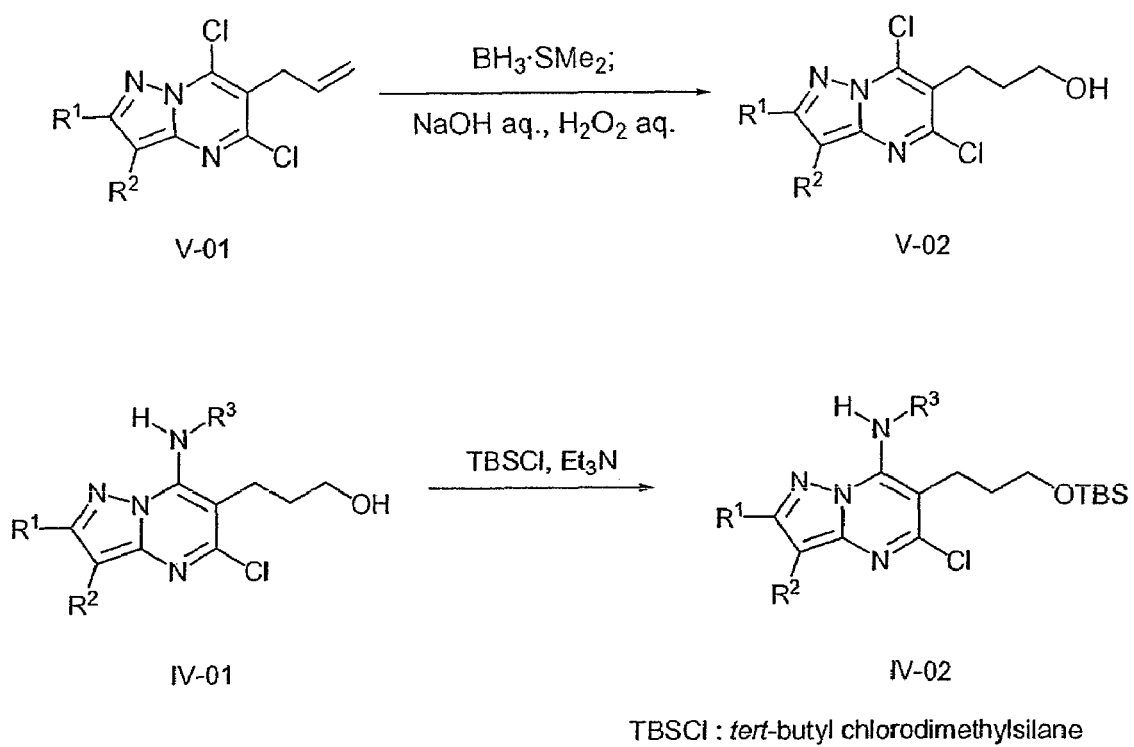
Figure 6:
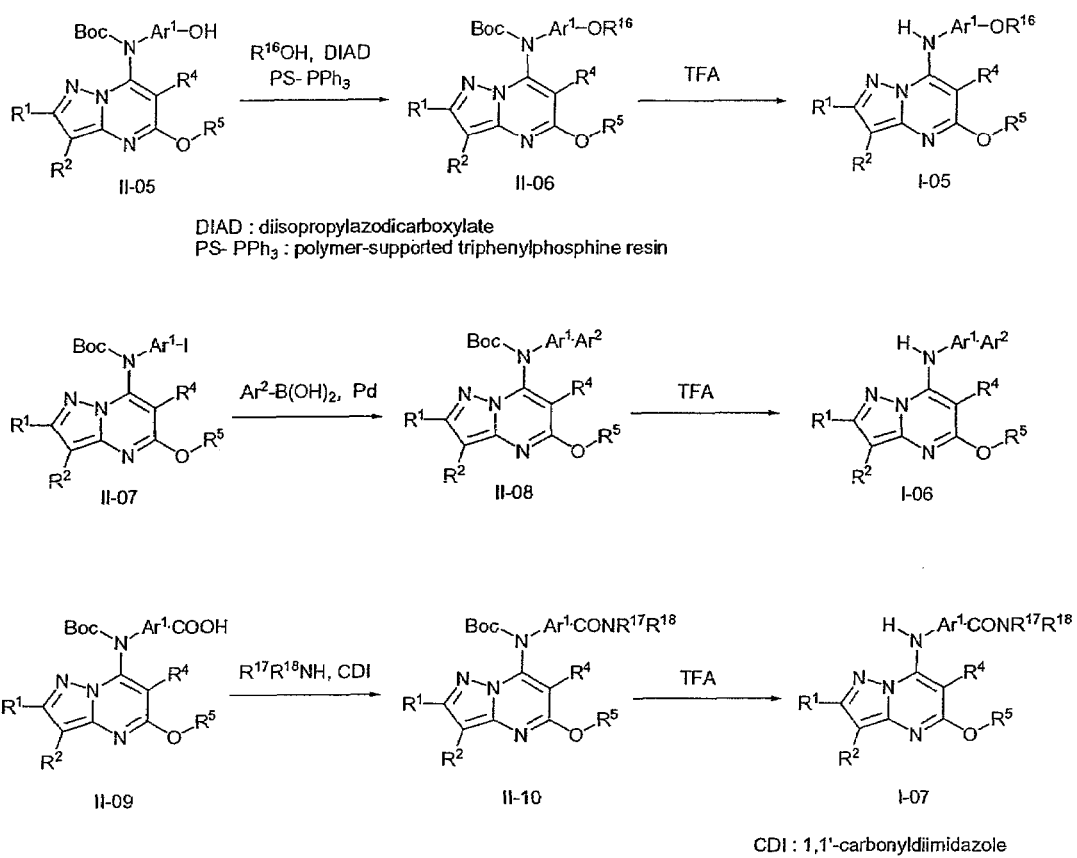
Figure 7:
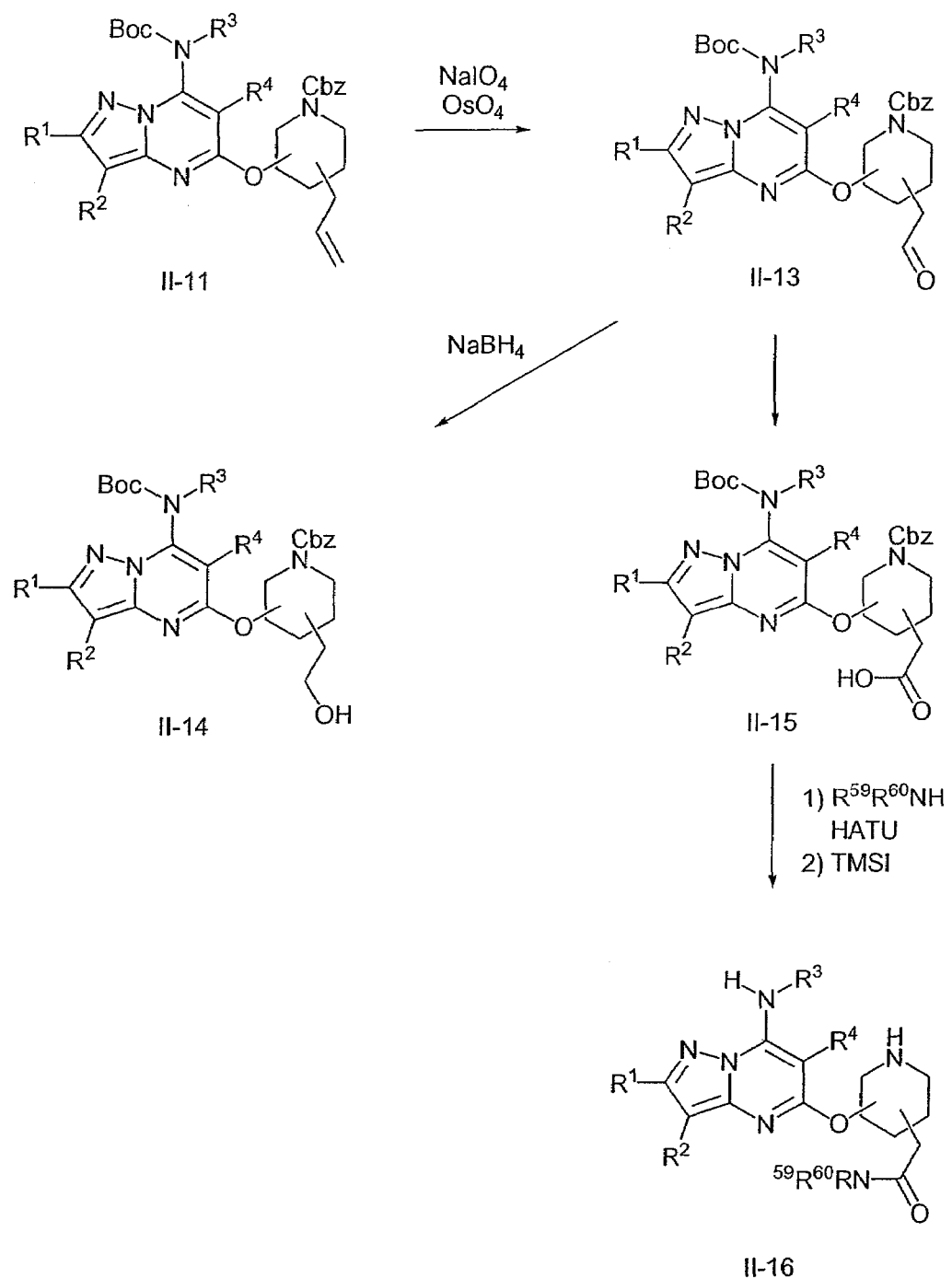
Figure 8:
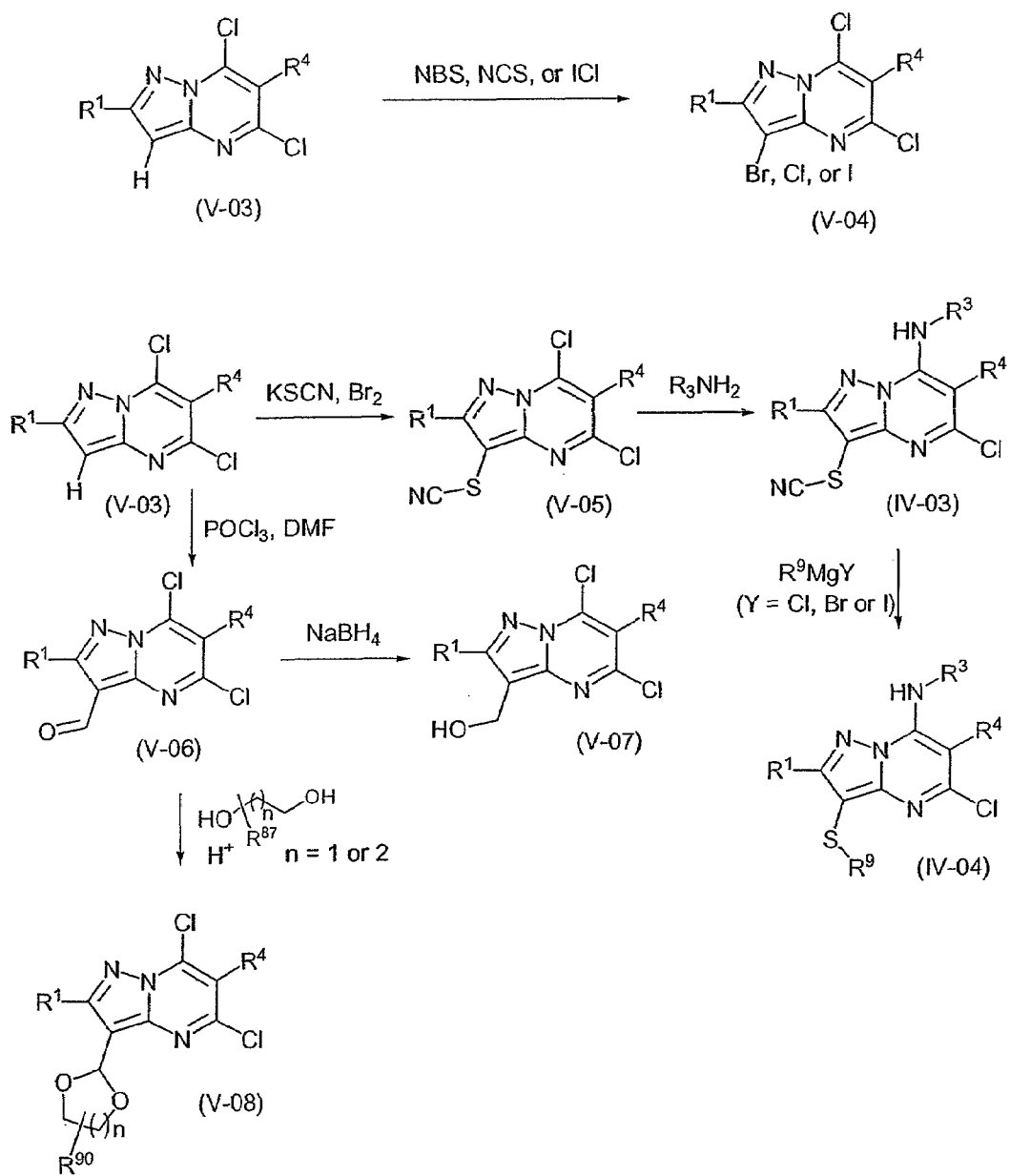

FIG. 2-8 show general reaction schemes for the preparation of compounds of Formula I. In FIG. 2-8 $R^1$-$R^5$, $R^9$, $R^{16}$-$R^{18}$, and Y are as defined above. "Cbz" and "Boc" mean "benzyloxycarbonyl" and "tert-butoxycarbonyl" respectively. $R^6$, $R^{87}$ and $R^{90}$ respectively represent the substituents as defined as "substituents of heterocyclyl" in above (1). $Ar^1$ and $Ar^2$ represent C6-C14 optionally substituted aryl or optionally substituted heteroaryl. $R^{59}$ and $R^{60}$, which may be the same or different, are as defined for $R^8$.

The compounds of formula V, VI, VII, VIII and IX are either known or can be prepared by methods analogous to those known for preparing analogous known compounds.

Other methods will be apparent to the chemist skilled in the art, as will the methods for preparing starting materials and intermediates. The examples also make apparent various methods of preparing compounds of the invention as well as starting materials and intermediates.

In a fourth aspect, the present invention provides a composition comprising a compound of the invention in combination with a pharmaceutically acceptable carrier, diluent or excipient.

The composition may also comprise 1 or 2 or more additional active agents, such as an anti-inflammatory agent (for example a p38 inhibitor, glutamate receptor antagonist, or a calcium channel antagorist), a chemotherapeutic agent and/or an antiproliferative agent.

Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The composition according to the invention for use in the aforementioned indications may be administered by any convenient method, for example by oral (including by inhalation), parenteral, mucosal (e.g buccal, sublingual, nasal), rectal or transdermal administration and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdernal administration include ointments, gels, patches and injections including powder injections.

Conveniently the composition is in unit dose form such as a tablet, capsule or ampoule.

In a fifth aspect, the present invention provides a process for the manufacture of a composition according of the invention which comprises admixing 1 or 2 or more compounds of the invention with 1 or 2 or more pharmaceutically acceptable excipients, carriers or diluents. The manufacture can be carried out by standard techniques well known in the art and involves combining a compound according to the first aspect of the invention and the pharmaceutically acceptable carrier or diluent. The composition may be in any form including a tablet, a liquid, a capsule, and a powder or in the form of a food product, e.g. a finctional food. In the latter case the food product itself may act as the pharmaceutically acceptable carrier.

In a sixth aspect, the present invention provides a compound or composition of the invention, for use in medicine.

The compounds of the present invention are inhibitors of mitogen-activated protein kinase-activated protein kinase 2 (MAPKAP-K2). For the purpose of this invention, an inhibitor is any compound which reduces activity or prevents the activation of MAPKAP-K2.

The compounds are therefore useful for conditions for which inhibition of MAPKAP-K2 activity is beneficial. Thus, preferably, this aspect provides a compound of the first aspect or a composition of the third aspect of the present invention, for the prevention or treatment of MAPKAP-K2-mediated disorder. The compounds of the first aspect of the invention may thus be used for the inhibition of MAPKAP-K2.

A "MAPKAP-K2-mediated disorder" is any disease or deleterious condition in which MAPKAP-K2 plays a role. Examples include neurodegenerative/neurological disorder (including dementia), inflammatory disease, sepsis, autoimmune disease, destructive bone disorder, diabetes, cancer, ischemia reperfiusion injury, angiogenic disorder, cachexia, obesity, angiogenesis and/or chronic obstructive puhnonary disease (COPD).

The compounds of the present invention are particularly usefiu for the prevention or treatment of a neurodegenerative disorder. In particular, the neurodegenerative disorder results from apoptosis and/or inflammation. Examples of neurodegenerative disorders are: dementia; Alzheimer's disease; Parkinson's disease; Amyotrophic Lateral Sclerosis; Huntington's disease; senile chorea; Sydenham's chorea; hypoglycemia; head and spinal cord trauma including traumatic head injury; acute and chronic pain; epilepsy and seizures; olivopontocerebellar dementia; neuronal cell death; hypoxia-related neurodegeneration; acute hypoxia; glutamate toxicity including glutamate neurotoxicity; cerebral ischemia; dementia linked to meningitis and/or neurosis; cerebrovascular dementia; or dementia in an HIV-infected patient.

The compounds of the invention can also be used to prevent or treat disorders resulting from inflammation. These include, for example, inflammatory bowel disorder, bronchitis, acute pancreatitis, chronic pancreatitis, allergies of various types, and possibly Alzheimer's disease. Autoimmune diseases which may also be treated or prevented by the compounds of the present invention include rheumatoid arthritis, systemic lupus erthematosus, Sjdgren syndrome, psoriatic arthritis, glomerulonephritis, scleroderma, chronic thyroiditis, Graves's disease, autoimmune gastritis, diabetes, autoimmune haemolytis anaemia, autoimmune neutropaenia, thrombocytopenia, atopic dermatitis, chronic active hepatitis, myasthenia gravis, multiple sclerosis, ulcerative colitis, Crohn's disease, psoriasis, graft vs host disease, ankylosing spondylitis or juvenile rheumatoid arthritis.

A compound of the present invention may be administered simultaneously, subsequently or sequentially with 1 or 2 or more other active agent, such as an anti-inflammatory agent e.g. p38 inhibitor, glutamate receptor antagonist, calcium channel antagonist, a chemotherapeutic agent or an antiproliferative agent. For example, for acute treatment, a p38 inhibitor may be administered to a patient prior to administering a compound of the present invention The compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g between 1 and 25 mg of the compound of the formula I, or a physiologically acceptable salt thereof calculated as the free base, the compound being administered 1 to 4 times per day. Suitably the compounds will be administered for a period of continuous therapy, for example for a week or more.

In a seventh aspect, the present invention provides a method of treating or preventing MAPKAP-K2-mediated disorder in an individual, which method comprises administering to said individual 1 or 2 or more compounds of the invention or a composition of the invention. The active compound is preferably administered in a cumulative effective amount. The individual may be in need of the treatment or prevention. Any of MAPKAP-K2-mediated disorder listed above in relation to the fifth aspect may be the subject of treatment or prevention according to the sixth aspect. 1 or 2 or more other active agent may be administered to the individual simultaneously, subsequently or sequentially to administering the compound. The other active agent may be an anti-inflammatory agent such as a p38 inhibitor, glutamate receptor antagonist, calcium channel antagonist, a chemotherapeutic agent or an antiproliferative agent.

In an eighth aspect, the present invention provides the use of a compound of the invention in the manufacture of a medicament for the prevention or treatment of MAPKAP-K2-mediated disorder. The medicament may be used for treatment or prevention of any of MAPKAP-K2-mediated disorder listed above in relation to the fifth aspect. Again, the compounds of the present invention may be administered simultaneously, subsequently or sequentially with 1 or 2 or more other active agent such as a p38 inhibitor.

In a ninth aspect, the present invention provides an assay for determining the activity of the compounds of the present invention, comprising providing a system for assaying the activity and assaying the activity of the compound. Preferably the assay is for MAPKAP-K2 inhibiting activity of the compound. The compounds of the invention may be assayed in vitro, in vivo, in silico, or in a primary cell culture or a cell line. In vitro assays include assays that determine inhibition of the kinase activity of activated MAPKAP-K2. Alternatively, in vitro assays may quantitate the ability of a compound to bind MAPKAP-K2 and may be measured either by radiolabelling the compound prior to binding, then isolating the inhibitor/ MAPKAP-K2 complex and determining the amount of the radiolabel bound or by running a competition experiment where new inhibitors are incubated with MAPKAP-K2 bound to known radioligands. An example of an assay which may be used is Scintillation Proximity Assay (SPA), preferably using radiolabelled ATP. Another example is ELISA.

In a tenth aspect, the present invention provides a method of inhibiting the activity or function of MAPKAP-K2, which method comprises exposing MAPKAP-K2 to a compound or a composition of the invention. The method may be performed in a research model, in vitro, in silico, or in vivo such as in an animal model. A suitable animal model may be a kainic acid model in rat or mice, traumatic brain injury model in rat, or MPTP in mice for neurodegenerative disorder and adjuvant arritis or collagen induced arthritis in rat or mice, type II collagen-antibodies induced arthritis in mice, or a LPS induced endotoxin shock model in rat or mice for inflammatory disease.

All features of each of the aspects apply to all other aspects mutatis mutandis.

EXAMPLES

Hereinafter, the present invention is explained based on the specific examples, but the invention is not limited to these examples. The numbers assigned to each of the compounds in the following examples correspond to the Compound Nos. assigned to the compounds listed as suitable examples in the above-mentioned Table A. Structures of isolated novel compounds were confirmed by $^1$H-NMR and/or mass spectrometry using single quadrupole instrumentation equipped with an electron spray source and other suitable analytical methods.

For the $^1$H-NMR spectra (400 MHz, DMSO-$d_6$ or CDCl$_3$), the chemical shift (δ: ppm) and coupling constant (J:Hz) are shown. For the results of mass spectrometry, observed values are shown as M+H, that is, a value in which a proton (H) is attached to the compound molecular mass (M). In addition, "HPLC retention time" represents the retention time (unit: min) of a compound in the HPLC analysis under the following analytical conditions. Also, values of the melting point (mp) are uncorrected. (d) denotes decomposition at the melting point or near the melting point.

HPLC (High Performance Liquid Chromatography) conditions

Measurement system: Hewlett-Packard 1100 HPLC

Column: Cadenza CD-C18 (Imtakt) 100 mm×4.6 mm (inside diameter)

(Method A)

| Solvent: | A: | $H_2O$/acetonitrile = 95/5 |
| --- | --- | --- |
| | | 0.05% TFA (trifluoroacetic acid) |
| | B: | $H_2O$/acetonitrile = 5/95 |
| | | 0.05% TFA (trifluoroacetic acid) |

Flow rate, 1.0 mL/min

Gradient:
0-1 min, solvent B: 10%, solvent A: 90%
1-13 min, solvent B: 10%→70%, solvent A: 90%→30%
13-14 min, solvent B: 70%→100%, solvent A. 30%→0%
14-16 min, solvent B: 100%, solvent A: 0%
16-19 min, solvent B: 100%→10%, solvent A: 0%→90%

Calculation of purity: Area % of NV absorption (254 nm)

(Method B)

| Solvent: | A: | $H_2O$ /acetonitrile = 95/5 |
| --- | --- | --- |
| | | 0.05% TFA (trifluoroacetic acid) |
| | B: | $H_2O$ /acetonitrile = 5/95 |
| | | 0.05% TFA (trifluoroacetic acid) |

Flow rate: 1.0 mL/min

Gradient:
0-1 min, solvent B: 5%, solvent A: 95%
1-13 min, solvent B: 5%→55%, solvent A: 95%→45%
13-14 min, solvent B: 55%→100%, solvent A: 45%→0%
14-17 min, solvent B: 100%, solvent A: 0%
17-18 min, solvent B: 100%→5%, solvent A: 0% →95%

Calculation of purity: Area % of UV absorption (254 nm)

(Method C)

| Solvent: | A: | $H_2O$/acetonitrile = 95/5 |
| --- | --- | --- |
| | | 0.1% NEt$_3$(triethylamine) |
| | B: | $H_2O$/acetonitrile = 5/95 |
| | | 0.1% NEt$_3$(triethylamine) |

Flow rate: 1.5 ml/min

Gradient:
0-1 min, solvent B: 10%, solvent A: 90%
1-13 min, solvent B: 10%→100%, solvent A: 90%→0%
13-16 min, solvent B: 100%, solvent A: 0%
16-19 min, solvent B: 100%→10%, solvent A: 0%→90%

Calculation of purity: Area % of UV absorption (254 nm)

Purification by preparative HPLC was performed using the following solvent systems under the conditions of suitable concentration gradients. In addition, a compound obtained by purification by preparative HPLC may form a salt with trifluoroacetic acid.

| Solvent: | A: | H₂O/acetonitrile = 95/5 |
| | | 0.05% TFA (trifluoroacetic acid) |
| | B: | H₂O/acetonitrile = 5/95 |
| | | 0.05% TFA (trifluoroacetic acid) |

Example 1

A General Procedure for the Synthesis of a Pyrazolo[1,5-a]pyrimidine Compound represented by General Formula (VI)

A mixed solution was prepared by dissolving sodium ethoxide (50 mmol) in ethanol (100 mL) and then by adding 2-substituted malonic acid diester (20 mmol) and appropriately substituted 3-aminopyrazole (VII) (20 mmol). The reaction was carried out by stirring the mixed solution under heating and reflux for 13 hrs, yielding a precipitate Note). The reaction solution was cooled to room temperature and the precipitate was filtered out through an A4-glass filter. After washing the precipitate with a small amount of cooled ethanol, the residue was dried under vacuum. The dried solid was dissolved in water (ca. 100 mL), which was acidified (pH 2) by adding concentrated hydrochloric acid and then the resulting precipitate was filtered off. After washing the precipitate with water, it was dried under vacuum to obtain the target compound (VI). The typical yield of the reaction ranged from 60 to 80%. Note) In several cases where the substituent was an alkyl chain, little if any precipitate was formed. In these compounds, after removing ethanol under vacuum, water and ethyl acetate were added to the residue. After separating the aqueous layer, it was acidified (pH 2) by adding concentrated hydrochloric acid and then the resulting precipitate was filtered off. After washing the precipitate with water, it was dried under vacuum to obtain the target compound (VI).

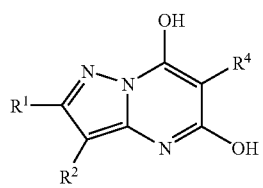

(VI)

| Compound No. | R¹ | R² | R⁴ | mp (° C.) or ¹H-NMR |
|---|---|---|---|---|
| VI-01 | Me | H | H | mp 240 (d) |
| VI-02 | H | H | Ph | mp 285 |
| VI-03 | H | H | Et | mp 260, ¹H-NMR(400 MHz, DMSO-d₆)δ: 7.74(d, 1H), 5.87(d, 1H), 2.39 (q, 2H), 0.97(t, 3H). |
| VI-04 | H | H | allyl | ¹H-NMR(400 MHz, CDCl₃)δ: 7.77(d, J=2.0Hz, 1H), 5.90(d, J=2.0Hz, 1H), 5.85-5.75(m, 1H), 4.98-4.87(m, 2H), 3.12(d, J=5.9Hz, 2H). |
| VI-05 | H | H | Me | ¹H-NMR(400 MHz, DMSO-d₆)δ: 7.74(d, J=2.0Hz, 1H), 5.88(d, J=2.0Hz, 1H), 1.85(s, 3H). |
| VI-06 | H | COOEt | H | ¹H-NMR(400 MHz, DMSO-d₆)δ: 8.06(s, 1H), 5.06(s, 1H), 4.27(q, J=7.1Hz, 2H), 1.28(t, J=7.1Hz, 3H). |

Example 2

A General Procedure for the Synthesis of a Pyrazolo[1,5-a]pyrimidine Compound represented by General Formula (V)

A mixed solution was prepared by adding N,N-dimethylaniline (2 mL) and phosphorus oxychloride (or phenylphosphonic dichloride) (20 mL) to an appropriately substituted 5,7-dihydroxypyrazolo[1,5-a]pyrimnidine derivative (VI) (2 g). The reaction was carried out by stirring the mixed solution under heating and reflux for 18 hrs, and then an excess amount of phosphorus oxychloride (or phenylphosphonic dichloride) was removed under vacuum. The residue was poured into ice (50 g), and extraction was performed with methylene chloride. The organic layer was adsorbed on neutral (activity 1) alumina, followed by purification by column chromatography (the eluent is 0-30% ethyl acetate/hexane) to obtain the target compound (V), a 5,7-dichloropyrazolo[1,5-a]pyrimidine derivative. The typical yield of the reaction ranged from 40 to 50%.

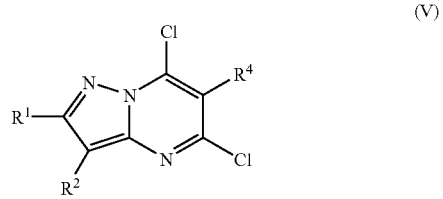

(V)

| Compound No. | R¹ | R² | R⁴ | mp (° C.) or ¹H-NMR |
|---|---|---|---|---|
| V-09 | Me | H | H | mp 92-95 |
| V-10 | H | H | Ph | mp 82-186 |
| V-11 | H | H | Et | mp 60-62, ¹H-NMR(400 MHz, CDCl₃)δ: 8.17(d, J=2.4Hz, 1H), 6.70(d, J=2.4Hz, 1H), 3.00(q, J=7.5Hz, 2H), 1.29(t, J=7.5Hz, 3H). |
| V-12 | H | H | Me | ¹H-NMR(400 MHz, CDCl₃)δ: 8.16(d, J=2.4Hz, 1H), 6.70(d, J=2.4Hz, 1H), 2.56(s, 3H). |
| V-13 | H | H | ⸺CH₂⸺CH=CH₂ | ¹H-NMR(400 MHz, CDCl₃)δ: 8.19(d, J=2.2Hz, 1H), 6.72(d, J=2.2Hz, 1H), 5.98-5.88(m, 1H), 5.20-5.13(m, 2H), 3.72(d, J=6.1Hz, 2H) |
| V-15 | H | Bn | Me | ¹H-NMR(400 MHz, CDCl₃)δ: 7.95(s, 1H), 7.31-7.18(m, 5H), 4.13(s, 2H), 2.54(s, 3H). |
| V-16 | H | Me | Me | ¹H-NMR(400 MHz, CDCl₃)δ: 8.01(s, 1H), 2.53(s, 3H), 2.35(s, 3H). |
| V-17 | H | H | H | ¹H-NMR(400 MHz, DMSO-d₆)δ: 8.37(d, J=2.2Hz, 1H), 7.64(s, 1H), 6.86(d, J=2.2Hz, 1H). |
| V-18 | H | COOEt | Me | ¹H-NMR(400 MHz, DMSO-d₆)δ: 8.69(s, 1H), 4.32(q, J=7.1Hz, 2H), 2.49(s, 3H), 1.32(t, J=7.1Hz, 3H) |

Example 3

A General Procedure for the Synthesis of a Pyrazolo[1,5-a]pyrimidine Derivative represented by General Formula (V-04)

A mixture was prepared by adding N-chlorosuccinamide, N-bromosuccinamide or iodine monochloride (0.011 mol) to a chloroform (50 mL) solution containing 5,7-dichloropyrazolo[1,5-a]pyrimidine (V-03) (0.01 mol) at room temperature. The mixture was stirred under heating and reflux until all solid was dissolved and the starting materials disappeared by TLC. The mixture was poured into ice/water to separate the organic layer, which was washed with aqueous $Na_2CO_3$ solution, subsequently dried with $MgSO_4$, and the solvent was removed under vacuum. The residue was purified by silica gel chromatography to obtain 3-halo-5,7-dichloropyrazolol,5-alpyrimidine (V-04). The typical yield of the reaction ranged from 60 to 90%.

| Compound No. | $R^1$ | $R^2$ | $R^4$ | $^1$H-NMR |
|---|---|---|---|---|
| V-14 | H | Br | H | $^1$H-NMR(400 MHz, $CDCl_3$)δ: 8.20(s, 1H), 7.05(s, 1H). |
| V-15 | H | I | Me | $^1$H-NMR(400 MHz, $CDCl_3$)δ: 8.15(s, 1H), 2.60(s, 3H). |

Example 4

A General Procedure for the Synthesis of a Pyrazolo[1,5-a]pyrimidine Compound represented by General Formula (V-05)

Synthesis of {5,7-dichlorofpyrazolo[1,5-a]pyrimidin-3-yl)}thiocarbonitrile

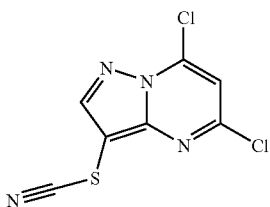

A solution was prepared by slowly adding an acetic acid (3 mL) solution containing bromine (0.72 mL) to an acetic acid (20 mL) solution containing powdered potassium thiocyanate (2.66 g) while maintaining the temperature between 10 and 15° C. To the solution was added an acetic acid (30 mL) solution containing 5,7-dichloropyrazolo[1,5-a]pyrimidine (2.5 g), and the resultant solution was stirred at 15° C. for 30 min and subsequently at room temperature for 3 hrs, and the solvent was removed under vacuum. After adding water and ethyl acetate, the product was extracted with ethyl acetate (three times). The organic layers were combined and dried with $Na_2SO_4$. After removing the solvent under vacuum, the residue was purified by flash chromatography to obtain the title compound (780 mg, purity 73% by $^1$H-NMR);

$^1$H-NMR (400 MHz, $CDCl_3$) δ: 8.27 (s, 1H), 7.10 (s, 1H).

Example 5

A General Procedure for the Synthesis of a Pyrazolo[1,5-a]pyrimidine Compound represented by General Formula (V-06)

Synthesis of 5,7-dichloro-6-methylpyrazolo[1,5-a]pyrimidine-3-carbaldehyde

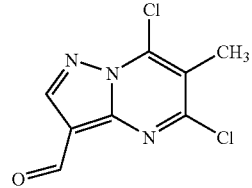

A suspension prepared by adding $POCl_3$ (3 mL) to N,N-dimethylformamide (9 mL) under nitrogen flow at room temperature was stirred for 5 min. To the suspension was slowly added 5,7-dichloro-6-methylpyrazolo[1,5-a]pyrimidine (5 g) and the reaction was carried out by heating the resulting viscous mixture solution at 70° C. for 3 hrs. The reaction mixture was poured into ice and the resultant solution was made alkaline with sodium hydroxide (5 g). The precipitate was filtered off and the dried precipitate was purified by silica gel chromatography (eluting with $CH_2Cl_2 \rightarrow 20\%$ ethyl acetate/$CH_2Cl_2$) to obtain the title compound (3.74 g); the melting point was between 137 and 139° C.

Example 6

A General Procedure for the Synthesis of a Pyrazolo[1,5-a]pyrimidine Compound represented by General Formula (V-07)

Synthesis of {5,7-dichloro-6-methylpyrazolo[1,5-a]pyrimidin-3-yl)}methanol

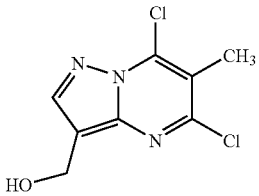

A reaction mixture prepared by slowly adding sodium borohydride (70 mg) to an ethanol solution (20 mL) containing 5,7-dichloro-6-methylpyrazolo[1,5-a]pyrimidine-3-carbaldehyde (200 mg) was stirred at room temperature for 15 min. The reaction mixture was further stirred for 10 min after adding saturated aqueous solution of $NH_4Cl$ (1 mL), and then the solvent was removed under vacuum. After adding water and ethyl acetate, the product was extracted with ethyl acetate (three times). The organic layers were combined, washed with water and then with a saturated aqueous solution of NaCl, followed by drying with $MgSO_4$ to obtain the title compound (150 mg); $^1$H-NMR (400 MHz, $CDCl_3$) δ: 8.22 (s, 1H), 4.90 (s, 1H).

Example 7

A General Procedure for the Synthesis of a Pyrazolo[1,5-a]pyrimidine Compound represented by General Formula (V-08)

Synthesis of 2-{5,7-dichloro-6-methylpyrazolo[1,5-a]pyrimidin-3-yl)}-1,3-dioxane

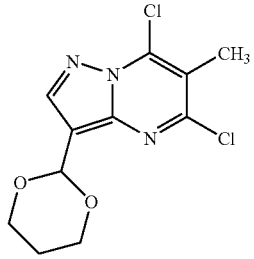

A reaction solution was prepared by adding pyridinium p-toluenesulfonic acid (60 mg) and propane-1,3-diol to a toluene solution (40 mL) containing 5,7-dichloro-6-methylpyrazolo[1,5-a]pyrimidine-3-carbaldehyde (290 mg). The reaction solution was stirred for 2 hrs while removing water by azeotrope under heating and reflux. After cooling the solution, the solvent was removed under vacuum. The residue was purified by silica gel chromatography using ethyl acetate/petroleum ether=2/3 as an eluent to obtain the title compound as a white solid (310 mg); $^1$H-NMR (400 MHz, CDCl$_3$) δ:8.32 (s, 1H), 5.97 (s, 1H), 4.25 (br dd, 2H), 4.05 (br t, 2H), 2.50 (s, 3H), 2.25 (m, 1H), 1.48 (brd, 1H).

Example 8

A General Procedure for the Synthesis of Pyrazolo[1,5-a]pyrimidines represented by General Formula (V-02)

Synthesis of 3-(5,7-dichloropyrazolo[1,5-a]pyrimidin-6-yl)-propan-1-ol

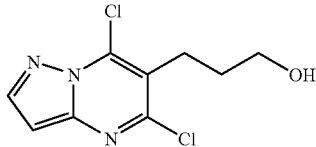

A mixed solution was prepared by adding dropwise a borane-dimethyl sulfide complex (20.3 mL, 40.7 mmol) to a tetrahydrofuran (85 mL) solution containing 6-allyl-5,7-dichloropyrazolo[1,5-a]pyrimidine (5.8 g, 25.4 nmol) at 0° C. over 30 min while strring. After flrther stirring at room temperature for 1 hr, the mixed solution was cooled to 0° C. The mixed solution was treated with 1 N aqueous solution of sodium hydroxide (40 mL, 40 mmol) and subsequently with aqueous hydrogen peroxide solution (30% aqueous solution, 3 nm), and the resulting solution was stirred at room temperature for 1 hr. After extracting the mixture solution with ethyl acetate, the organic layer was washed with saturated aqueous solution of sodium chloride, and then dried with sodium sulfate. After drying, sodium sulfate was filtered off and the solvent was removed under vacuum. The residue was purified by column chromatography (25-50% ethyl acetate/hexane) to obtain the title compound (3.4 g, yield: 55%).

$^1$H-NMR (400 MHz, CDCl$_3$) δ:8.17 (d,J=2.2Hz, 1H), 6.71 (d,J=2.2Hz, 1H), 3.80 (t, J=6.1 Hz, 2H), 3.10-3.07 (m, 2H), 1.99-1.97 (m, 2H).

Example 9

A General Procedure for the Synthesis of a Pyrazolo[1,5-a]pyrimidine Compound represented by General Formula (IV)

a) A mixture solution prepared by adding an amine R$^3$NH$_2$ (0.26 mol) to a 2-propanol solution (400 mL) containing 5,7-dichloropyrazolo[1,5-a]pyrimidine (appropriately substituted at 6-position) (V) (0.24 mol) and trimethylamine (0.49 mol) was stirred overnight at room temperature (when the reaction does not proceed at room temperature, the mixture was heated at 80° C. overnight). After concentrating the mixture solution under vacuum, the residue was partitioned between water and methylene chloride. The organic layer was washed with water, and the combined aqueous layer was again extracted with methylene chloride. After combining the organic layers, it was washed with saturated aqueous solution of sodium chloride and subsequently dried with sodium sulfate. After drying, sodium sulfate was filtered off and the solvent was removed under vacuum to obtain a precursor (IV). [Purification: usually, the products did not require any further purification, but if they did, they were recrystallized. Analysis:

$^1$H-NMR, HPLC and MS].

b) A reaction solution was prepared by adding an amine R$^3$NH$_2$ (1.2 equivalent) to a 2-propanol solution (25 mL) containing N,N-diisopropylethylamine (2 equivalent) and 5,7-dichoropyrazolo[1,5-a]pyrimidine (V) (2 g) and was heated at 80° C. overnight, and the solvent was removed under vacuum. After partitioning the residue between water and methylene chloride, the organic layer was washed with water and saturated aqueous solution of sodium chloride, and dried with magnesium sulfate. After drying, magnesium sulfate was filtered off and the solvent was removed under vacuum to obtain the product (IV).

c) A reaction solution was prepared by adding R$_3$H$_2$ (25 mmol) and subsequently adding a tetrahydrofaran (50 mL) solution containing 5,7-dichloropyrazolo[1,5-a]pyrimidine (V) appropriately substituted at 6-position (25 mmol) to a stirred N,N-dimethylformamide (30 mL) suspension containing sodium hydroxide (50 mmol), and was stirred at 50° C. for 2 hrs. The reaction was terminated by adding saturated aqueous solution of ammonium chloride. After performing extraction with ethyl acetate, the organic layers were combined and washed with saturated aqueous solution of sodium chloride and subsequently dried with magnesium sulfate. The solvent was removed under vacuum to obtain a crude product (IV). The typical yield of c) ranged from 60 to 80%.

d) A mixture solution was prepared by adding sodium hydroxide (3 mmol) to a toluene (3 mL) solution containing 2-chloroacetoanilide (2.2 mmol) at room temperature. After the preparation, the mixture solution was heated until the foaming was stopped and the solution was homogenized. To the mixture solution was added appropriately substituted 5,7-dichloropyrazolo[1,5-a]pyrimidine (V) (1 mmol), and the resultant solution was heated under reflux for 5 hrs. (Meanwhile, the solution became homogenized.) While cooling, acetic acid (1 mL) and water (1 mL) were carefully added to the solution, followed by stirring for 15 min. After removing the solvent under vacuum, the remaining acetic acid was removed by azeotrope with toluene (3 times). The residue was partitioned between water and ethyl acetate and the organic layer was washed with water and saturated aqueous solution of sodium chloride and then dried. The solvent was removed under vacuum and the residue was purified by column chromatography to obtain a desired compound (IV). The typical yield of d) ranged from 50 to 70%.

(IV)

| Compound No. | R¹ | R² | R⁴ | R³ | mp (° C.) or ¹H-NMR |
|---|---|---|---|---|---|
| IV-05 | H | H | Me | 2-chlorophenyl | ¹H-NMR(400 MHz, CDCl₃)δ: 7.45(d, 1H), 7.27(t, 1H), 7.15(t, 1H), 7.05(d, 1H), 6.50(s, 1H), 1.91(s, 3H). |
| IV-06 | H | Cl | H | 3-chloro-4-fluorophenyl | mp 184-186 |
| IV-07 | H | COOEt | Me | 4-ethoxyphenyl (CH₃CH₂O-) | ¹H-NMR(400 MHz, DMSO-d₆)δ: 9.95(s, 1H), 8.62(s, 1H), 7.15(d, J=8.8Hz, 2H), 6.92(d, J=8.8Hz, 2H), 4.27(q, J=7.1Hz, 2H), 4.02(q, J=6.8Hz, 2H), 1.78(s, 3H), 1.27-1.35(m, 6H). |
| IV-08 | H | CN | H | 3-chloro-4-fluorophenyl | ¹H-NMR(400 MHz, DMSO-d₆)δ: 8.80(s, 1H), 7.70(dd, J=6.7Hz, 2.6Hz, 1H), 7.55(t, J=9.0Hz, 1H), 7.53-7.46(m, 1H), 6.41(s, 1H). |
| IV-09 | H | H | Me | 4-(benzyloxy)phenyl | ¹H-NMR(400 MHz, CDCl₃)δ: 8.07(s, 1H), 8.00(d, J=2.2Hz, 1H), 7.46-7.35(m, 5H), 7.12(d, J=9.0Hz, 2H), 7.00(d, J=9.0Hz, 2H), 6.49(d, J=2.2Hz, 1H), 5.09(s, 2H), 1.90(s, 3H). |
| IV-10 | H | H | Me | 3-chloro-4-fluorophenyl | ¹H-NMR(400 MHz, CDCl₃)δ: 8.01(d, J=2.2Hz, 1H), 7.98(br s, 1H), 7.18(m, 2H), 7.01(m, 1H), 6.54(d, J=2.2Hz, 1H), 1.96(s, 3H) |

-continued
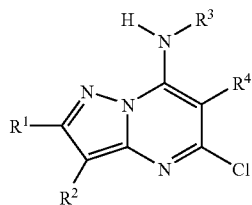
(IV)
| Compound No. | R¹ | R² | R⁴ | R³ | mp (° C.) or ¹H-NMR |
|---|---|---|---|---|---|
| IV-11 | H | CN | Me | 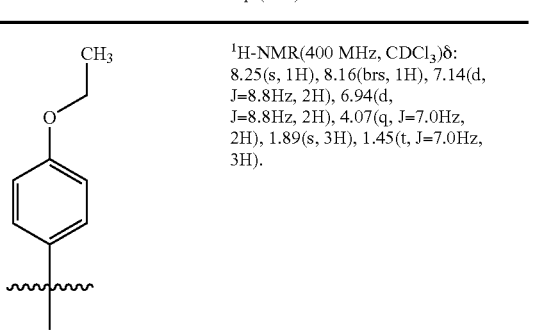 | ¹H-NMR(400 MHz, CDCl₃)δ: 8.25(s, 1H), 8.16(brs, 1H), 7.14(d, J=8.8Hz, 2H), 6.94(d, J=8.8Hz, 2H), 4.07(q, J=7.0Hz, 2H), 1.89(s, 3H), 1.45(t, J=7.0Hz, 3H). |
| IV-15 | H | H | Me | 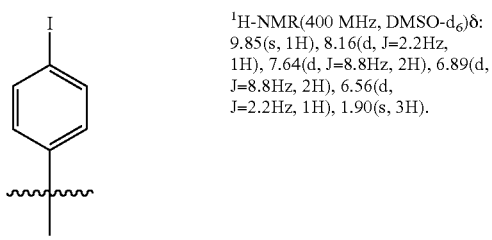 | ¹H-NMR(400 MHz, DMSO-d₆)δ: 9.85(s, 1H), 8.16(d, J=2.2Hz, 1H), 7.64(d, J=8.8Hz, 2H), 6.89(d, J=8.8Hz, 2H), 6.56(d, J=2.2Hz, 1H), 1.90(s, 3H). |
| IV-16 | H | H | Me | 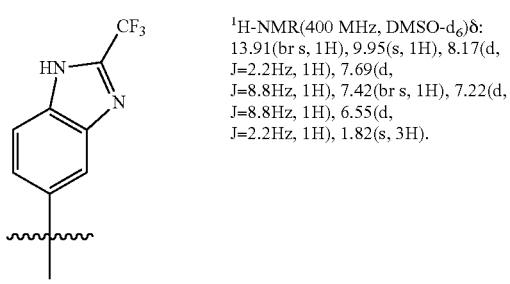 | ¹H-NMR(400 MHz, DMSO-d₆)δ: 13.91(br s, 1H), 9.95(s, 1H), 8.17(d, J=2.2Hz, 1H), 7.69(d, J=8.8Hz, 1H), 7.42(br s, 1H), 7.22(d, J=8.8Hz, 1H), 6.55(d, J=2.2Hz, 1H), 1.82(s, 3H). |
| IV-17 | H | H | Me | 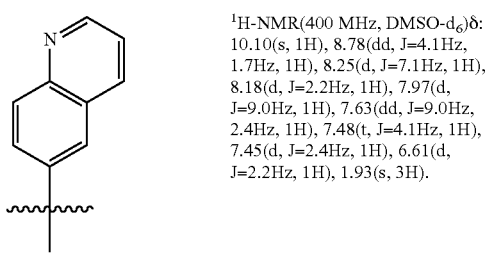 | ¹H-NMR(400 MHz, DMSO-d₆)δ: 10.10(s, 1H), 8.78(dd, J=4.1Hz, 1.7Hz, 1H), 8.25(d, J=7.1Hz, 1H), 8.18(d, J=2.2Hz, 1H), 7.97(d, J=9.0Hz, 1H), 7.63(dd, J=9.0Hz, 2.4Hz, 1H), 7.48(t, J=4.1Hz, 1H), 7.45(d, J=2.4Hz, 1H), 6.61(d, J=2.2Hz, 1H), 1.93(s, 3H). |

-continued
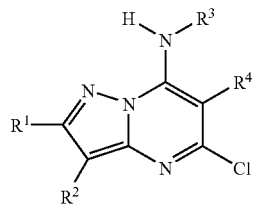
(IV)
| Compound No. | R¹ | R² | R⁴ | R³ | mp (° C.) or ¹H-NMR |
|---|---|---|---|---|---|
| IV-18 | H | H | Me | 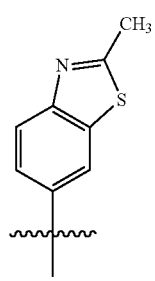 | ¹H-NMR(400 MHz, CDCl3)δ: 8.19(s, 1H), 8.02(d, J=2.4Hz, 1H), 7.95(d, J=8.8Hz, 1H), 7.57(d, J=2.4Hz, 1H), 7.25(dd, J=8.8Hz, 2.4Hz, 1H), 6.54(d, J=2.4Hz, 1H), 2.86(s, 3H), 1.93(s, 3H). |
| IV-19 | H | H | Me | 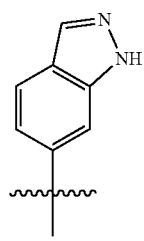 | ¹H-NMR(400 MHz, DMSO-d₆)δ: 12.90(s, 1H), 9.92(s, 1H), 8.17(d, J=2.2Hz, 1H), 8.01(s, 1H), 7.70(d, J=8.8Hz, 1H), 7.18(s, 1H), 6.96(dd, J=8.8Hz, 1.8Hz, 1H), 6.56(d, J=2.2Hz, 1H), 1.86(s, 3H). |
| IV-20 | H | H | Me | 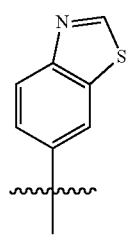 | ¹H-NMR(400 MHz, DMSO-d₆)δ: 10.01(s, 1H), 9.28(s, 1H), 8.17(d, J=2.2Hz, 1H), 8.03(d, J=8.8Hz, 1H), 7.82(d, J=2.2Hz, 1H), 7.36(dd, J=8.8Hz, 2.2Hz, 1H), 6.57(d, J=2.2Hz, 1H), 1.88(s, 3H). |
| IV-21 | H | H | Me | 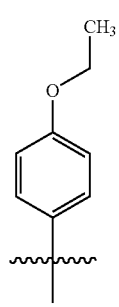 | ¹H-NMR(400 MHz, DMSO-d₆)δ: 8.08(s, 1H), 7.99(d, J=2.2Hz, 1H), 7.11(d, J=8.8Hz, 2H), 6.91(d, J=8.8Hz, 2H), 6.49(d, J=2.2Hz, 1H), 4.06(q, J=7.0Hz, 2H), 1.89(s, 3H), 1.44(t, J=7.0Hz, 3H). |

Example 10

A General Procedure for the Synthesis of a Pyrazolo[1,5-a]pyrimidine Compound represented by General Formula (IV-03)

Synthesis of (3-chloro-4-fluorophenyl){5-chloro-3-methylthio(pyrazolo[1,5-a]pyrimidin-7-yl)}amine

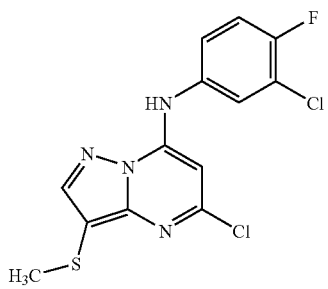

The reaction was carried out by carefully adding methylmagnesium chloride (0.25 mL, 3 M solution) to a dry tetrahydrofuiran (5 mL) solution containing {5-chloro-7-[(3-chloro-4-fluorophenyl)amino]-6-methylpyrazolo[1,5-a]pyrimidin-3-yl)} thiocarbonitrile (100 mg) over 2 hrs wile maintaining the temperature at 0 to 4° C. Acetic acid (2 equivalents) was added to the reaction solution and the solvent was removed under vacuum. After adding water and ethyl acetate to the resultant solution, the product was extracted with ethyl acetate (3 times). The combined organic layer was dried with sodium sulfate and subsequently the solvent was removed under vacuum to obtain the title compound (98 mg). The melting point ranged from 156 to 158° C.

Example 11

A General Procedure for the Synthesis of a Pyrazolo[1,5-a]pyrimidine Compound represented by General Formula (IV-02)

Synthesis of {6-[3-(tert-butyldimethylsilyloxy)propyl]-5-chloropyrazolo[1,5-a] pyrimidin-7-yl)}-(4-ethoxyphenyl)amine

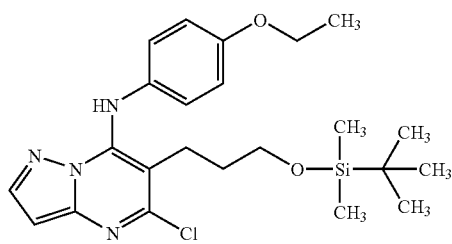

The reaction was carried out by adding triethylamine (861 µL, 6.18 mmol) and tert-butydimethylsilyl chloride (808 mg, 5.36 mmol) to a methylene chloride (14 mL) solution containing 3-[5-chloro-7-(4-ethoxyphenylamino)-pyrazolo[1,5-a]pyrimidin-6-yl]propan-1-ol (1.43 g, 4.12 mmol) at room temperature while stirring. After stirring for 16 hrs, 1 N hydrochloric acid was added to the mixture solution, and extraction was performed with ethyl acetate. The organic layer was washed with aqueous solution of sodium hydrogencarbonate and subsequently with aqueous solution of sodium chloride, followed by drying with sodium sulfate. After drying, sodium sulfate was filtered off and the solvent was removed under vacuum. The residue was purified by column chromatography (10-15% ethyl acetate/hexane) to obtain the title compound (2.03 g).

$^1$H-NMR (400 MHz, CDCl$_3$) δ:8.07 (s, 1H), 7.98 (d, J=2.4 Hz, 1H), 7.16 (d, J=8.8 Hz, 2H), 6.89 (d, J=8.8 Hz, 2H), 6.47 (d, J=2.4 Hz, 1H), 4.05 (q, J=7.1 Hz, 2H), 3.30 (t, J=6.4 Hz, 2H), 2.45 (t, J=6.4 Hz, 2H), 1.56-1.50 (m, 2H), 1.44 (t, J=7.1 Hz, 3H), 0.84 (s, 9H), −0.02 (s, 6H)

Example 12

A General Procedure for the Synthesis of a Pyrazolo[1,5-a]pyriridine Compound represented by General Formula (III)

Synthesis of {6-[3-(tert-butyldimethylsilyloxy)propyl]-5-chloropyrazolo [1,5-a]pyrimidin-7-yl}-(4-ethoxyphenyl)-carbamic acid tert-butyl ester

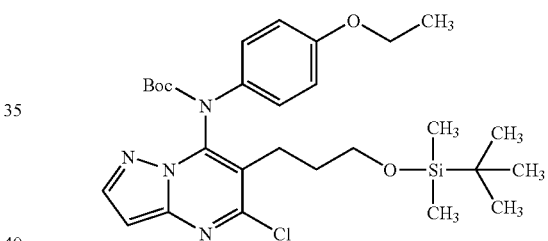

A reaction solution was prepared by adding triethylamrine (861 µL, 6.18 mmol), ditert-butyl dicarbonate (1.08 g, 4.94 mmol) and 4-dimethylaminopyridine (50.3 mg, 0.412 mmol) to a 1,4-dioxane (13 mL) solution containing {6-[3-(tert-butyldimethylsilyloxy)propyl]-5-chioropyrazolo[1,5-a]pyrmdin-7-yl}-(4-ethoxyphenyl)amine (2.00 g, 4.12 mmol) at room temperature while stirring. After stirring for 2 hrs, the reaction solution was poured to aqueous solution of ammonium chloride. The combined solution was extrated with ethyl acetate. The organic layer was washed with aqueous solution of sodium hydrogencarbonate and subsequently with aqueous solution of sodium chloride, and dried with sodium sulfate. After drying, sodium sulfate was filtered off and the solvent was removed under vacuum. The residue was purified by column chromatography (10% ethyl acetate/hexane) to obtain the title compound (2.03 g).

$^1$H-NMR (400 MHz, CDCl$_3$) δ:8.14 (d, J=2.2 Hz, 1H), 7.20 (d, J=8.8 Hz, 2H), 6.80 (d, J=8.8 Hz, 2H), 6.66 (d, J=2.2 Hz, 1H), 3.98 (q, J=7.1 Hz, 2H), 3.64-3.60 (m, 2H), 2.78-2.75 (m, 2H), 1.73-1.48 (m, 2H), 1.38 (t, J=7.1Hz, 3H), 1.25 (brs, 9H), 0.91 (s, 9H), −0.003 (s, 6H)

The following Bloc intermediates, III-01 to III-10, were prepared by the same method as above.

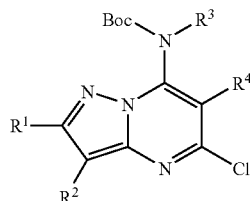

(III)

| Compound No. | R¹ | R² | R⁴ | R³ | mp (° C.) or ¹H-NMR |
|---|---|---|---|---|---|
| III-01 | H | H | Me | 2-chlorophenyl | ¹H-NMR(400 MHz, CDCl₃)δ: 8.12(s, 1H), 7.50(d, 1H), 7.24(t, 1H), 7.15(t, 1H), 7.05(d, 1H), 6.68(s, 1H), 2.55(s, 3H), 1.94(br s, 9H). |
| III-02 | H | Br | H | 3-chloro-4-fluorophenyl | mp 136-138 |
| III-03 | H | Cl | H | 3-chloro-4-fluorophenyl | mp 130-132 |
| III-04 | H | COOEt | Me | 4-ethoxyphenyl | ¹H-NMR(400 MHz, DMSO-d₆) δ: 8.68(brs, 1H), 7.22(d, J=8.8Hz, 2H), 6.87(d, J=8.8Hz, 2H), 4.30(q, J=7.1Hz, 2H), 3.98(q, J=7.1Hz, 2H), 2.22(s, 3H), 1.50-1.10(m, 15H). |
| III-05 | H | H | Me | 2-(methylthio)benzothiazol-6-yl | ¹H-NMR(400 MHz, DMSO-d₆) δ: 8.12(d, J=2.2Hz, 1H), 7.78(d, J=8.8Hz, 1H), 7.73(brs, 1H), 7.31(brs, 1H), 6.69(d, J=2.2Hz, 1H), 2.78(s, 3H), 2.31(brs, 3H), 1.35(brs, 9H). |
| III-06 | H | H | Me | 2-(ethylthio)benzothiazol-6-yl | ¹H-NMR(400 MHz, CDCl₃)δ: 8.12(d, J=2.2Hz, 1H), 7.78(d, J=8.8Hz, 1H), 7.71(brs, 1H), 7.31(brs, 1H), 6.69(d, J=2.2Hz, 1H), 3.34(q, J=7.6Hz, 1H), 2.31(brs, 3H), 1.47(t, J=7.6Hz, 3H), 1.35(brs, 9H). |

-continued

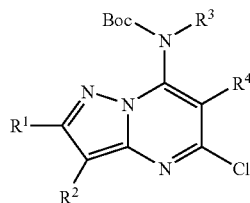

(III)

| Compound No. | R¹ | R² | R⁴ | R³ | mp (° C.) or ¹H-NMR |
|---|---|---|---|---|---|
| III-07 | H | H | Me | 2-(isopropylthio)benzothiazol-6-yl | ¹H-NMR(400 MHz, CDCl₃)δ: 8.12(d, J=2.2Hz, 1H), 7.79(d, J=8.8Hz, 1H), 7.82(brs, 1H), 7.31(brs, 1H), 6.69(d, J=2.2Hz, 1H), 4.14-3.98(m, 1H), 2.32(brs, 3H), 1.49(d, J=6.8Hz, 6H), 1.35(brs, 9H). |
| III-08 | H | Me | Me | 4-ethoxyphenyl | ¹H-NMR(400 MHz, CDCl₃)δ: 7.94(s, 1H), 7.17(d, J=9.0Hz, 2H), 6.80(d, J=9.0Hz, 2H), 3.98(q, J=7.1Hz, 2H), 2.35(brs, 3H), 2.29(brs, 3H), 1.38(t, J=7.1Hz, 3H), 1.25(brs, 9H). |
| III-09 | H | H | Me | 4-(methoxycarbonyl)phenyl | ¹H-NMR(400 MHz, CDCl₃)δ: 8.09(d, J=2.4Hz, 1H), 7.98(d, J=8.8Hz, 2H), 7.27(d, J=8.8Hz, 2H), 6.69(d, J=2.4Hz, 1H), 3.89(s, 3H), 2.24(s, 3H), 1.36(s, 9H). |
| III-11 | H | H | Et | 4-iodophenyl | ¹H-NMR(400 MHz, CDCl₃)δ: 8.13(d, J=2.2Hz, 1H), 7.62(d, J=8.8Hz, 2H), 6.99(d, J=8.8Hz, 2H), 6.69(d, J=2.2Hz, 1H), 2.68(m, 2H), 1.40(brs, 9H), 1.02(t, J=7.6Hz, 3H). |
| III-12 | H | H | Et | 4-(methoxycarbonyl)phenyl | ¹H-NMR(400 MHz, CDCl₃)δ: 8.15(d, J=2.4Hz, 1H), 8.00(d, J=8.8Hz, 2H), 7.30(d, J=8.8Hz, 2H), 6.71(d, J=2.4Hz, 1H), 3.89(s, 3H), 2.70(m, 1H), 2.62(m, 1H), 1.32(brs, 9H), 0.98(t, J=7.6Hz, 3H). |

-continued

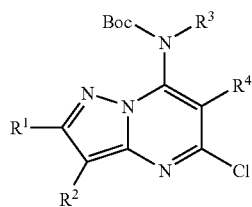
(III)

| Compound No. | R¹ | R² | R⁴ | R³ | mp (° C.) or ¹H-NMR |
|---|---|---|---|---|---|
| III-13 | H | H | –CH₂–CH=CH₂ (with gem-dimethyl, wavy bond) | 4-ethoxyphenyl | ¹H-NMR(400 MHz, DMSO-d$_6$) δ: 8.35(brs, 1H), 7.15(d, J=8.8Hz, 2H), 6.88(d, J=8.8Hz, 2H), 6.85(d, J=2.2Hz, 1H), 5.70-5.60(m, 1H), 5.00(d, J=9.8Hz, 1H), 4.87(d, J=16.8Hz, 1H), 3.98(q, J=7.0Hz, 2H), 3.44-3.41(m, 2H), 1.29(t, J=7.0Hz, 3H), 1.15(s, 9H). |
| III-14 | H | H | Me | 4-iodophenyl | ¹H-NMR(400 MHz, DMSO-d$_6$) δ: 8.25(d, J=2.0Hz, 1H), 7.68(d, J=8.8Hz, 2H), 7.08(d, J=8.8Hz, 2H), 6.82(d, J=2.0Hz, 1H), 2.19(s, 3H), 1.26(brs, 9H). |
| III-15 | H | H | Me | 4-benzyloxyphenyl | ¹H-NMR(400 MHz, DMSO-d$_6$) δ: 8.26(brs, 1H), 7.43-7.31(m, 5H), 7.24(d, J=8.8Hz, 2H), 6.97(d, J=8.8Hz, 2H), 6.80(d, J=2.4Hz, 1H), 5.06(s, 2H), 2.23(brs, 3H), 1.21(brs, 9H). |
| III-16 | H | H | H | 4-(COOCH₃)phenyl | ¹H-NMR(400 MHz, DMSO-d$_6$) δ: 8.33(d, J=2.2Hz, 1H), 7.94(d, J=8.8Hz, 1H), 7.45(d, J=8.8Hz, 1H), 7.42(s, 1H), 6.86(d, J=2.2Hz, 1H), 3.83(s, 3H), 1.29(s, 9H). |

-continued

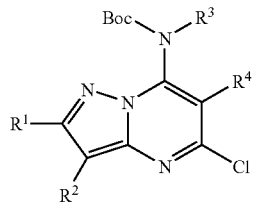
(III)

| Compound No. | R¹ | R² | R⁴ | R³ | mp (° C.) or ¹H-NMR |
|---|---|---|---|---|---|
| III-17 | H | H | (CH₂ group with branch bearing OH — 2-hydroxyethyl branch) | 4-ethoxyphenyl (OCH₂CH₃ on para position) | ¹H-NMR(400 MHz, DMSO-d₆) δ: 8.32(brs, 1H), 7.18(d, J=8.8Hz, 2H), 6.89(d, J=8.8Hz, 2H), 6.82(d, J=2.4Hz, 1H), 4.85(t, J=5.5Hz, 1H), 3.98(q, J=7.1Hz, 2H), 3.52-3.44(m, 1H), 3.29(brs, 1H), 2.78(brs, 2H), 1.30(q, J=7.1Hz, 3H), 1.17(s, 9H). |
| III-18 | H | H | -(CH₂)₃OH | 4-ethoxyphenyl | ¹H-NMR(400 MHz, DMSO-d₆) δ: 8.32(brs, 1H), 7.17(d, J=8.8Hz, 2H), 6.88(d, J=8.8Hz, 2H), 6.82(d, J=2.2Hz, 1H), 4.57(t, J=5.1Hz, 1H), 3.98(q, J=7.0Hz, 2H), 3.40(q, J=5.5Hz, 2H), 2.64-2.62(m, 2H), 1.29(t, J=7.0Hz, 3H), 1.17(brs, 9H). |
| III-19 | H | H | H | 4-ethoxyphenyl | ¹H-NMR(400 MHz, DMSO-d₆) δ: 8.16(d, J=2.2Hz, 1H), 7.26(d, J=9.0Hz, 2H), 6.86(d, J=9.0Hz, 2H), 6.67(d, J=2.2Hz, 1H), 6.62(s, 1H), 4.02(q, J=7.0Hz, 2H), 1.40(t, J=7.0Hz, 3H), 1.37(s, 9H). |
| III-20 | H | H | Me | 4-ethoxyphenyl | ¹H-NMR(400 MHz, DMSO-d₆) δ: 8.10(s, 1H), 7.22(d, J=8.8Hz, 2H), 6.82(d, J=8.8Hz, 2H), 6.65(d, J=2.2Hz, 1H), 3.99(q, J=7.0Hz, 2H), 2.31(s, 3H), 1.38(t, J=7.0Hz, 3H), 1.31(brs, 9H). |

Example 13

A General Procedure for the Synthesis of a Pyrazolo[1,5-a]pyrimidine Compound represented by General Formula (II)

Synthesis of (dl)-3-{7-[tert-butoxycarbonyl-(4-ethoxyphenyl)-amino]-6-methyl-pyrazolo[1,5-a]pyrimidin-5-yloxy}piperidine-1-carboxylic acid tert-butyl ester

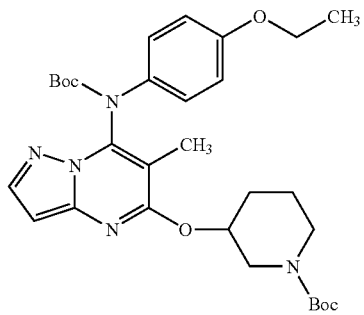

A reaction solution was prepared by adding sodium hydride (60% w/w in oil, 9.9 mg, 0.248 mmol) to a mixed solvent solution of tetrahydrofuran and N,N-dimethylformamide (3:1, 0.5 mL) containing (5-chloro-6-methylpyrazolo[1,5-a]pyrimidin-7-yl)-(4-ethoxyphenyl)-carbamic acid tert-butyl ester (20.0 mg, 0.0496 nmmol) and (dl)-3-hydroxypiperidine-1-carboxylic acid tert-butyl ester (49.9 mg, 0.248 mmol) at 0° C. while stirring, which was subsequently left standing until the temperature rises to room temperature. After feirter stirring for 2 hrs, the reaction was terminated by adding aqueous solution of sodium chloride to the reaction solution. The resultant mixed solution was extracted with ethyl acetate, and the organic layer was washed with aqueous solution of sodium chloride, followed by drying with sodium sulfate. After drying, sodium sulfate was filtered off and the solvent was removed under vacuum. The residue was purified by preparative thin layer chromatography (25% ethyl acetate/hexane) to obtain the title compound (19.5 mg).

Example 14

A General Procedure for the Synthesis of a Pyrazolo[1,5-a]pyrimidine Compound represented by General Formula (I)

Synthesis of (dl)-(4-ethoxyphenyl)-[6-methyl-5-(pyperdin-3-yloxy)pyrazolo [1,5-a]pyrimidin-7-yl]-amine (Compound No. 5)

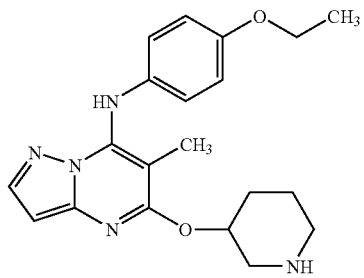

A reaction solution was prepared by adding trifluoroacetic acid (0.15 mL) to a methylene chloride (0.15 mL) solution containing (dl)-3-{7-[tert-butoxycarbonyl-(4-ethoxyphenyl)-amino]-6-methylpyrazolo[1,5-a]pyrimidin-5-yloxy}piperidine-1-carboxylic acid tert-butyl ester at 0° C. while stirring. After stirring for 2 hrs, the reaction solution was poured into saturated aqueous solution of sodium hydrogencarbonate, and extraction was performed with methylene chloride. The extract solutions were combined, which was dried with sodium sulfate. After drying, sodium sulfate was filtered off, and the solvent was removed under vacuum. The residue was purified by preparative thin layer chromatography (10% 2M $NH_3$—$CH_3OH/CH_2Cl_2$) to obtain the title compound (8.6 mg, the yield after two stages is 47%).

$^1$H-NMR (400 MHz, CDCl$_3$) δ:7.85 (d, J=2.2 Hz, 1H), 7.73 (brs, 1H), 7.06 (d, J=8.8 Hz, 2H), 6.87 (d, J=8.8 Hz, 2H),,6.24 (d, J=2.2 Hz, 1H), 5.25-5.22 (m, 1H), 4.03 (d, J=7.1 Hz, 2H), 3.22 (dd, J=13.0 Hz, 3.0 Hz, 1H), 3.07-3.04 (m, 1H), 2.90-2.88 (m, 2H), 2.04-2.02 (m, 1H), 1.95 (brs, 2H), 1.86-1.85 (m, 2H), 1.71 (s, 3H), 1.65-1.60 (m, 1H), 1.43 (t, J=7.1 Hz, 3H). HPLC retention time (Method A): 9.4 min. ESI/MS: 368.31 (M+H, $C_{20}H_{25}N_5O_2$),

Example 15

A General Procedure for the Synthesis of a Pyrazolo[1,5-]pyrimidine Compound represented by General Formula (I-03)

Synthesis of 3-[5-(trans-4-aminocyclohexyloxy)-7-(4-ethoxyphenylamino)-pyrazolo [1,5-a]pyrimidin-6-yl]propan-1-ol (Compound No. 88)

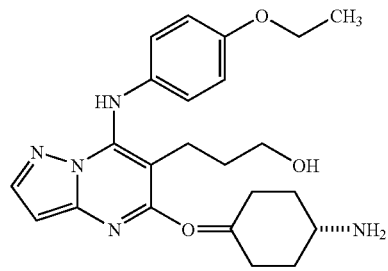

A reaction solution was prepared by first cooling a mixed solvent solution of N,N-dimethylformamide and tetrahydrofuiran (1:3, 0.4 mL) containing {6-[3-(tert-butyldimethylsilyloxy)propyl]-5-chloropyrazolo[1,5-]pyrimidin-7-yl}-(4-ethoxyphenyl)-carbamic acid tert-butyl ester (15.0 mg, 0.0267 mmol) and trans-4-aminocyclohexanol (30 mg, 0.264 mmol) at 0° C. and then adding sodium hydride (60% w/w in oil, 16 mg) to the mixed solvent solution while stirring. After stirring for 2 hrs, the reaction was terminated by adding aqueous solution of sodium hydrogencarbonate to the reaction solution. The resulting mixed solution was extracted with ethyl acetate, followed by drying with sodium sulfate. After drying, sodium sulfate was filtered off and the solvent was removed under vacuum. The residue was used for the subsequent reaction without further purification.

The above residue was dissolved in 1,4-dioxane (1 mL), and a solution (1 mL) of 4 N hydrochloric acid-1,4-dioxane was added at room temperature. After stirring for 16 hrs, the solvent was removed under vacuum. The residue was partitioned between saturated aqueous solution of sodium hydrogencarbonate and ethyl acetate, and the organic layer was dried with sodium sulfate. After drying, sodium sulfate was filtered off and the solvent was removed under vacuum. The residue was purified by preparative thin layer chromatography (10% 2 N-$NH_3$—$CH_3OH/CH_2Cl_2$) to obtain the title compound (12.8 mg), $^1$H-NMR (400 MHz, CDCl$_3$) δ: 7.86 (d, J=2.2 Hz, 1H), 7.72 (s, 1H), 7.13 (d, J=8.8 Hz, 2H), 6.87 (d, J=8.8 Hz, 2H), 6.26 (d, J=2.2 Hz, 1H), 5.16-5.14 (m, 1H), 4.03 (q, J=7.1 Hz, 2H), 3.26 (t, J=6.4 Hz, 2H), 2.80-2.78 (m, 1H), 2.32-2.28 (m, 2H), 2.21-2.18 (m, 2H), 1.95-1.92 (m, 2H), 1.72-1.70 (m, 2H), 1.57-1.52 (m, 2H), 1.42 (t, J=7.1 Hz, 3H). HPLC retention time (Method A): 8.90 min. ESI/MS: 426.2 (M+H, C$_{23}$H$_{31}$N$_5$O$_3$).

Example 16

A General Procedure for the Synthesis of a Pyrazolo[1,5-a]pyrimidine Compound represented by General Formula (I-02)

Synthesis of (dl)-(4-ethoxyphenyl)-[6-methyl-5-(trans-4-propylpiperidin-3-yloxy)pyrazolo[1,5-a]pyrimidin-7-yl]amine (Compound No. 16)

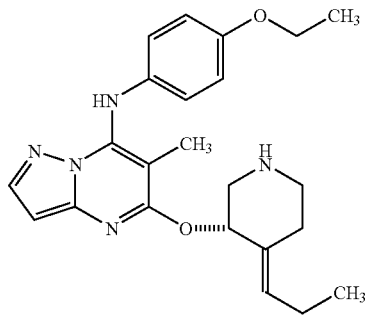

An ethanol solution containing (dl)-trans-4-allyl-3-[7-(4-ethoxyphenylamino)-6-methylpyrazolo[1,5-a]pyrimidin-5-ylo xy]piperidine-1-craboxylic acid benzyl ester was subjected to hydrogenation by using palladium supported on carbon under hydrogen atmosphere. After stirring for 4 hrs, the mixed solution was filtered, and the solvent was removed under vacuum. The residue was purified by preparative thin layer chromatography to obtain the title compound.

$^1$H-NMR (400 MHz, CDCl$_3$) δ: 7.85 (d, J=2.2 Hz, 1H), 7.71 (s, 1H), 7.07 (d, J=8.8 Hz, 2H), 6.87 (d, J=8.8 Hz, 2H), 6.23 (d, J=2.2 Hz, 1H), 4.90-4.85 (m, 1H), 4.04 (q, J=7.1 Hz, 2H), 3.49 (dd, J=12.0 Hz, 4.2 Hz, 1H), 3.05-3.01 (m, 1H), 2.63-2.58 (m, 1H), 2.53-2.48 (m, 1H), 1.92-1.88 (m, 1H), 1.76-1.72 (m, 1H), 1.70 (s, 3H), 1.68-1.59 (m, 1H), 1.43-1.39 (m, 3H), 1.24 (m, 4H), 0.89-0.85 (m, 3H). HPLC retention time (Method A): 11.80 min. ESI/MS: 410.3 M+H, C$_{23}$H$_{31}$N$_5$O$_2$).

Example 17

A General Procedure for the Synthesis of a Pyrazolo[1,5-a]pyrimidine Compound represented by General Formula (II-13)

Synthesis of (dl)-trans-3-{7-[tert-butoxycarbonyl-(4-ethoxyphenyl)-amino]-6-methyl-pyrazolo[1,5-a]pyrimidin-5-yloxy}-4-formylmethylpiperidine-1-carboxylic acid benzyl ester

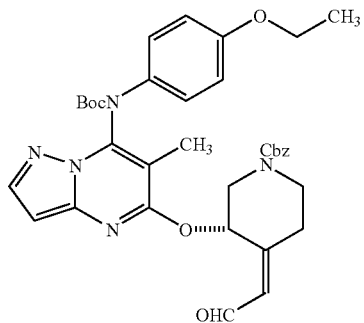

A reaction mixture solution was prepared by adding sodium periodate (23.8 mg, 0113 mmol) and osmium tetroxide (2.5wt % tert-butanol solution; 93 μL, 7.42×10$^{-3}$ mmol) to a mixed solution of tetrahydrofuran (0.4 mL)-water (0.1 mL) containing (dl)-trans-4-allyl-3-(7-[tert-butoxycarbonyl-(4-ethoxyphenyl)-amino]-6-methylpyrazolo [1,5-a]pyrimidin-5-yloxy]piperidine-1-carboxylic acid benzyl ester (23.8 mg, 0.0371 mmol) while stirring. After stirring overnight, the reaction was terminated by adding Na$_2$S$_2$O$_3$ to the reaction mixture solution. The resulting mixed solution was extracted with ethyl acetate and the organic layer was washed with saturated aqueous solution of sodium chloride, and dried with sodium sulfate. After drying, sodium sulfate was filtered off, and the solvent was removed under vacuum to obtain the title compound. The residue was used for the subsequent reaction without Pher purification.

Example 18

A General Procedure for the Synthesis of a Pyrazolo[1,5-a]pyrlmidine Compound represented by General Formula (II-14)

Synthesis of (dl)-trans-3-{7-[tert-butoxycarbonyl-(4-ethoxyphenyl)-amino]-6-methylpyrazolo[1,5-a]pyrimidin-5-yloxy}-4-formylmethylpiperidine-1-carboxylic acid benzyl ester

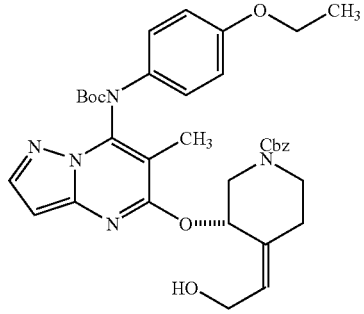

A reaction solution was prepared by dissolving the residue of the above (dl)-trans-3-{7-[tert-butoxycarbonyl-(4-ethoxyphenyl)-amino]-6-methylpyrazolo [1,5-a] pyrimidin-5-yloxy}-4-formylmethylpiperidine-1-carboxylic acid benzyl ester in methanol and then adding sodium borohydride (4.2 mg, 0.11 mmol). After stirring for 15 min, saturated aqueous solution of ammonium chloride was added to the reaction solution to terminate the reaction. The resulting mixed solution was extracted with ethyl acetate, and the organic layer was washed with saturated aqueous solution of sodium chloride, and dried with sodium sulfate. After drying, sodium sulfate was filtered off and the solvent was removed under vacuum, The crude product was purified by preparative thin layer chromatography (70% ethyl acetate-hexane) to obtain the title compound (7.6 mg).

Example 19

A General Procedure for the Synthesis of a Pyrazolo[1,5-a]pyrimidine Compound represented by General Formula (II-15)

Synthesis of (dl)-trans-3-{7-[tert-butoxycarbonyl-(4-etboxyphenyl)-amino]-6-methylpyrazolo[1,5-a]pyrimidin-5-yloxy}-4-carboxymethylpiperidine-1-carboxylic acid benzyl ester

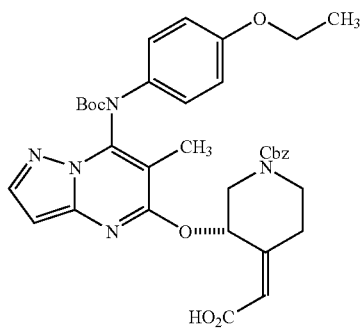

A reaction solution was prepared by adding 2-methyl-2-butene (222 µL, 0.42 mmol) and sodium chlorite (38.0 mg, 0.42 mmol) to a mixed solution of tert-butanol (4 mL) and water (0.4 mL) containing (dl)-trans-3-({7-[tert-butoxycarbonyl-(4-ethoxyphenyl)-amino]-6-methylpyrazolo[1,5-a]pyrimidin-5-yloxy}-4-formylmethylpiperidine-1-carboxylic acid benzyl ester (135 mg, 0.21 mnnol) and sodium phosphate (327 mg, 2.10 mmol) while stirring. After stirring for 3 hrs, aqueous solution of sodium thiosulfate was added to the reaction solution. The resulting mixture solution was extracted with ethyl acetate and the organic layer was dried with sodium sulfate. After drying, sodium sulfate was filtered off and the solvent was removed under vacuum. The residue was purified by preparative thin layer chromatography (5% CH₃OH/CH₂Cl₂) to obtain the title compound (122 mg).

Example 20

A General Procedure for the Synthesis of a Pyrazolo[1,5-a]pyrinine Compound represented by General Formula (II-16)

Synthesis of (dl)-trans-3-{7-[tert-butoxycarbonyl-(4-ethoxyphenyl)-amino]-6-methylpyrazolo[1,5-a]pyrimidin-5-yloxy}-4-carbamoylmethylpiperidine-1- carboxylic acid benzyl ester

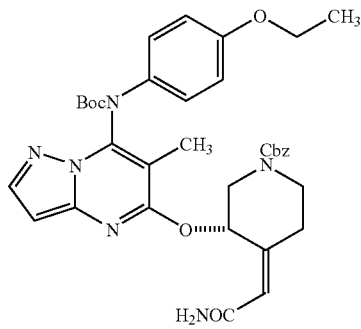

A reaction solution was prepared by adding O-(7-azabenzotriazol-1-yl) N,N,N',N'-tetramethyluronium hexafluorophosphate (0.0340 mmol) to an N,N-dimethylformamide (0.5 mL) solution containing (dl)-trans-3-{7-[tert-butoxycarbonyl-(4-ethoxyphenyl)-amino]-6-methylpyrazolo[1,5-a] pyrimidin-5-yloxy}-4-carboxymethylpiperidine-1-carboxylic acid benzyl ester (0.0227 mmol) and diisopropylethylamine (50 µL) while stiring and subsequently adding ammonia (0.045 mmol)-methanol solution. After stirring the reaction solution for 16 hrs, water was added to it. The resulting mixed solution was extracted with ethyl acetate and the organic layer was dried with sodium sulfate. After drying, sodium sulfate was filtered off and the solvent was removed under vacuum. The crude product was used without fit er purification.

Example 21

A General Procedure for the Synthesis of a Pyrazolo[1,5-a]pyrimidine Compound represented by General Formula (I-02)

Synthesis of (dl)-trans-2-{3-[7-(4-ethoxyphenyamino)-6-methylpyrazolo[1,5-a]pyrimidin-5-yloxyl-p]peridin-4-yl}acetamide (Compound No. 82)

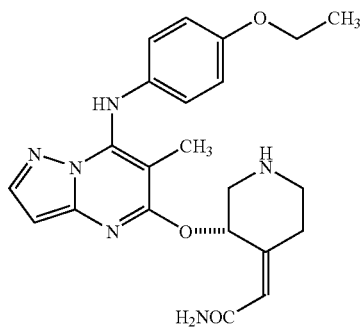

A mixed solution was prepared by dissolving the above residue (less than 0.0227 nmol) in acetonitrile (0.5 mL). After adding trimethylsilyl iodide (15 µL) to the mixed solution, the resultant solution was stirred at room temperature for 16 hrs. Subsequently water was added to the solution, extraction was performed with ethyl acetate and the organic layer was dried with sodium sulfate. After drying, sodium sulfate was filtered off and the solvent was removed under vacuum. The crude product was purified by preparative HPLC to obtain the title compound as a trifluoroacetate.

HPLC retention time (Method A): 8.33 min. ESI/MS: 425.1 (M+H, $C_{22}H_{28}N_6O_3$)

Example 22

A General Procedure for the Synthesis of a Pyrazolo[1,5-a]pyrimidine Compound represented by General Formula (II)

Synthesis of (4-ethoxyphenyl)-(5-methylthiopyrazolo[1,5-a]pyrimidin-7-yl)-carbamic acid tert-butyl ester

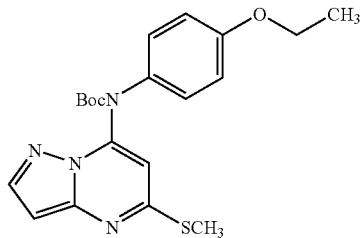

A mixed solution was prepared by adding (5-chloropyrazolo[1,5-a]pyrimidin-7-yl)-(4-ethoxyphenyl)-carbamic acid tert-butyl ester (50 mg, 0.126 mmol) and 2-propanol (4 mL) to a tetrahydrofuran (1 mL) solution containing sodium methylthiolate (11 mg, 0.145 mmol) while stirring. The solution was heated at 80° C. overnight on an oil bath. After pouring water to the solution, the resultant mixture was extracted with methylene chloride. The organic layers were combined and dried with magnesium sulfate. After drying, magnesium sulfate was filtered off and the solvent was removed under vacuum to obtain a crude product of the title compound.

Example 23

A General Procedure for the Synthesis of a Pyrazolo[1,5-a]pymidine Compound represented by General Formula (II-03)

Synthesis of (4-ethoxyphenyl)-(5-mercaptopyrazolo[1,5-a]pyrimidin-7-yl)-carbamic acid tert-butyl ester

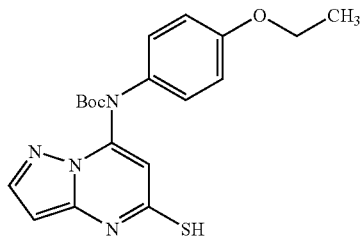

A reaction solution was prepared by adding potassium ethylxanthogenate (220 mg) to a 1,4-dioxane (10 mL) solution containing (5-chloropyrazolo[1,5-a]pyrimidin-7-yl)-(4-ethoxyphenyl)-carbamic acid tert-butyl ester (500 mg) and was subsequently heated at 90° C. for 18 hrs. After pouring the reaction solution to water, the resultant solution was extracted with ethyl acetate. The organic layers were combined and dried with magnesium sulfate. After drying, magnesium sulfate was filtered off and the solvent was removed under vacuum.

The above residue was dissolved in ethanol and the resultant solution was treated with 10% aqueous solution of sodium hydroxide. After the starting materials disappeared, the mixed solution was poured into water, followed by extraction with ethyl acetate. The organic layers were combined and dried with magnesium sulfate. After drying, magnesium sulfate was filtered off, and the solvent was removed under vacuum to obtain the title compound.

Example 24

A General Procedure for the Synthesis of a Pyrazolo[1,5-a]pyrimidine Compound represented by General Formula (II)

Synthesis of (dl)-3-{7-[tert-butoxycarbonyl-(4-ethoxyphenyl)-amino]pyrazolo[1,5-a]pyrimidin-5-ylthio}piperidine-1-carboxylic acid tert-butyl ester

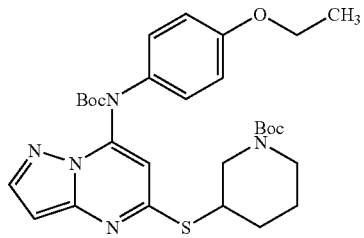

A mixture solution was prepared by adding sodium hydride (20 mg) to a mixed solution (1:4, 5 mL) of N,N-dimethylformamide and tetrahydrofuran containing (4-ethoxyphenyl)-(5-mercaptopyrazolo[1,5-a]pyrimidin-7-yl)-carbamic acid tert-butyl ester while stirring. After stirring for 30 min, (dl)-3-methanesulfonyloxypiperidine-1-carboxylic acid tert-butyl ester (100 mg) was added to the mixture solution, and the resultant solution was heated at 60° C. for 24 hrs. After pouring the resulting mixed solution to water, extraction was performed with with ethyl acetate. The organic layers were combined and dried with magnesium sulfate. After drying, magnesium sulfate was filtered off, and the solvent was removed under vacuum. The residue was dissolved in methylene chloride and trifluoroacetic acid was added in order to remove the Boc group. The crude product was purified by column chromatography ($NH_3$—$CH_3OH$—$CH_2Cl_2$) to obtain the title compound.

Example 25

A General Procedure for the Synthesis of Pyrazolo[1,5-a]pyrimidines represented by General Formula (I-05)

Synthesis of [5-(trans-4-aminocyclohexyloxy)-6-methylpyrazolo[1,5-a]pyrimidin-7-yl]-[4-(2-benzyloxyethoxy)phenyl]-amine (Compound No. 91)

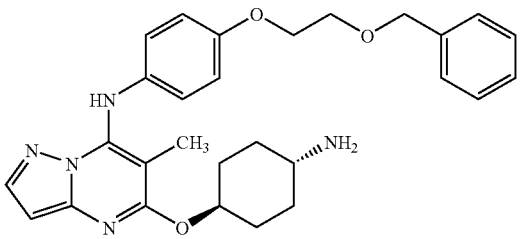

A mixed solution of ethanol (100 mL)-1,4-dioxane (100 mL) containing {5-[trans-4-aminocyclohexyloxy]-6-methylpyrazolo[1,5-a]pyrimidin-7-yl}-(4-benzyloxyphenyl)-carbamic acid tert-butyl ester (2.3 g) and palladium carbon (0.43 g, 10% on carbon) was stirred under hydrogen atmosphere for 23 hrs. After filtering off the catalyst, and the solvent was removed from the filtrate under vacuum to yield a crude intermediate (1.42 g). The crude intermediate residue was used for the subsequent reaction without furter purification, A methylene chloride (1.5 mL) suspension containing the above-mentioned crude intermediate (35.0 mg, 0.077 mmol), 2-(benzyloxy)ethanol (58.6 mg) and a polymer resin supported triphenylphosphine (3.0 mmol, 128 mg) was shaken at room temperature for 0.5 hrs. A reaction mixture was prepared by adding a methylene chloride (12.0 mL) solution containing diisopropyl azodicarboxylate (61 μL) to the suspension, and subsequently was shaken at room temperature for 22 hrs. After filtering the reaction mixture, the residual resin was washed with methylene chloride. The solvent was removed from the combined filtrate under vacuum to obtain a crude product of the Boc-protected intermediate. The crude product was used for the subsequent reaction without further purification.

After dissolving the above-mentioned residue in methylene chloride (2.0 mL), trifluoroacetic acid (0.40 mL) was added to the resultant solution. This mixture solution was stirred at room temperature for 3 hrs, and the solvent was removed under vacuum. The residue was purified by preparative HPLC to obtain the title compound as a trifluoroacetate. The HPLC retention time and ESI/MS of the compound are shown below.

HPLC retention time (Method A): 12.00 min. ESI/MS: 488.2 (M+H, $C_{28}H_{33}N_5O_3$).

Example 26

A General Procedure for the Synthesis of Pyrazolo[1,5-a]pyriridines represented by General Formula (I-06)

Synthesis of N-4'-[5-(trans-4-aminocyclohexyloxy)-6-methylpyrazolo[1,5-a]pyrimidin-7-yl] biphenyl-3,4'-diamine (Compound No. 93)

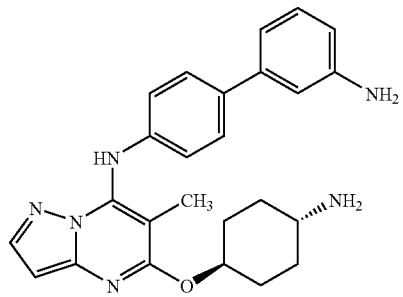

A reaction mixture was prepared by stirring a mixed solution of n-propanol (1.25 mL) and water (0.25 mL) containing a mixture of [5-(trans-4-aminocyclohexyloxy)-6-methylpyrazolo[1,5a]pyrimidin-7-yl]-(4-iodophenyl)-carbamic acid tert-butyl ester (35 mg, 0.0622 mmol), 3-aminophenylboronic acid (9.4 mg), sodium carbonate (78.0 mg, 0.746 mmol), palladium acetate (II) (4.2 mg) and triphenylphosphine (14.6 mg, 0.056 mmol) at 80° C. for 13 hrs. The solvent was removed from the reaction mixture under vacuum to yield a crude product of the Boc-protected intermediate. The crude product was used for the subsequent reaction without further purification.

A mixture solution was prepared by dissolving the above-mentioned crude product residue in methylene chloride (2.0 mL), and trifluoroacetiQ acid (0.6 mL) was added to the mixture solution. After stirring the resultant mixture solution at room temperature for 5 hrs, the solvent was removed under vacuum. The residue was purified by preparative HPLC to obtain the title compound as a trifluoroacetate. (23.6 mg). The HPLC retention time and EST/MS of the compound are shown below.

HPLC retention time (Method A): 6.93 min. ESI/MS: 429.2 (M+H, $C_{25}H_{28}N_6O$).

Example 27

A General Procedure for the Synthesis of a Pyrazolo[1,5-a]pyrrndine Compound represented by General Formula (II-09)

Synthesis of 4-[tert-butoxycarbonyl-(5-methoxy-6-methylpyrazolo[1,5-a]pyrimidin-7-yl)-amino]benzoic acid

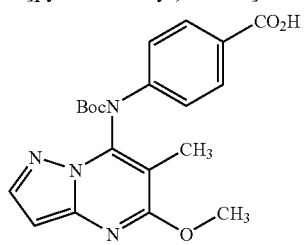

A mixture solution was prepared by adding a 1 N aqueous solution of sodium hydroxide (4.5 mL) to a methanol (18 mL) solution containing 4-{[5-(trans-4-aminocyclohexyloxy)-6-methylpyrazolo[1,5-a]pyrimidin-7-yl]-tert-butoxycarbonylamino}methylbenzoate ester (0.69 g, 1.17 mmol) while stirring. After further stirring for 30 min, the mixture solution was heated at 50° C. for 2 hrs. After adding 1 N hydrochloric acid to the resulting mixture solution, the combined solution was extracted with ethyl acetate. The organic layers were combined and dried with sodium sulfate. After drying, sodium sulfate was filtered off, and the solvent was removed under vacuum to obtain a crude product (0.66 g) of the title compound.

Example 28

A General Procedure for the Synthesis of a Pyrazolo[1,5-a]pyrimidine Compound represented by General Formula (I-7)

Synthesis of N-(2,2-dimethylprpopyl)-4-(5-methoxy-6-methylpyrazolo[1,5-a]pyrimidin-7-ylamino)-benzamide (Compound No. 99)

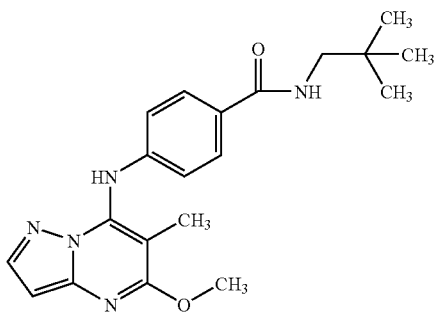

A reaction solution was prepared by adding neopentylamine (400 μL) to an N,N-dimethylformamide (1 mL) solution containing 4-[tert-butoxycarbonyl-(5-methoxy-6-methylpyrazolo[1,5-a]pyrimidin-7-yl)-amino]benzoic acid (66 mg, 0.17 mmol) and N,N-carbonyldiimidazole (190 mg) while stirring. After stirring at room temperature for 16 hrs, water was added to the reaction solution to terminate the reaction. The combined solution was partitioned between aqueous solution of ammonium chloride and methylene chloride. The organic layer was dried with sodium sulfate. After drying, sodium sulfate was filtered off, and the solvent was removed under vacuum to obtain a corresponding amide. The crude amide was used for the subsequent reaction without further purification.

After dissolving the above-mentioned residue in methylene chloride (2 mL), trifluoroacetic acid (1 mL) was added to the resulting solution. After stirring at room temperature for 2 hrs, the solvent was removed under vacuum from the resulting mixture solution. The residue was purified by preparative HPLC to obtain the title compound as a trifluoroacetate (4.8 mg).

$^1$H-NMR (400 MHz, CDCl$_3$) δ: 9.47 (s, 1H), 8.19-8.17 (m, 1H), 7.96 (d, J=2.2 Hz, 1H), 7.97 (d, J=8.8 Hz, 2H), 6.94 (d, J=8.8 Hz, 2H), 6.35 (d, J=2.2 Hz, 1H), 5.80-5.78 (m, 1H), 3.95-3.07 (d, J=6.4 Hz, 2H), 1.89 (s,3H), 0.88 (s, 9H).

HPLC retention time (Method A): 13.83 min. ESI/MS: 368.2 (M+H, C$_{20}$H$_{25}$N$_5$O$_2$).

Example 29

The compounds of listed in Table B below were synthesized in accordance with relevant methods described in Examples 1 to 28 by using the corresponding starting materials and reagents. The compound numbers assigned to each of the compounds in Table B correspond to the compound numbers of the compounds listed as specific examples in Table A above. The compounds were identified by mass spectrometry using single quadrupole instrumentation equipped with an electron spray source. For the results of mass spectrometry, observed values are shown as M+H, that is, a value in which a proton (H) is attached to the compound molecular mass (M). Also, values of the melting point (mp) are uncorrected; (d) denotes decomposition at or near the melting point. Several compounds of the present invention were selected to measure the $^1$H-NMR spectra (400 MHz, DMSO-d$_6$ or CDCl$_3$). The data for the chemical shift (δ: ppm) and coupling constant (J: Hz) are shown in Table B. The "HPLC retention time" refers to the retention time of the relevant compounds in HPLC analysis carried out under the conditions of the Method A, B, or C. The "synthetic method" in Table B is the Example number, which represents the same synthetic method as that in which the compound was synthesized.

TABLE B

| Compound No. | ESI/MS M + H | HPLC Retention time (min.) | HPLC Analytical condition | $^1$H-NMR(400 MHz)δ(ppm) | Synthetic method |
|---|---|---|---|---|---|
| 1 | 293.1 | 15.50 | A | | 14 |
| 3 | 399.0 | 17.20 | A | | 14 |
| 4 | 279.1 | 9.80 | A | | 14 |
| 6 | 382.7 | 9.20 | B | | 14 |
| 7 | 410.3 | 10.80 | A | | 16 |
| 8 | 410.3 | 11.30 | A | | 16 |
| 9 | 370.3 | 9.40 | A | | 14 |
| 10 | 404.2 | 10.50 | A | | 14 |
| 11 | 418.3 | 11.10 | A | | 14 |
| 12 | 416.3 | 10.70 | A | | 14 |
| 13 | 384.4 | 11.70 | A | | 14 |
| 14 | 368.3 | 9.50 | A | | 14 |
| 15 | 410.3 | 11.60 | A | (CDCl$_3$) 7.85(d, J=2.2Hz, 1H), 7.72(s, 1H), 7.08(d, J=9.0Hz, 2H), 6.88(d, J=9.0Hz, 2H), 6.23(d, J=2.2Hz, 1H), 5.25(br s, 1H), 4.04(q, J=7.1Hz, 2H), 3.45-3.42(m, 1H), 3.13-3.10(m, 1H), 2.79(dd, J=14.2, 1.5Hz, 1H), 2.70-2.63(m, 1H), 1.75(s, 3H), 1.57-1.53(m, 2H), 1.43(t, J=7.1Hz, 3H), 1.29(m, 5H), 0.85(t, J=7.0Hz, 3H). | 16 |
| 17 | 382.4 | 9.70 | A | | 14 |
| 18 | 382.3 | 9.60 | A | | 14 |
| 19 | 502.0 | 10.90 | A | | 14 |
| 20 | 410.2 | 12.60 | A | | 14 |
| 21 | 422.2 | 12.80 | A | | 14 |
| 22 | 424.2 | 13.40 | A | | 14 |
| 23 | 421.1 | 17.50 | A | | 14 |
| 24 | 436.1 | 16.40 | A | | 14 |
| 26 | 436.2 | 12.70 | A | | 14 |
| 27 | 412.2 | 11.20 | A | | 16 |
| 28 | 328.3 | 10.80 | A | | 14 |
| 29 | 342.3 | 12.10 | A | | 14 |

TABLE B-continued

| Compound No. | ESI/MS M + H | HPLC Retention time (min.) | HPLC Analytical condition | ¹H-NMR(400 MHz)δ(ppm) | Synthetic method |
|---|---|---|---|---|---|
| 30 | 356.2 | 12.20 | A | | 14 |
| 31 | 404.2 | 13.40 | A | | 14 |
| 32 | 416.2 | 14.20 | A | | 14 |
| 33 | 342.2 | 10.80 | A | | 14 |
| 34 | 356.2 | 10.70 | A | | 14 |
| 35 | 356.2 | 12.50 | A | | 14 |
| 36 | 356.2 | 14.40 | A | | 14 |
| 37 | 416.2 | 14.20 | A | | 14 |
| 38 | 370.3 | 12.20 | A | | 14 |
| 39 | 384.3 | 13.30 | A | | 14 |
| 40 | 382.3 | 12.40 | A | | 14 |
| 41 | 412.2 | 10.60 | A | | 16 |
| 42 | 357.3 | 7.40 | A | | 14 |
| 43 | 388.2 | 10.10 | A | | 14 |
| 44 | 438.3 | 15.80 | A | | 14 |
| 45 | 427.0 | 13.33 | A | | 14 |
| 46 | 441.0 | 13.10 | A | | 14 |
| 47 | 382.1 | 11.05 | A | | 14 |
| 48 | 417.1 | 9.24 | A | | 14 |
| 49 | 466.1 | 7.63 | A | | 14 |
| 50 | 384.1 | 12.84 | A | | 14 |
| 51 | 428.2 | 13.28 | A | | 14 |
| 52 | 414.1 | 15.66 | A | | 14 |
| 53 | 417.1 | 11.78 | A | | 14 |
| 54 | 424.1 | 14.80 | A | (DMSO-$d_6$) Trifluoroacetate 9.70(s, 1H), 8.83(m, 1H), 8.41(m, 1H), 7.99(d, J=2.2Hz, 1H), 7.58(d, J=8.8Hz, 2H), 6.98(d, J=8.8Hz, 2H), 6.36(d, J=2.2Hz, 1H), 5.43-5.41(m, 1H), 3.40-3.38(m, 2H), 3.15-3.13(m, 1H), 3.08-3.05(m, 1H), 2.00-1.97(m, 3H), 1.89(s, 3H), 1.75-1.72(m, 1H). | 14 |
| 55 | 388.1 | 12.92 | A | (DMSO-$d_6$) Trifluoroacetate 9.19(s, 1H), 8.79-8.77(br m, 1H), 8.36-8.34(br m, 1H), 7.98(d, J=2.2Hz, 1H), 6.31(d, J=2.2Hz, 1H), 6.18-6.15(m, 3H), 5.40-5.38(m, 1H), 3.70(s, 3H), 3.40-3.37(m, 2H), 3.12-1.10(m, 1H), 3.08-3.05(m, 1H), 1.96-1.92(m, 3H), 1.84(s, 3H), 1.74-1.72(m, 1H). | 14 |
| 56 | 441.2 | 10.82 | C | (DMSO-$d_6$) Trifluoroacetate 9.29(s, 1H), 8.75(m, 1H), 8.35(m, 1H), 8.11(d, J=7.6Hz, 1H), 8.00(d, J=2.2Hz, 1H), 7.91(s, 1H), 7.61-7.59(m, 2H), 7.45(t, J=7.3Hz, 1H), 7.30-7.29(m, 1H), 7.16(t, J=7.3Hz, 1H), 6.29(d, J=2.2Hz, 1H), 5.39-5.38(m, 1H), 4.54(q, J=7.3Hz, 2H), 3.44-3.40(m, 2H), 2.95-3.92(m, 2H), 1.95-1.93(m, 3H), 1.66-1.65(m, 1H), 1.64(s, 3H), 1.32(t, J=7.3Hz, 3H). | 14 |
| 57 | 442.1 | 10.13 | C | (DMSO-$d_6$) Trifluoroacetate 9.63(s, 1H), 8.82(m, 1H), 8.37(m, 1H), 7.99(d, J=2.2Hz, 1H), 7.45(d, J=9.0Hz, 1H), 7.13(d, J=2.7Hz, 1H), 6.93(dd, J=9.0Hz, 2.7Hz, 1H), 6.35(d, J=2.2Hz, 1H), 5.42-5.40(m, 1H), 3.89-3.35(m, 2H), 3.16-3.14(m, 1H), 3.06-3.03(m, 1H), 1.96-1.93(m, 3H), 1.73(s, 3H), 1.75-1.72(m, 1H). | 14 |
| 58 | 398.2 | 8.73 | A | | 16 |
| 59 | 445.1 | 12.41 | A | (DMSO-$d_6$) Trifluoroacetate 9.01(s, 1H), 8.78-8.76(m, 1H), 8.39-8.37(m, 1H), 7.97(d, J=2.2Hz, 1H), 7.00(d, J=9.0Hz, 2H), 6.96(d, J=9.0Hz, 2H), | 14 |

TABLE B-continued

| Compound No. | ESI/MS M + H | HPLC Retention time (min.) | HPLC Analytical condition | ¹H-NMR(400 MHz)δ(ppm) | Synthetic method |
|---|---|---|---|---|---|
| | | | | 6.90(d, J=9.0Hz, 2H), 6.85(d, J=9.0Hz, 2H), 6.25(d, J=2.2Hz, 1H), 5.38-5.36(m, 1H), 3.70(s, 3H), 3.35-3.32(m, 2H), 3.13-3.08(m, 2H), 1.92(m, 3H), 1.72-1.71(m, 1H), 1.71(s, 3H). | |
| 60 | 471.1 | 14.31 | A | (DMSO-$d_6$) Trifluoroacetate 9.77(s, 1H), 8.90(m, 1H), 8.51(m, 1H), 8.05(d, J=2.2Hz, 1H), 8.02(d, J=8.6Hz, 2H), 7.93(s, 1H), 7.91(d, J=8.3Hz, 1H), 7.37(d, J=8.3Hz, 1H), 7.10(d, J=8.6Hz, 2H), 6.42(d, J=2.2Hz, 1H), 5.49-5.47(m, 1H), 3.48-3.44(m, 2H), 3.19-3.13(m, 2H), 2.49(s, 3H), 2.02-2.00(m, 3H), 1.97(s, 3H), 1.80-1.79(m, 1H). | 14 |
| 61 | 473.1 | 9.11 | A | (DMSO-$d_6$) Trifluoroacetate 9.88(s, 1H), 8.86-8.84(m, 1H), 8.46-8.43(m, 1H), 8.00(d, J=2.2Hz, 1H), 7.60(d, J=8.8Hz, 2H), 7.03(d, J=8.8Hz, 2H), 6.38(d, J=2.2Hz, 1H), 5.45-5.40(m, 1H), 3.63-3.61(m, 4H), 3.42-3.40(m, 2H), 3.15-3.08(m, 2H), 2.84-2.81(m, 4H), 1.96-1.93(m, 3H), 1.92(s, 3H), 1.75-1.72(m, 1H). | 14 |
| 62 | 366.1 | 9.31 | A | | 14 |
| 63 | 375.1 | 6.58 | A | | 14 |
| 64 | 402.2 | 13.70 | A | 8.44(s, 1H), 7.91(d, J=2.2Hz, 1H), 7.80(br m, 3H), 7.12(dd, J=8.8, 2.4Hz, 1H), 7.05(d, J=8.7Hz, 1H), 6.90(d, J=2.4Hz, 1H), 6.27(d, J=2.2Hz, 1H), 5.03-5.01(m, 1H), 3.74(s, 3H), 3.12-3.09(m, 1H), 2.16-2.13(m, 2H), 2.00-1.96(m, 2H), 1.71(s, 3H), 1.55-1.47(m, 4H). | 14 |
| 65 | 455.3 | 16.34 | A | | 14 |
| 66 | 459.2 | 14.33 | A | (DMSO-$d_6$) Trifluoroacetate 8.48(s, 1H), 7.91(d, J=2.2Hz, 1H), 7.78-7.76(m, 3H), 6.97(d, J=8.8Hz, 2H), 6.91(d, J=8.8Hz, 2H), 6.85(d, J=8.8Hz, 2H), 6.81(d, J=8.8Hz, 2H), 6.20(d, J=2.2Hz, 1H), 4.98-4.94(m, 1H), 3.66(s, 3H), 3.08-3.01(m, 1H), 2.10-2.07(m, 2H), 2.96-1.92(m, 2H), 1.58(s, 3H), 1.57-1.44(m, 4H). | 14 |
| 67 | 396.1 | 11.13 | A | | 14 |
| 68 | 399.1 | 10.26 | A | | 14 |
| 69 | 398.1 | 11.37 | A | | 14 |
| 70 | 442.1 | 13.16 | A | | 14 |
| 71 | 428.2 | 15.74 | A | | 14 |
| 72 | 431.0 | 12.14 | A | | 14 |
| 73 | 438.0 | 14.03 | A | | 14 |
| 74 | 455.0 | 14.81 | A | | 14 |
| 75 | 469.0 | 15.32 | A | | 14 |
| 76 | 444.1 | 13.08 | A | | 14 |
| 77 | 464.0 | 11.72 | A | | 14 |
| 78 | 354.2 | 7.22 | A | | 14 |
| 79 | 309.0 | 15.60 | A | (DMSO-$d_6$) Trifluoroacetate 9.95(s, 1H), 8.11(d, J=2.2Hz, 1H), 7.63(d, J=6.7Hz, 2.0Hz, 1H), 7.50-7.47(m, 2H), 6.41(d, J=2.2Hz, 1H), 6.06(s, 1H), 3.31(s, 3H). | 14 |
| 80 | 384.1 | 11.30 | A | | 14 |
| 81 | 344.1 | 10.20 | A | | 14 |
| 83 | 439.2 | 8.66 | A | | 21 |

TABLE B-continued

| Compound No. | ESI/MS M + H | HPLC Retention time (min.) | HPLC Analytical condition | ¹H-NMR(400 MHz)δ(ppm) | Synthetic method |
|---|---|---|---|---|---|
| 84 | 453.2 | 9.42 | A | | 21 |
| 85 | 515.2 | 10.86 | A | | 21 |
| 86 | 465.2 | 9.36 | A | | 21 |
| 87 | 649.3 | 16.33 | A | | 14 |
| 89 | 412.2 | 9.17 | A | | 25 |
| 90 | 467.2 | 5.76 | A | | 25 |
| 92 | 462.2 | 10.22 | A | (DMSO-d₆) Trifluoroacetate 9.49(s, 1H), 7.94(d, J=2.2Hz, 1H), 7.89(d, J=4.0Hz, 1H), 7.83(br m, 3H), 7.66(d, J=8.8Hz, 2H), 7.51(d, J=4.0Hz, 1H), 6.96(d, J=8.8Hz, 2H), 6.31(d, J=2.2Hz, 1H), 5.03-5.00(m, 1H), 3.11-3.09(m, 1H), 2.49(s, 3H), 2.17-2.14(m, 2H), 2.00-1.97(m, 2H), 1.75(s, 3H), 1.54-1.46(m, 4H). | 26 |
| 94 | 382.2 | 10.72 | A | | 28 |
| 95 | 312.2 | 9.37 | A | (DMSO-d₆) Trifluoroacetate 9.47(s, 1H), 8.28-8.26(br m, 1H), 7.95(d, J=2.2Hz, 1H), 7.73(d, J=8.7Hz, 2H), 6.93(d, J=8.7Hz, 2H), 6.35(d, J=2.2Hz, 1H), 3.95(s, 3H), 1.78(s, 3H). | 28 |
| 96 | 380.1 | 12.39 | A | (DMSO-d₆) Trifluoroacetate 9.47(s, 1H), 8.27-8.26(br m, 1H), 7.95(d, J=2.2Hz, 1H), 7.74(d, J=8.8Hz, 2H), 6.94(d, J=8.8Hz, 2H), 6.35(d, J=2.2Hz, 1H), 3.95(s, 3H), 2.75(d, J=4.4Hz, 2H), 1.78(s, 3H). | 28 |
| 97 | 372.2 | 11.63 | A | | 28 |
| 98 | 366.2 | 13.10 | A | | 28 |
| 100 | 389.2 | 7.46 | A | (DMSO-d₆) Trifluoroacetate 9.53(s, 1H), 9.04(t, J=5.7Hz, 1H), 8.76(s, 1H), 8.69(d, J=5.7Hz, 1H), 8.22(d, J=8.0Hz, 1H), 7.96(d, J=2.2Hz, 1H), 7.80(d, J=8.6Hz, 2H), 7.79-7.77(m, 1H), 6.96(d, J=8.6Hz, 2H), 6.36(d, J=2.2Hz, 1H), 4.76(d, J=5.6Hz, 2H), 3.96(s, 3H), 1.80(s, 3H). | 28 |
| 101 | 389.2 | 7.43 | A | (DMSO-d₆) Trifluoroacetate 9.56(s, 1H), 9.17(t, J=5.7Hz, 1H), 8.78(d, J=6.4Hz, 2H,) 7.96(d, J=2.2Hz, 1H), 7.85(d, J=6.4Hz, 2H), 7.84(d, J=8.8Hz, 2H), 6.98(d, J=8.8Hz, 2H), 6.36(d, J=2.2Hz, 1H), 4.67(d, J=5.6Hz, 2H), 3.96(s, 3H), 1.82(s, 3H). | 28 |
| 102 | 478.2 | 10.70 | A | | 14 |
| 103 | 410.3 | 9.15 | A | | 14 |
| 104 | 468.4 | 11.47 | A | | 14 |
| 239 | 368.2 | 8.52 | A | (DMSO-d₆) Trifluoroacetate 9.06(s, 1H), 8.64-8.54(br m, 2H), 7.95(d, J=2.2Hz, 1H), 7.03(d, J=8.8Hz, 2H), 6.88(d, J=8.8Hz, 2H), 6.25(d, J=2.2Hz, 1H), 5.37-5.32(m, 1H), 3.99(q, J=7.0Hz, 2H), 3.20-3.18(br m, 4H), 2.14-2.11(m, 2H), 1.95-1.87(m, 2H), 1.65(s, 3H), 1.31(t, J=7.0Hz, 3H). | 14 |
| 240 | 430.2 | 9.84 | A | (DMSO-d₆) Trifluoroacetate 9.08(s, 1H), 8.63-8.54(br m, 2H), 7.95(d, J=2.2Hz, 1H), 7.45(d, J=7.3Hz, 2H), 7.39(t, J=7.3Hz, 2H), 7.32(t, J=7.3Hz, 1H), 7.04(d, J=9.0Hz, 2H), 6.98(d, J=9.0Hz, 2H), 6.25(d, J=2.2Hz, 1H), 5.36-5.33(m, 1H), 5.07(s, 2H), 3.21-3.19(br | 14 |

TABLE B-continued

| Compound No. | ESI/MS M + H | HPLC Retention time (min.) | HPLC Analytical condition | ¹H-NMR(400 MHz)δ(ppm) | Synthetic method |
|---|---|---|---|---|---|
| | | | | m, 4H), 2.14-2.11(m, 2H), 1.93-1.90(m, 2H), 1.66(s, 3H). | |
| 241 | 376.2 | 8.98 | A | | 14 |
| 242 | 337.2 | 13.94 | A | (CDCl₃) Trifluoroacetate 7.87(d, J=2.2Hz, 1H), 7.74(s, 1H), 7.06(d, J=8.8Hz, 2H), 6.87(d, J=8.8Hz, 2H), 6.31(d, J=2.2Hz, 1H), 5.00(q, J=2.4Hz, 2H), 4.04(q, J=7.0Hz, 2H), 1.88(t, J=2.4Hz, 3H), 1.73(s, 3H), 1.43(t, J=7.0Hz, 3H). | 14 |
| 243 | 339.2 | 14.77 | A | (CDCl₃) Trifluoroacetate 7.86(d, J=2.2Hz, 1H), 7.71(s, 1H), 7.06(d, J=8.8Hz, 2H), 6.87(d, J=8.8Hz, 2H), 6.28(d, J=2.2Hz, 1H), 5.90(m, 1H), 5.16(dd, J=17.2Hz, 1.8Hz, 1H), 5.08(dd, J=10.2, 1.8Hz, 1H), 4.42(t, J=6.7Hz, 2H), 4.04(q, J=7.0Hz, 2H), 2.55(q, J=6.7Hz, 2H), 1.69(s, 3H), 1.43(t, J=7.0Hz, 3H). | 14 |
| 244 | 382.2 | 8.82 | A | | 14 |
| 245 | 382.2 | 8.90 | A | | 14 |
| 246 | 357.1 | 12.61 | A | (CDCl₃) Trifluoroacetate 7.87(d, J=2.2Hz, 1H), 7.80(s, 1H), 7.09(d, J=8.8Hz, 2H), 6.88(d, J=8.8Hz, 2H), 6.25(d, J=2.2Hz, 1H), 4.97(s, 2H), 4.04(q, J=7.0Hz, 2H), 3.78(s, 3H), 1.76(s, 3H), 1.43(t, J=7.0Hz, 3H). | 14 |
| 247 | 343.2 | 12.66 | A | (CDCl₃) Trifluoroacetate 7.86(d, J=2.2Hz, 1H), 7.72(s, 1H), 7.05(d, J=8.8Hz, 2H), 6.86(d, J=8.8Hz, 2H), 6.28(d, J=2.2Hz, 1H), 4.54(t, J=4.6Hz, 2H), 4.03(q, J=7.0Hz, 2H), 3.78(t, J=4.6Hz, 2H), 3.44(s, 3H), 1.73(s, 3H), 1.43(t, J=7.0Hz, 3H). | 14 |
| 248 | 396.2 | 10.93 | A | (CDCl₃) Trifluoroacetate 7.87(d, J=2.2Hz, 1H), 7.75(s, 1H), 7.07(d, J=8.8Hz, 2H), 6.88(d, J=8.8Hz, 2H), 6.27(d, J=2.2Hz, 1H), 4.52(t, J=5.4Hz, 2H), 4.04(q, J=7.0Hz, 2H), 3.71(t, J=5.4Hz, 2H), 3.52(t, J=7.0Hz, 2H), 2.37(t, J=8.2Hz, 2H), 2.05-1.97(m, 2H), 1.68(s, 3H), 1.43(t, J=7.0Hz, 3H). | 14 |
| 249 | 376.2 | 9.71 | A | | 14 |
| 250 | 367.2 | 16.36 | A | | 14 |
| 251 | 369.2 | 13.33 | A | (DMSO-d₆) Trifluoroacetate 8.99(s, 1H), 7.93(d, J=2.2Hz, 1H), 7.01(d, J=8.8Hz, 2H), 6.87(d, J=8.8Hz, 2H), 6.25(d, J=2.2Hz, 1H), 5.32-5.25(m, 1H), 3.99(q, J=7.0Hz, 2H), 3.85-3.80(m, 2H), 3.56-3.50(m, 2H), 2.02-1.98(m, 2H), 1.67-1.63(m, 2H), 1.64(s, 3H), 1.31(t, J=7.0Hz, 3H). | 14 |
| 252 | 369.2 | 12.98 | A | | 14 |
| 253 | 382.2 | 8.74 | A | (DMSO-d₆) Trifluoroacetate 9.71(br s, 1H), 9.08(s, 0.5H), 9.08(s, 0.5Hz), 7.96(d, J=2.4Hz, 0.5H), 7.95(d, J=2.4Hz, 0.5H), 7.03(d, J=8.8Hz, 1H), 7.02(d, J=8.8Hz, 1H), 6.89(d, J=8.8Hz, 1H), 6.88(d, J=8.8Hz, 1H), 6.26(d, J=2.4Hz, 0.5H), 6.25(d, J=2.4Hz, 0.5H), 5.38(t, J=2.9Hz, 0.5H), 5.28-5.21(m, 0.5H), 3.99(q, J=6.9Hz, 3H), | 14 |

TABLE B-continued

| Compound No. | ESI/MS M + H | HPLC Retention time (min.) | HPLC Analytical condition | ¹H-NMR(400 MHz)δ(ppm) | Synthetic method |
|---|---|---|---|---|---|
| | | | | 3.52-3.49(m, 1H), 3.39-3.36(m, 1H), 3.22-3.07(m, 2H), 2.83(d, J=4.5Hz, 1.5H), 2.80(d, J=4.5Hz, 1.5H), 2.33-2.29(m, 1H), 2.18-2.14(m, 1H), 2.05-2.02(m, 1H), 1.81-1.76(m, 1H), 1.71(s, 1.5H), 1.60(s, 1.5H), 1.31(t, J=7.0Hz, 3H). | |
| 254 | 376.2 | 9.27 | A | | 14 |
| 255 | 383.2 | 12.19 | A | | 14 |
| 256 | 368.2 | 8.51 | A | (DMSO-d₆) Trifluoroacetate 10.38(br s, 1H), 9.11(s, 1H), 7.97(d, J=2.2Hz, 1H), 7.02(d, J=8.8Hz, 2H), 6.88(d, J=8.8Hz, 2H), 6.29(d, J=2.2Hz, 1H), 5.63-5.57(m, 1H), 3.9(q, J=7.0Hz, 2H), 3.80-3.74(m, 2H), 3.48-3.10(m, 3H), 2.66-2.59(m, 1H), 2.32-2.30(m, 1H), 2.14-2.12(m, 1H), 1.63(s, 3H), 1.31(t, J=7.0Hz, 3H). | 14 |
| 257 | 382.2 | 8.64 | A | | 14 |
| 258 | 382.2 | 8.67 | A | | 14 |
| 259 | 341.2 | 10.02 | A | | 14 |
| 260 | 368.3 | 8.51 | A | | 14 |
| 261 | 368.3 | 8.54 | A | | 14 |
| 262 | 397.3 | 7.21 | A | | 14 |
| 263 | 342.2 | 8.15 | A | | 14 |
| 264 | 354.2 | 8.33 | A | | 14 |
| 265 | 367.3 | 16.24 | A | | 14 |
| 266 | 382.2 | 10.14 | A | | 14 |
| 267 | 382.2 | 10.14 | A | | 14 |
| 268 | 352.2 | 8.64 | A | (DMSO-d₆) Trifluoroacetate 7.91(d, J=2.2Hz, 1H), 7.86-7.83(br s, 2H), 7.51(t, J=7.1Hz, 1H), 7.31-7.25(m, 4H), 7.22-7.19(m, 1H), 6.15(d, J=2.2Hz, 1H), 4.97-4.94(br m, 1H), 4.94(br s, 2H), 3.09-3.07(br m, 1H), 2.10-2.07(br m, 2H), 2.03(s, 3H), 1.97-1.94(br m, 2H), 1.51-1.41(m, 4H). | 14 |
| 269 | 338.2 | 8.40 | A | (DMSO-d₆) Trifluoroacetate 8.88(br s, 1H), 8.52(br s, 1H), 7.93(d, J=2.2Hz, 1H), 7.62-7.60(m, 1H), 7.32-7.19(m, 5H), 6.16(d, J=2.2Hz, 1H), 5.32-5.31(m, 1H), 4.98(d, J=6.3Hz, 2H), 3.37-3.26(m, 2H), 3.08-3.04(m, 2H), 2.12(s, 3H), 1.84-1.76(m, 4H). | 14 |
| 270 | 298.2 | 7.57 | A | (DMSO-d₆) Trifluoroacetate 7.96(br s, 2H), 7.94(d, J=2.2Hz, 1H), 7.63(t, J=6.7Hz, 1H), 7.32-7.18(m, 5H), 6.18(d, J=2.2Hz, 1H), 4.98(d, J=6.7Hz, 2H), 4.41(t, J=5.1Hz, 2H), 2.50-2.48(m, 2H), 2.11(s, 3H). | 14 |
| 271 | 330.2 | 8.89 | A | (DMSO-d₆) Trifluoroacetate 7.89(br s, 2H), 7.87(d, J=2.2Hz, 1H), 6.16(d, J=2.2Hz, 1H), 4.97-4.95(m, 1H), 4.57-4.54(m, 1H), 3.09(s, 1H), 2.13(s, 3H), 2.12-2.11(m, 2H), 1.96-1.91(m, 4H), 1.70-1.66(m, 2H), 1.63-1.43(m, 8H). | 14 |
| 272 | 316.2 | 8.54 | A | (DMSO-d₆) Trifluoroacetate 8.90(br s, 1H), 8.58(br s, 1H), 7.91(d, J=2.2Hz, 1H), 6.39(br s, 1H), 6.17(d, J=2.2Hz, 1H), 5.37-5.33(m, 1H), 4.65-4.60(m, 1H), 3.37-3.22(m, 2H), 3.11-3.06(m, 2H), 2.21(s, 3H), 2.00-1.55(m, 12H). | 14 |

TABLE B-continued

| Compound No. | ESI/MS M + H | HPLC Retention time (min.) | HPLC Analytical condition | ¹H-NMR(400 MHz)δ(ppm) | Synthetic method |
|---|---|---|---|---|---|
| 273 | 390.2 | 8.74 | A | | 14 |
| 274 | 506.3 | 10.69 | A | | 14 |
| 275 | 492.3 | 10.61 | A | | 14 |

Example 30

General Procedure for Assay of MAPKAP-K2 Enzyme Activity Inhibition

The assay of inhibitory activity was performed according to Method A described below for Compound No. 1, 2, 3, 4, 20, 21, 22, 23, 24, 25, 26, 79, 80 and 81, and Method B described below for the other compounds.

(Method A)

(Preparation of a Compound Solution)

A compound was dissolved in DMSO to make its concentration to 10 mmol/L, and further a part of the resulting solution was taken out and stored at −20° C. The stock solution was diluted with DMSO to prepare a stock solution having a 30-fold concentration of the required range. Subsequently the resultant stock solution was diluted to 1:3 to prepare a stock solution having a 10-fold concentration of the required range, and an aliquot of 5 μL of each solution was used for every reaction with 50 μL. During the continuous dilution of all compounds, the final DMSO concentration was maintained at 3% and the solubility of compounds was maximized. Compounds were routinely tested at a final concentration ranging from 300 μmol/L to 0.001 μmol/L, but were sometimes tested at a lower concentration depending upon their activity. (MAPKAP-K2 Enzyme Activity Assay)

The kinase reaction was carried out using a 96-well round-bottomed polypropylene microplate. MAPKAP-Kinase 2 was diluted to 0.5 mU/μL with diluent buffer (50 mmol/L Tris/HCl (pH7.5), 0.1 mmol/L EGTA, 0.1% (v/v) β-mercaptoethanol, and 1 mg/mL BSA). To each well was added 5 μL of a compound or 30% DMSO and subsequently 25 μL of substrate cocktail (final concentration: 10 μmol/L ATP, 30 μmol/L peptide (KKLNRTLSVA), 50 mmol/L 33P-γ-ATP/Tris solution of (pH 7.5, 0.5 μCi), 0.1 mmol/L EGTA, 10 mmol/L magnesium acetate and 0.1% β-mercaptoethanol). To each well was added 20 μL of an enzyme solution or 20 μL of a diluent buffer without contabing enzyme to initiate the reaction, After shaking the plate for 10 sec, it was fibber allowed to stand at room temperature for 30 min. The reaction was terminated with 50 μL of a 150 mmol/L phosphoric acid solution. Then, 90 μL of a reaction mixture solution was transferred to a 96-well P81 filter plate (Whatmann), and incubation was performed at room temperature for 5 min. Subsequently, the filter plate was washed 4 times with 200 μL of a 75 mmol/L phosphoric acid solution per well through a plate suction manifold (Millipore), followed by further drying in an oven for 2 to 3 hrs. Next, after adding Packard Microscint "0" (30 μL) to each well and shaking the plate for 30 min, scintillation measurement was performed using a Packard TopCount scintillation counter.

(Method B)

(Preparation of a Compound Solution)

A compound was dissolved in DMS to make its concentration to 20 mmol/L, and the resultant solution was stored at −20° C. The stock solution was sequentially diluted with DMSO to prepare a solution having a 200-fold concentration of the required range. Further the solution was diluted with water to 1:20 to prepare a solution having a 10-fold concentration of the required range, and an aliquot of 5 μL of each solution was used for every reaction with 50 μL. During the continuous dilution of all compounds, the final DMSO concentration was maintained at 0.5%. Compounds were routinely tested at a final concentration ranging from 100 μmol/L to 0.03 μmol/L, but were sometimes tested at a lower concentration depending upon their activity.

(MAPKAP-K2 Enzyme Activity Assay)

The reaction was initiated by adding 25 μL of a peptide substrate solution [60 μmol/L substrate peptide, 20 μmol/L ATP, 50 mmol/L Tris buffer (pH 7.5), 0.1 mmol/L EGTA, 0.1% β-mercaptoetanol, 20 mmol/L magnesium acetate, and 0.1 μCi [γ-33P]ATP (specific radio activity: approximately 110 TBq/mmol)] to 5 μL of a 5% DMSO solution of the test compound and subsequently adding 20 μL of a MAPKAP-K2 enzyme solution [10 mU recombinant human MAPKAP-K2, 50 mmol/L Tris buffer (pH 7.5), 0.1 mmol/L EGTA, 0.1% β-mercaptoethanol, 0.1% BSA]. After performing the reaction for 30 min at room temperature, an equivalent volume of 200 mmol/L phosphoric acid solution was added to terminate the reaction. Subsequently, 90 μL of the reaction product was adsorbed on a MultiScreen-PH Plate (Millipore) and then rinsed with 100 mmol/L phosphoric acid solution. After drying the plate, 30 μL of MicroScint-O (Packard BioScience) was added, and further the count per minute was measured by a scintillation counter to determine the inhibitory activity. The substrate peptide was Lys-Lys-Leu-Asn-Arg-Tlr-Leu-Ser-Val-Ala.

(Explanatory Note)

% Control=(X−B)/(Tot−B)×100

% Inhibition=100—% Control

X=count per minute of a test compound well

B=count per minute of a well without containing enzyme

Tot=count per minute of a well with DMSO solvent only, without containing the test compound (MAPKAP-K2 inhibitory activity)

IC50 value=the compound concentration at 50% inhibition

The efficacy of the compounds in Table A against MAP-KAP-K2 is shown in Table C below.

(The activity strength in Table C represents that +++ is IC50 value ≦2 μM, ++ is 2 μM <IC50 value≦20 μM and + is 20 μM<IC50 value ≦100 μM.

TABLE C

| Compound No. | Inhibitory activity |
|---|---|
| 5 | ++ |
| 6 | +++ |
| 9 | ++ |
| 10 | ++ |
| 11 | ++ |
| 12 | ++ |
| 13 | ++ |
| 14 | + |
| 16 | ++ |
| 17 | ++ |
| 18 | + |
| 19 | + |
| 25 | ++ |
| 26 | ++ |
| 27 | +++ |
| 28 | + |
| 29 | + |
| 30 | ++ |
| 31 | + |
| 33 | + |
| 36 | + |
| 40 | + |
| 41 | +++ |
| 42 | + |
| 43 | + |
| 44 | + |
| 45 | +++ |
| 46 | +++ |
| 47 | ++ |
| 48 | ++ |
| 49 | + |
| 50 | + |
| 51 | ++ |
| 52 | ++ |
| 53 | + |
| 54 | ++ |
| 55 | + |
| 56 | ++ |
| 57 | ++ |
| 58 | ++ |
| 59 | +++ |
| 60 | +++ |
| 61 | ++ |
| 62 | ++ |
| 63 | + |
| 64 | ++ |
| 65 | +++ |
| 66 | +++ |
| 67 | + |
| 68 | ++ |
| 69 | ++ |
| 70 | +++ |
| 71 | +++ |
| 72 | +++ |
| 73 | +++ |
| 74 | ++ |
| 75 | +++ |
| 76 | +++ |
| 77 | +++ |
| 78 | +++ |
| 80 | ++ |
| 81 | ++ |
| 82 | ++ |
| 83 | ++ |
| 84 | ++ |
| 85 | ++ |
| 86 | ++ |
| 87 | + |
| 88 | +++ |
| 89 | +++ |
| 90 | +++ |
| 91 | +++ |
| 92 | +++ |
| 93 | +++ |
| 102 | +++ |
| 239 | +++ |
| 240 | ++ |
| 244 | ++ |
| 245 | + |
| 253 | ++ |
| 256 | + |
| 259 | + |
| 260 | + |
| 261 | + |
| 263 | + |
| 264 | + |
| 268 | ++ |
| 269 | ++ |
| 270 | + |
| 271 | ++ |
| 272 | ++ |
| 273 | + |
| 274 | ++ |
| 275 | ++ |

INDUSTRIAL APPLICABILITY

A novel pyrazolo[1,5-a]pyrimidine derivative represented by Formula (I) and a pharmaceutically acceptable salt thereof exhibit an excellent MAPKAP-K2 inhibitory activity. A drug containing these compounds as an active ingredient is expected to be useful as a MAPKAP-K2-inhibitory agent, for example, as a preventive or therapeutic drug for neurodegenerative/neurologic disorder (including dementia), inflammatory disease, sepsis, autoimmune disease, destructive osteopathy, diabetes mellitus, cancer, ischemic reperfusion injury, angiopoietic disorder, cachexia, obesity, angiogenesis, asthma and/or chronic obstructive pulmonary disease (COPD).

The invention claimed is:

1. A compound of formula (I) and pharmaceutically acceptable salts:

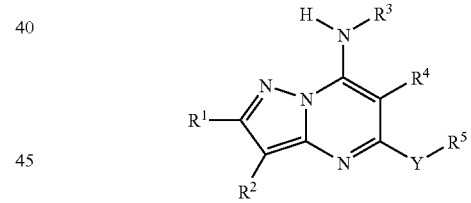

(I)

wherein
R$^1$ hydrogen;
  C1-C8 optionally substituted alkyl;
  C2-C8 optionally substituted alkenyl;
  C2-C8 optionally substituted alkynyl;
  C3-C8 optionally substituted cycloalkyl;
  C6-C14 optionally substituted aryl;
  optionally substituted heterocyclyl;
  optionally substituted arylalkyl;
  optionally substituted heterocyclylalkyl;
  optionally substituted arylalkenyl;
  optionally substituted heterocyclylalkenyl;
  optionally substituted arylalkynyl; or
  optionally substituted heterocyclylalkynyl;
R$^2$ is hydrogen;
R$^3$ is C6-C14 unsubstituted aryl;
  C6-C14 substituted aryl wherein substituents of C6-C14 aryl are at least one group selected from the group consisting of halogen, —CN, —NO$_2$, —CHO, -G-

$R^{15}$ wherein G is a single bond, —C(=O)— or —O—C(=O)— and $R^{15}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{16}$ or —NR$^{17}$R$^{18}$ wherein $R^{17}$ and $R^{18}$ may be the same or different, —NR$^{17}$C(=O)R$^{19}$, —NR$^{17}$C(=X)OR$^{18}$ wherein $R^{17}$ and $R^{18}$ may be the same or different and X is O, S, N—CN or NH, —NR$^{17}$C(=X)NR$^{18}$R$^{20}$ wherein $R^{17}$, $R^{18}$ and $R^{20}$ may be the same or different and X is O, S, N—CN or NH and —NR$^{17}$SO$_2$R$^{18}$ wherein $R^{17}$ and $R^{18}$ may be the same or different;

unsubstituted heterocyclyl; or substituted heterocyclyl wherein substituents of the heterocyclyl are at least one group selected from the group consisting of halogen, —CN, —NO$_2$, —CHO, -G-R$^{23}$ wherein G is a single bond, —C(=O)— or —O—C(=O)— and $R^{23}$ is as defined for $R^{15}$, —NR$^{24}$C(=O)R$^{25}$, —NR$^{24}$C(=X)OR$^{26}$ wherein $R^{24}$ and $R^{26}$ may be the same or different and X is O, S, N—CN or NH, —NR$^{24}$C(=X)NR$^{26}$R$^{27}$ wherein $R^{24}$, $R^{26}$ and $R^{27}$ may be the same or different and X is O, S, N—CN or NH, —NR$^{24}$SO$_2$R$^{26}$ wherein $R^{24}$ and $R^{26}$ may be the same or different, —S(O)$_m$R$^{24}$ wherein m is 0, 1 or 2 and —SO$_2$NR$^{28}$R$^{29}$ wherein $R^{28}$ and $R^{29}$ may be the same or different and $R^{28}$ and $R^{29}$ may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with 1 or 2 or more substituents;

$R^4$ is halogen;

C1-C8 optionally substituted alkyl;
C2-C8 optionally substituted alkenyl;
C2-C8 optionally substituted alkynyl;
C3-C8 optionally substituted cycloalkyl;
C6-C14 optionally substituted aryl;
optionally substituted heterocyclyl;
optionally substituted arylalkyl;
optionally substituted heterocyclylalkyl;
optionally substituted arylalkenyl;
optionally substituted heterocyclylalkenyl;
optionally substituted arylalkynyl;
optionally substituted heterocyclylalkynyl;
—OR$^{30}$;
—SR$^{30}$;
—NR$^{30}$R$^{31}$ wherein $R^{30}$ and $R^{31}$ may be the same or different;
NR$^{30}$C(=O)R$^{32}$ wherein $R^{30}$ and $R^{32}$ may be the same or different;
—NR$^{30}$C(=X)OR$^{31}$ wherein $R^{30}$ and $R^{31}$ may be the same or different and X is O, S, N—CN or NH;
—NR$^{30}$C(=X)NR$^{31}$R$^{33}$ wherein $R^{30}$, $R^{31}$ and $R^{33}$ may be the same or different and X is O, S, N—CN or NH; or
—NR$^{30}$SO$_2$R$^{31}$ wherein $R^{30}$ and $R^{31}$ may be the same or different;

$R^5$ is C1-C8 substituted alkyl;
C2-C8 optionally substituted alkenyl;
C2-C8 optionally substituted alkynyl;
C3-C8 substituted cycloalkyl wherein the C3-C8 cycloalkyl is substituted with at least one group selected from the group consisting of halogen, —CN, —NO$_2$, —CHO, =O, -G-R$^{34}$ wherein G is a single bond, —C(=O)— or —O—C(=O)— and $R^{34}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{35}$ or —NR$^{36}$R$^{37}$ wherein $R^{36}$ and $R^{37}$ may be the same or different, —NR$^{38}$C(=O)R$^{39}$, —NR$^{38}$C(=X)OR$^{40}$ wherein $R^{38}$ and $R^{40}$ may be the same or different and X is O, S, N—CN or NH, —NR$^{38}$C(=X)NR$^{40}$R$^{41}$ wherein $R^{38}$, $R^{40}$ and $R^{41}$ may be the same or different and X is O, S, N—CN or NH and —NR$^{38}$SO$_2$R$^{40}$ wherein $R^{38}$ and $R^{40}$ may be the same or different;

unsubstituted heterocyclyl;

substituted heterocyclyl wherein substituents of the heterocyclyl are at least one group selected from the group consisting of halogen, —CN, —NO$_2$, —CHO, =O, -G-R$^{42}$ wherein G is a single bond, —C(=O)— or —O—C(=O)— and $R^{42}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{43}$ or NR$^{44}$R$^{45}$ wherein $R^{44}$ and $R^{45}$ may be the same or different, —NR$^{46}$C(=O)R$^{47}$, —NR$^{46}$C(=X)OR$^{48}$ wherein $R^{46}$ and $R^{48}$ may be the same or different and X is O, S, N—CN or NH, —NR$^{46}$C(=X)NR$^{48}$R$^{49}$ wherein $R^{46}$, $R^{48}$ and $R^{49}$ may be the same or different and X is O, S, N—CN or NH and —NR$^{46}$SO$_2$R$^{48}$ wherein $R^{46}$ and $R^{48}$ may be the same or different;

optionally substituted arylalkyl;
optionally substituted heterocyclylalkyl;
optionally substituted arylalkenyl;
optionally substituted heterocyclylalkenyl;
optionally substituted arylalkynyl; or
optionally substituted heterocyclylalkynyl;

Y is —O— or —S—;

provided that $R^5$ is not C1-C6 alkyl which is unsubstituted or substituted with at least one phenyl or halogen, wherein $R^{16}$, $R^{17}$, $R^{18}$, $R^{20}$, $R^{24}$, $R^{26}$, $R^{27}$, $R^{28}$, $R^{29}$, $R^{30}$, $R^{31}$, $R^{33}$, $R^{35}$, $R^{36}$, $R^{37}$, $R^{38}$, $R^{40}$, $R^{41}$, $R^{43}$, $R^{44}$, $R^{45}$, $R^{46}$, $R^{48}$, and $R^{49}$ are hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl, and wherein $R^{19}$, $R^{25}$, $R^{32}$, $R^{39}$, $R^{47}$ are hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl.

2. The compound as claimed in claim 1 wherein $R^1$ is hydrogen or C1-C8 optionally substituted alkyl.

3. The compound as claimed in claim 1 wherein $R^1$ is hydrogen.

4. The compound as claimed in claim 1 wherein $R^3$ is C6-C14 substituted aryl and substituted with at least one group selected from the group consisting of halogen, —CN, -G-$R^{15}$ and —$NR^{17}C(=O)R^{19}$; wherein $R^{15}$, $R^{17}$, $R^{19}$ and G are as defined in claim 1.

5. The compound as claimed in claim 1 wherein $R^3$ is C6-C14 substituted aryl and substituted with at least one group selected from the group consisting of halogen, —CN, —G-$R^{15}$ wherein G is a single bond or —C(=O)— and $R^{15}$ is C1-C8 optionally substituted alkyl, C3-C8 optionally substituted cycloalkyl, C6-C14 optionally substituted aryl, optionally substituted heterocyclyl, optionally substituted arylalkyl, optionally substituted heterocyclylalkyl, —$OR^{16}$ or —$NR^{17}R^{18}$, —$NR^{17}C(=O)R^{19}$ and —$NR^{17}SO_2R^{18}$; wherein $R^{16}$, $R^{17}$, $R^{18}$ and $R^{19}$ are as defined in claim 1.

6. The compound as claimed in claim 1 wherein $R^3$ is C6-C14 substituted aryl and substituted with at least one group selected from the group consisting of halogen, —CN, -G-$R^{15}$ wherein G is a single bond and $R^{15}$ is C6-C14 optionally substituted aryl, optionally substituted heterocyclyl, optionally substituted arylalkyl, optionally substituted heterocyclylalkyl, —$OR^{16}$ or —$NR^{17}R^{18}$, —$NR^{17}C(=O)R^{19}$ and —$NR^{17}SO_2R^{18}$; wherein $R^{16}$, $R^{17}$, $R^{18}$ and $R^{19}$ are as defined in claim 1.

7. The compound as claimed in claim 1 wherein $R^3$ is C6-C14 substituted aryl and substituted with at least one group selected from the group consisting of halogen, —CN and -G-$R^{15}$ wherein G is —C(=O)— and $R^{15}$ is C1-C8 optionally substituted alkyl, C6-C14 optionally substituted aryl, C3-C8 optionally substituted cycloalkyl, —$OR^{16}$ or —$NR^{17}R^{18}$; wherein $R^{16}$, $R^{17}$ and $R^{18}$ are as defined in claim 1.

8. The compound as claimed in claim 1 wherein $R^3$ is substituted bicyclic heteroaryl and substituted with at least one group selected from the group consisting of halogen, —CN, -G-$R^{23}$, —$NR^{24}C(=O)R^{25}$ and —$SO_2NR^{28}R^{29}$; wherein $R^{23}$, $R^{24}$, $R^{25}$, $R^{28}$, $R^{29}$ and G are as defined in claim 1.

9. The compound as claimed in claim 1 wherein $R^3$ is unsubstituted bicyclic heteroaryl.

10. The compound as claimed in claim 1 wherein $R^4$ is halogen, C1-C8 optionally substituted alkyl, C2-C8 optionally substituted alkenyl or C3-C8 optionally substituted cycloalkyl.

11. The compound as claimed in claim 1 wherein $R^4$ is C1-C8 optionally substituted alkyl.

12. The compound as claimed in claim 1 wherein $R^4$ is methyl.

13. The compound as claimed in claim 1 wherein $R^5$ is C1-C8 substituted alkyl, C3-C8 substituted cycloalkyl, unsubstituted heterocyclyl or substituted heterocyclyl.

14. The compound as claimed in claim 1 wherein $R^5$ is C3-C8 substituted cycloalkyl and substituted with at least one group selected from the group consisting of halogen, —CN, =O, C1-C8 optionally substituted alkyl, C2-C8 optionally substituted alkenyl, C3-C8 optionally substituted cycloalkyl, $OR^{35}$ and —$NR^{36}R^{37}$; wherein $R^{35}$, $R^{36}$ and $R^{37}$ are as defined in claim 1.

15. The compound as claimed in claim 14 wherein $R^5$ is substituted cyclohexyl and substituted with at least one group selected from the group consisting of halogen, —CN, =O, C1-C8 optionally substituted alkyl, C2-C8 optionally substituted alkenyl, C3-C8 optionally substituted cycloalkyl, $OR^{35}$ and —$NR^{36}R^{37}$; are hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl.

16. The compound as claimed in claim 1 wherein $R^5$ is 4-amino-cyclohexyl.

17. The compound as claimed in claim 1 wherein $R^5$ is unsubstituted heterocyclyl or substituted heterocyclyl wherein the heterocyclyl is substituted with at least one group selected from the group consisting of halogen, —CN, =O, C1-C8 optionally substituted alkyl, C2-C8 optionally substituted alkenyl, C3-C8 optionally substituted cycloalkyl, O $R^{43}$ and —$NR^{44}R^{45}$; wherein $R^{43}$, $R^{44}$ and $R^{45}$ are as defined in claim 1.

18. The compound as claimed in claim 1 wherein $R^5$ is unsubstituted piperidin-3-yl, unsubstituted piperidin-4-yl or unsubstituted pyrrolidin-3-yl.

19. The compound as claimed in claim 1 wherein $R^5$ is substituted piperidin-3-yl, substituted piperidin-4-yl or substituted pyrrolidin-3-yl.

20. The compound as claimed in claim 1 wherein $R^5$ is substituted piperidin-3-yl, substituted piperidin-4-yl or substituted pyrrolidin-3-yl wherein $R^5$ is substituted with at least one group selected from the group consisting of halogen, —CN, C1-C8 optionally substituted alkyl, C2-C8 optionally substituted alkenyl and C3-C8 optionally substituted cycloalkyl.

21. The compound as claimed in claim 1 wherein Y is —O—.

22. The compound as claimed in claim 1 wherein Y is —S—.

23. A compound of the formula II-20:

(II-20)

wherein
$R^1$ is hydrogen;
C1-C8 optionally substituted alkyl;
C2-C8 optionally substituted alkenyl;
C2-C8 optionally substituted alkynyl;
C3-C8 optionally substituted cycloalkyl;
C6-C14 optionally substituted aryl;
optionally substituted heterocyclyl;
optionally substituted arylalkyl;
optionally substituted heterocyclylalkyl;
optionally substituted arylalkenyl;
optionally substituted heterocyclylalkenyl;
optionally substituted arylalkynyl; or
optionally substituted heterocyclylalkynyl;

$R^2$ is hydrogen;

$R^3$ is C6-C14 unsubstituted aryl;

C6-C14 substituted aryl wherein substituents of C6-C14 aryl are at least one group selected from the group consisting of halogen, —CN, —NO$_2$, —CHO, -G-$R^{15}$ wherein G is a single bond, —C(=O)— or —O—C(=O)— and $R^{15}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{16}$ or —NR$^{17}$R$^{18}$ wherein $R^{17}$ and $R^{18}$ may be the same or different, —NR$^{17}$C(=O)R$^{19}$, —NR$^{17}$C(=X)OR$^{18}$ wherein $R^{17}$ and $R^{18}$ may be the same or different and X is O, S, N—CN or NH, —NR$^{17}$C(=X)NR$^{18}$R$^{20}$ wherein $R^{17}$, $R^{18}$ and $R^{20}$ may be the same or different and X is O, S, N—CN or NH, —NR$^{17}$SO$_2$R$^{18}$ wherein $R^{17}$ and $R^{18}$ may be the same or different and —S(O)$_m$R$^{17}$ wherein m is 0, 1 or 2;

unsubstituted heterocyclyl; or substituted heterocyclyl wherein substituents of the heterocyclyl are at least one group selected from the group consisting of halogen, —CN, —NO$_2$, —CHO, -G-$R^{23}$ wherein G is a single bond, —C(=O)— or —O—C(=O)— and $R^{23}$ is as defined for $R^{15}$, —NR$^{24}$C(=O)R$^{25}$, —NR$^{24}$C(=X)OR$^{26}$ wherein $R^{24}$ and $R^{26}$ may be the same or different and X is O, S, N—CN or NH, —NR$^{24}$C(=X)NR$^{26}$R$^{27}$ wherein $R^{24}$, $R^{26}$ and $R^{27}$ may be the same or different and X is O, S, N—CN or NH, —NR$^{24}$SO$_2$R$^{26}$ wherein $R^{24}$ and $R^{26}$ may be the same or different —S(O)$_m$R$^{24}$ wherein m is 0, 1 or 2 and —SO$_2$NR$^{28}$R$^{29}$ wherein $R^{28}$ and $R^{29}$ may be the same or different and $R^{28}$ and $R^{29}$ may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with 1 or 2 or more substituents;

$R^4$ is halogen;

C1-C8 optionally substituted alkyl;
C2-C8 optionally substituted alkenyl;
C2-C8 optionally substituted alkynyl;
C3-C8 optionally substituted cycloalkyl;
C6-C14 optionally substituted aryl;
optionally substituted heterocyclyl;
optionally substituted arylalkyl;
optionally substituted heterocyclylalkyl;
optionally substituted arylalkenyl;
optionally substituted heterocyclylalkenyl;
optionally substituted arylalkynyl;
optionally substituted heterocyclylalkynyl;
—OR$^{30}$;
—SR$^{30}$;
—NR$^{30}$R$^{31}$ wherein $R^{30}$ and $R^{31}$ may be the same or different;
—NR$^{30}$C(=O)R$^{32}$ wherein $R^{30}$ and $R^{32}$ may be the same or different;
—NR$^{30}$C(=X)OR$^{31}$ wherein $R^{30}$ and $R^{31}$ may be the same or different and X is O, S, N—CN or NH;
—NR$^{30}$C(=X)NR$^{31}$R$^{33}$ wherein $R^{30}$, $R^{31}$ and $R^{33}$ may be the same or different and X is O, S, N—CN or NH; or
—NR$^{30}$SO$_2$R$^{31}$ wherein $R^{30}$ and $R^{31}$ may be the same or different;

$R^5$ is C1-C8 substituted alkyl;

C2-C8 optionally substituted alkenyl;
C2-C8 optionally substituted alkynyl;
C3-C8 substituted cycloalkyl wherein the C3-C8 cycloalkyl is substituted with at least one group selected from the group consisting of halogen, —CN, —NO$_2$, —CHO, =O, -G-$R^{34}$ wherein G is a single bond, —C(=O)— or —O—C(=O)— and $R^{34}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{35}$ or NR$^{36}$R$^{37}$ wherein $R^{36}$ and $R^{37}$ may be the same or different, —NR$^{38}$C(=O)R$^{39}$, —NR$^{38}$C(=X)OR$^{40}$ wherein $R^{38}$ and $R^{40}$ may be the same or different and X is O, S, N—CN or NH, —NR$^{38}$C(=X)NR$^{40}$R$^{41}$ wherein $R^{38}$, $R^{40}$ and $R^{41}$ may be the same or different and X is O, S, N—CN or NH and —NR$^{38}$SO$_2$R$^{40}$ wherein $R^{38}$ and $R^{40}$ may be the same or different;

unsubstituted heterocyclyl;

substituted heterocyclyl wherein substituents of the heterocyclyl are at least one group selected from the group consisting of halogen, —CN, —NO$_2$, —CHO, =O, -G-$R^{42}$ wherein G is a single bond, —C(=O)— or —O—C(=O)— and $R^{42}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{43}$ or —NR$^{44}$R$^{45}$ wherein $R^{44}$ and $R^{45}$ may be the same or different, —NR$^{46}$C(=O)R$^{47}$, —NR$^{46}$C(=X)OR$^{48}$ wherein $R^{46}$ and $R^{48}$ may be the same or different and X is O, S, N—CN or NH, —NR$^{46}$C(=X)NR$^{48}$R$^{49}$ wherein $R^{46}$, $R^{48}$ and $R^{49}$ may be the same or different and X is O, S, N—CN or NH and —NR$^{46}$SO$_2$R$^{48}$ wherein $R^{46}$ and $R^{48}$ may be the same or different;

optionally substituted arylalkyl;
optionally substituted heterocyclylalkyl;
optionally substituted arylalkenyl;
optionally substituted heterocyclylalkenyl;
optionally substituted arylalkynyl; or
optionally substituted heterocyclylalkynyl;

Y is —O— or —S—;

provided that $R^5$ is not C1-C6 alkyl which is unsubstituted or substituted with at least one phenyl or halogen, wherein $R^{16}$, $R^{17}$, $R^{18}$, $R^{20}$, $R^{24}$, $R^{26}$, $R^{27}$, $R^{28}$, $R^{29}$, $R^{30}$, $R^{31}$, $R^{33}$, $R^{35}$, $R^{36}$, $R^{37}$, $R^{38}$, $R^{40}$, $R^{41}$, $R^{43}$, $R^{44}$, $R^{45}$, $R^{46}$, $R^{48}$, and $R^{49}$ are hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl, and wherein $R^{19}$, $R^{25}$, $R^{32}$, $R^{39}$, $R^{47}$ are hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl; and $R^{86}$ is C1-C8 optionally substituted alkyl or optionally substituted arylalkyl.

24. The compound as claimed in claim 23 wherein $R^1$ is hydrogen.

25. The compound as claimed in claim 23 wherein $R^3$ is substituted phenyl wherein substituents of the phenyl are at least one selected from the group consisting of halogen, —CN, —NO$_2$, C1-C8 optionally substituted alkyl, C3-C8 optionally substituted cylcoalkyl, C6-C14 optionally substituted aryl, optionally substituted heterocyclyl, —OR$^{16}$ wherein R$^{16}$ is hydrogen, C1-C8 optionally substituted alkyl, optionally substituted arylalkyl or optionally substituted heterocyclylalkyl, —NR$^{17}$R$^{18}$ wherein R$^{17}$ and R$^{18}$, which may be the same or different, are hydrogen or C1-C8 optionally substituted alkyl and —C(=O)NR$^{17}$R$^{18}$ wherein R$^{17}$ and R$^{18}$, which may be the same or different, are hydrogen, C1-C8 optionally substituted alkyl, C3-C8 optionally substituted cycloalkyl, C6-C14 optionally substituted aryl or optionally substituted heterocyclyl, unsubstituted bicyclic heteroaryl, substituted bicyclic heteroaryl wherein the bicyclic heteroaryl is substituted with at least one group selected from the group consisting of halogen, —CN, —NO$_2$, C1-C8 optionally substituted alkyl, C6-C14 optionally substituted aryl, optionally substituted heterocyclyl, —OR$^{16}$ wherein R$^{16}$ is hydrogen, C1-C8 optionally substituted alkyl, optionally substituted arylalkyl or optionally substituted heterocyclylalkyl, —NR$^{17}$R$^{18}$ wherein R$^{17}$ and R$^{18}$, which may be the same or different, are hydrogen or C1-C8 optionally substituted alkyl, —NHC(=O)R$^{19}$ wherein R$^{19}$ is C1-C8 optionally substituted alkyl, C3-C8 optionally substituted cycloalkyl, C6-C14 optionally substituted aryl or optionally substituted heterocyclyl and —SR$^{17}$ wherein R$^{17}$ is C1-C8 optionally substituted alkyl.

26. The compound as claimed in claim 23 wherein $R^4$ is methyl or ethyl.

27. The compound as claimed in claim 23 wherein $R^5$ is substituted cyclohexyl wherein the cyclohexyl is substituted with at least one group selected from the group consisting of halogen, C1-C8 optionally substituted alkyl, —OH and —NH$_2$, unsubstituted saturated heterocyclyl or substituted saturated heterocyclyl wherein the saturated heterocyclyl is substituted with at least one group selected from the group consisting of halogen, C1-C8 optionally substituted alkyl, —OH and —NH$_2$.

28. The compound as claimed in claim 23 wherein Y is —O—.

29. The compound as claimed in claim 23 wherein Y is —S—.

30. The compound as claimed in claim 23 wherein $R^{86}$ is tert-butyl or benzyl.

31. The compound as claimed in claim 23 wherein $R^1$ is hydrogen; $R^2$ is hydrogen; $R^3$ is substituted phenyl wherein the substituted phenyl is substituted with at least one group selected from the group consisting of halogen, —CN, —OH, —OCH$_3$, —OEt, and —COOH; $R^4$ is —CH$_3$; $R^5$ is 4-aminocyclohexyl or piperidin-3-yl; Y is —O— or S; $R^{86}$ is tert-butyl.

* * * * *

UNITED STATES PATENT AND TRADEMARK OFFICE
CERTIFICATE OF CORRECTION

PATENT NO. : 7,667,036 B2 Page 1 of 1
APPLICATION NO. : 11/202035
DATED : February 23, 2010
INVENTOR(S) : Kosugi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 556 days.

Signed and Sealed this

Seventh Day of December, 2010

David J. Kappos
*Director of the United States Patent and Trademark Office*